US009879106B2

(12) United States Patent
Rix et al.

(10) Patent No.: US 9,879,106 B2
(45) Date of Patent: Jan. 30, 2018

(54) PRODUCING POLYOLEFIN PRODUCTS

(71) Applicant: Univation Technologies, LLC, Houston, TX (US)

(72) Inventors: Francis C. Rix, Houston, TX (US); Ching-Tai Lue, Sugar Land, TX (US); Timothy M. Boller, Houston, TX (US); Garth R. Giesbrecht, The Woodlands, TX (US); C. Jeff Harlan, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 15/117,816

(22) PCT Filed: Feb. 10, 2015

(86) PCT No.: PCT/US2015/015143
§ 371 (c)(1),
(2) Date: Aug. 10, 2016

(87) PCT Pub. No.: WO2015/123179
PCT Pub. Date: Aug. 20, 2015

(65) Prior Publication Data
US 2017/0008983 A1  Jan. 12, 2017

Related U.S. Application Data

(60) Provisional application No. 62/088,196, filed on Dec. 5, 2014, provisional application No. 62/087,905, filed
(Continued)

(51) Int. Cl.
C08F 210/16 (2006.01)
C08F 4/64 (2006.01)
(Continued)

(52) U.S. Cl.
CPC ............ *C08F 210/16* (2013.01); *C07F 17/00* (2013.01); *C08F 4/65904* (2013.01); *C08F 4/76* (2013.01);
(Continued)

(58) Field of Classification Search
CPC .............. C08F 4/65904; C08F 4/65916; C08F 4/65925; C08F 4/65927; C08F 2420/00
(Continued)

(56) References Cited

U.S. PATENT DOCUMENTS 6,943,227 B2   9/2005  Ishihama et al.
7,763,561 B2   7/2010  McDaniel et al.
(Continued)

FOREIGN PATENT DOCUMENTS

JP   2003105029   4/2003
JP   2009126902   6/2009
(Continued)

OTHER PUBLICATIONS

International Preliminary Report on Patentability for related PCT Application PCT/US2015/015143, dated Aug. 25, 2016 (10 pgs).
(Continued)

*Primary Examiner* — Fred M Teskin
(74) *Attorney, Agent, or Firm* — Brooks, Cameron & Huebsch, PLLC

(57) ABSTRACT

Catalyst systems and methods for making and using the same are described. A method includes selecting a catalyst blend using a blend polydispersity index (bPDI) map. The polydispersity map is generated by generating a number of polymers for at least two catalysts. Each polymer is generated at a different hydrogen to ethylene ratio. At least one catalyst generates a higher molecular weight polymer and another catalyst generates a lower molecular weight polymer. A molecular weight for each polymer is measured. The
(Continued)

relationship between the molecular weight of the polymers generated by each of the catalysts and the ratio of hydrogen to ethylene is determined. A family of bPDI curves for polymers that would be made using a number of ratios of a blend of the at least two catalysts for each of a number of ratios of hydrogen to ethylene. A ratio for the catalyst blend of the catalysts that generates a polymer having a bPDI that matches a polymer fabrication process is selected, and the product specific polyolefin is made using the catalyst blend.

11 Claims, 12 Drawing Sheets

Related U.S. Application Data on Dec. 5, 2014, provisional application No. 62/087,914, filed on Dec. 5, 2014, provisional application No. 62/087,911, filed on Dec. 5, 2014, provisional application No. 62/032,383, filed on Aug. 1, 2014, provisional application No. 61/985,151, filed on Apr. 28, 2014, provisional application No. 61/981,291, filed on Apr. 18, 2014, provisional application No. 61/938,472, filed on Feb. 11, 2014, provisional application No. 61/938,466, filed on Feb. 11, 2014.

(51) Int. Cl.
| | |
|---|---|
| C07F 17/00 | (2006.01) |
| C08F 210/02 | (2006.01) |
| C08F 4/76 | (2006.01) |
| C08F 4/659 | (2006.01) |
| C08J 5/18 | (2006.01) |
| C08F 2/34 | (2006.01) |
| C08L 23/08 | (2006.01) |
| C08F 210/14 | (2006.01) |
| C08F 210/08 | (2006.01) |
| C08F 4/6592 | (2006.01) |

(52) U.S. Cl.
CPC ........ *C08F 210/02* (2013.01); *C08F 4/65912* (2013.01); *C08F 4/65916* (2013.01); *C08F 4/65925* (2013.01); *C08F 4/65927* (2013.01); *C08F 210/08* (2013.01); *C08F 210/14* (2013.01); *C08F 2410/02* (2013.01); *C08F 2420/00* (2013.01); *C08F 2420/01* (2013.01); *C08F 2500/01* (2013.01); *C08F 2500/02* (2013.01); *C08F 2500/08* (2013.01); *C08F 2500/09* (2013.01); *C08F 2500/10* (2013.01); *C08F 2500/11* (2013.01); *C08F 2500/12* (2013.01); *C08F 2500/13* (2013.01); *C08F 2500/18* (2013.01); *C08F 2800/20* (2013.01); *C08L 23/0815* (2013.01)

(58) Field of Classification Search
USPC .......................................... 436/37; 526/114
See application file for complete search history.

(56) References Cited

U.S. PATENT DOCUMENTS

| 8,288,487 | B2 | 10/2012 | Yang et al. |
| 8,664,140 | B2 | 3/2014 | Schmitz et al. |
| 8,859,451 | B2 | 10/2014 | Mihan et al. |
| 8,932,975 | B2 | 1/2015 | Yang et al. |
| 8,999,875 | B2 | 4/2015 | Fantinel et al. |
| 9,346,896 | B2 | 5/2016 | McDaniel et al. |
| 2005/0159300 | A1 | 7/2005 | Jensen et al. |
| 2009/0240010 | A1 | 9/2009 | McDaniel et al. |
| 2010/0076167 | A1 | 3/2010 | McDaniel et al. |
| 2010/0317904 | A1 | 12/2010 | Small et al. |
| 2012/0010375 | A1 | 1/2012 | Yang et al. |
| 2012/0059134 | A1 | 3/2012 | Yang et al. |

FOREIGN PATENT DOCUMENTS

| WO | 99/03897 | 1/1999 |
| WO | 0109200 | 2/2001 |

OTHER PUBLICATIONS

International Search Report & Written Opinion for related PCT Application PCT/US2015/015143, dated Jul. 3, 2015 (14 pgs).
Jae Kim, et al., "Synthesis of Tailor-Made Polyethylene through the Control of Polymerization Conditions Using Selectively Combined Metallocene Catalysts in a Supported System", Journal of Polymer Science: Part A: Polymer Chemistry, vol. 37, 331-339 (10 pgs).

300

PRODUCING POLYOLEFIN PRODUCTS

RELATED APPLICATIONS

This application is a National Stage Application under 35 U.S.C. § 371 of International Application Number PCT/US2015/015143, filed Feb. 10, 2015 and published as WO 2015/123179 on Aug. 20, 2015, which claims the benefit to the following U.S. Provisional Applications 61/938,466, filed Feb. 11, 2014; 61/938,472, filed Feb. 11, 2014; 61/981,291, filed Apr. 18, 2014; 61/985,151, filed Apr. 28, 2014; 62/032,383, filed Aug. 1, 2014; 62/087,911, filed Dec. 5, 2014; 62/087,914, filed Dec. 5, 2014; 62/087,905, filed Dec. 5, 2014; 62/088,196, filed Dec. 5, 2014; the entire contents of which are incorporated herein by reference in its entirety.

BACKGROUND

Ethylene alpha-olefin (polyethylene) copolymers are typically produced in a low pressure reactor, utilizing, for example, solution, slurry, or gas phase polymerization processes. Polymerization takes place in the presence of catalyst systems such as those employing, for example, a Ziegler-Natta catalyst, a chromium based catalyst, a metallocene catalyst, or combinations thereof.

A number of catalyst compositions containing single site, e.g., metallocene, catalysts have been used to prepare polyethylene copolymers, producing relatively homogeneous copolymers at good polymerization rates. In contrast to traditional ziegler-Natta catalyst compositions, single site catalyst compositions, such as metallocene catalysts, are catalytic compounds in which each catalyst molecule contains one or only a few polymerization sites. Single site catalysts often produce polyethylene copolymers that have a narrow molecular weight distribution. Although there are single site catalysts that can produce broader molecular weight distributions, these catalysts often show a narrowing of the molecular weight distribution as the reaction temperature is increased, for example, to increase production rates. Further, a single site catalyst will often incorporate comonomer among the molecules of the polyethylene copolymer at a relatively uniform rate. The molecular weight distribution and the amount of comonomer incorporation can be used to determine a composition distribution.

The composition distribution of an ethylene alpha-olefin copolymer refers to the distribution of comonomer, which form short chain branches, among the molecules that comprise the polyethylene polymer. When the amount of short chain branches varies among the polyethylene molecules, the resin is said to have a "broad" composition distribution. When the amount of comonomer per 1000 carbons is similar among the polyethylene molecules of different chain lengths, the composition distribution is said to be "narrow".

The composition distribution is known to influence the properties of copolymers, for example, stiffness, toughness, extracTable content, environmental stress crack resistance, and heat sealing, among other properties. The composition distribution of a polyolefin may be readily measured by methods known in the art, for example, Temperature Raising Elution Fractionation (TREF) or Crystallization Analysis Fractionation (CRYSTAF).

It is generally known in the art that a polyolefin's composition distribution is largely dictated by the type of catalyst used and is typically invariable for a given catalyst system. Ziegler-Natta catalysts and chromium based catalysts produce resins with broad composition distributions (BCD), whereas metallocene catalysts normally produce resins with narrow composition distributions (NCD).

Resins having a broad orthogonal composition distribution (BOCD) in which the comonomer is incorporated predominantly in the high molecular weight chains can lead to improved physical properties, for example toughness properties and environmental stress crack resistance (ESCR). Because of the improved physical properties of resins with orthogonal composition distributions needed for commercially desirable products, there exists a need for controlled techniques for forming polyethylene copolymers having a broad orthogonal composition distribution.

SUMMARY

An exemplary embodiment described herein provides a method of selecting catalysts for making a product specific polyolefin using a blend polydispersity index (bPDI) map. The method includes generating a number of polymers for at least two catalysts, wherein each polymer is generated at a different hydrogen to ethylene ratio. One of the catalysts generates a higher molecular weight (hmw) polymer and another of the at least two catalysts generates a lower molecular weight (lmw) polymer. The weight averaged molecular weight and PDI is measured for each polymer. The relationship between the molecular weight of the polymers generated by each of the at least two catalysts and the ratio of hydrogen to ethylene is generated. A family of bPDI curves for polymers that would be made using a number of ratios of a blend of the at least two catalysts for each of a number of ratios of hydrogen to ethylene is generated. A ratio for a blend of the catalysts is selected that generates a polymer having a bPDI that matches a polymer fabrication process. The ratio of the catalysts is confirmed by generating a polymer at each of the number of ratios of hydrogen to ethylene.

Another exemplary embodiment provides a method of making a product specific polyolefin. The method includes selecting a catalyst blend based, at least in part, on a polydispersity index (PDI) map. The polydispersity map is generated by generating a number of polymers for at least two catalysts, wherein each polymer is generated at a different hydrogen to ethylene ratio. At least one of the catalysts generates a higher molecular weight polymer and another of the catalysts generates a lower molecular weight polymer. The molecular weight is measured for each polymer. The relationship between the molecular weight of the polymers generated by each of the at least two catalysts and the ratio of hydrogen to ethylene is determined. A family of bPDI curves for polymers that would be made using a number of ratios of a blend of the catalysts for each of a number of ratios of hydrogen to ethylene is generated. A ratio for the catalyst blend of the at least two catalysts that generates a polymer having a bPDI that matches a polymer fabrication process is selected. The product specific polyolefin is generated using the catalyst blend.

Another exemplary embodiment provides a polymerization catalyst for forming a polyethylene copolymer. The polymerization catalyst includes a catalyst support and a blend of at least two catalysts. The catalysts are selected by generating a number of polymers for the catalysts, wherein each polymer is generated at a different hydrogen to ethylene ratio. One of the catalysts generates a polymer with a higher weight average molecular weight (hmw) and another of the catalysts generates a polymer with a lower weight average molecular weight (1 mw). The ratio of hmw to 1 mw is greater than about 5.0 at a weight average molecular weight of between about 30,000 and about 150,000. The molecular weight is measured for each polymer and the relationship between the molecular weight of the polymers generated by each of the at least two catalysts and the ratio of hydrogen to ethylene is determined. A family of bPDI curves for polymers that would be made using a number of ratios of a blend of the catalysts for each of a number of ratios of hydrogen to ethylene is generated. A ratio for the catalyst blend of the catalysts that generates a polymer having a bPDI that matches a polymer fabrication process is selected.

Another exemplary embodiment provides a polymerization catalyst for forming a polyethylene copolymer. The polymerization catalyst includes a catalyst support and a first catalyst that is impregnated on the catalyst support, wherein the first catalyst generates polymers having a slope for a plot of $H_2/C_2$ versus $1/Mw$ of between about $1.0 \times 10^{-6}$ and about $1.5 \times 10^{-6}$, and wherein at a $C_6/C_2$ ratio of between about 0.008 and about 0.012. The first catalyst generates a polymer having an MI of about 1.0 dg/10 min, a density of about 0.92 g/cc, and an melt index ratio (MIR) less than about 25. A second catalyst is impregnated on the catalyst support with the first catalyst, wherein the second catalyst generates polymers having a slope for a plot of $H_2/C_2$ versus $1/Mw$ of between about $3.0 \times 10^{-6}$ and about $4 \times 10^{-6}$, and wherein at a $C_6/C_2$ ratio of between about 0.03 and about 0.04, the second catalyst generates a polymer having an MI of about 1.0 dg/10 min, a density of about 0.92 g/cc, and an melt index ratio (MIR) less than about 25.

DETAILED DESCRIPTION

Figure 1:
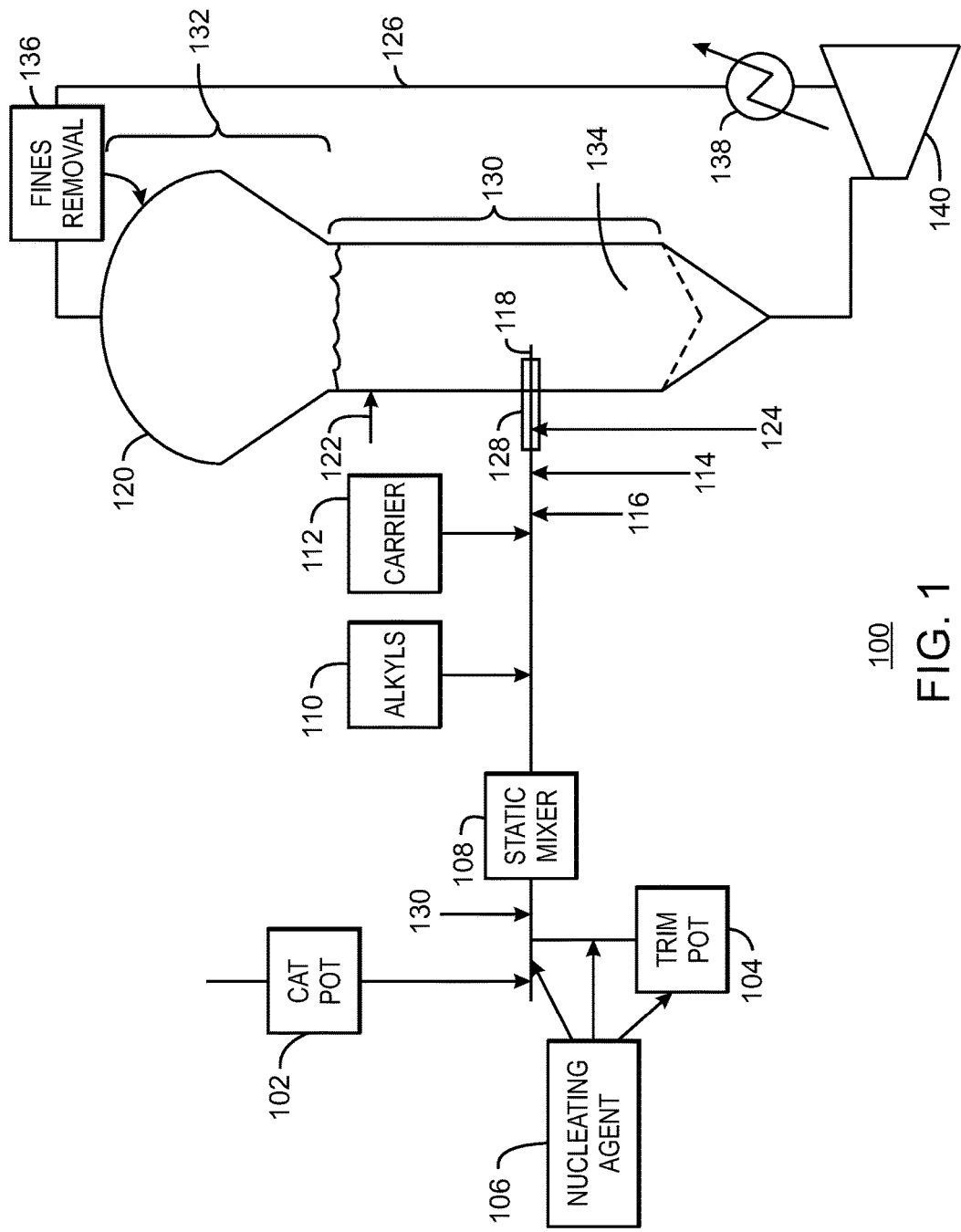
FIG. 1 is a schematic of a gas-phase reactor system, showing the addition of at least two catalysts, at least one of which is added as a trim catalyst.

It has been discovered that when a support is impregnated with multiple catalysts, new polymeric materials with an improved balance of stiffness, toughness and processability can be achieved, e.g., by controlling the amounts and types of catalysts present on the support. As described in embodiments herein, an appropriate selection of the catalysts and ratios may be used to adjust the molecular weight distribution (MWD), short chain branch distribution (SCBD), and long-chain branch distribution (LCBD) of the polymer, for example, to provide a polymer with a broad orthogonal composition distribution (BOCD). The MWD, SCBD, and LCBDs would be controlled by combining catalysts with the appropriate weight average molecular weight (Mw), comonomer incorporation, and long chain branching (LCB) formation under the conditions of the polymerization.

Employing multiple pre-catalysts that are co-supported on a single support mixed with an activator, such as a silica methylaluminoxane (SMAO), can provide a cost advantage by making the product in one reactor instead of multiple reactors. Further, using a single support also ensures intimate mixing of the polymers and offers improved operability relative to preparing a mixture of polymers of different Mw and density independently from multiple catalysts in a single reactor. As used herein, a pre-catalyst is a catalyst compound prior to exposure to activator.

As an example, for linear low-density polyethylene film (LLDPE) film applications, it would be desirable to prepare an ethylene hexene copolymer with a molecular weight of between about 90 Kg/mol and 110 Kg/mol, or about 100 Kg/mol and an average density of between about 0.9 and 0.925, or about 0.918. The typical MWD for linear metallocene resins is 2.5-3.5. Blend studies indicate that it would be desirable to broaden this distribution by employing two catalysts that each provides different average molecular weights. The ratio of the Mw for the low molecular weight component and the high molecular weight component would be between 1:1 and 1:10, or about 1:2 and 1:5.

The density of a polyethylene copolymer provides an indication of the incorporation of comonomer into a polymer, with lower densities indicating higher incorporation. The difference in the densities of the low molecular weight (LMW) component and the high molecular weight (HMW) component would preferably be greater than about 0.02, or greater than about 0.04 with the HMW component having a lower density than the LMW component. For two resins with Mw of 25 Kg/mol and 125 Kg/mol, the difference in density requires around a 1.5:1 or preferably about 2:1, or more preferably about 3:1 or more preferably a 4:1 or even a greater than 4:1 difference in comonomer incorporation ability. It is also desirable to minimize the level of long chain branching (LCB) in the polymer as that provides strong orientation in film fabrication which imbalances MD/TD tear and reduces toughness.

These factors can be adjusted by controlling the MWD and SCBD, which, in turn, can be adjusted by changing the relative amount of the two pre-catalysts on the support. This may be adjusted during the formation of the pre-catalysts, for example, by supporting two catalysts on a single support. In some embodiments, the relative amounts of the pre-catalysts can be adjusted by adding one of the components to a catalyst mixture en-route to the reactor in a process termed "trim". Feedback of polymer property data can be used to control the amount of catalyst addition. Metallocenes (MCNs) are known to trim well with other catalysts.

Further, a variety of resins with different MWD, SCBD, and LCBD may be prepared from a limited number of catalysts. To perform this function, the pre-catalysts should trim well onto activator supports. Two parameters that benefit this are solubility in alkane solvents and rapid supportation on the catalyst slurry en-route to the reactor. This favors the use of MCNs to achieve controlled MWD, SCBD, and LCBD. Techniques for selecting catalysts that can be used to generate targeted molecular weight compositions, including BOCD polymer systems, are disclosed herein.

Various catalyst systems and components may be used to generate the polymers and molecular weight compositions disclosed. These are discussed in the sections to follow. The first section discusses catalyst compounds that can be used in embodiments. The second section discusses generating catalyst slurrys that may be used for implementing the techniques described. The third section discusses catalyst supports that may be used. The fourth section discusses catalyst activators that may be used. The fifth section discusses the catalyst component solutions that may be used to add additional catalysts in trim systems. Gas phase polymerizations may use static control or continuity agents, which are discussed in the sixth section. A gas-phase polymerization reactor with a trim feed system is discussed in the seventh section. The use of the catalyst composition to control product properties is discussed in an eighth section and an exemplary polymerization process is discussed in a ninth section. Examples of the implementation of the procedures discussed is incorporated into a tenth section.

Catalyst Compounds

Metallocene Catalyst Compounds

Metallocene catalyst compounds can include "half sandwich" and/or "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The Cp ligands are one or more rings or ring system(s), at least a portion of which includes i-bonded systems, such as cycloalkadienyl ligands and heterocyclic analogues. The ring(s) or ring system(s) typically include atoms selected from the group consisting of Groups 13 to 16 atoms, and, in a particular exemplary embodiment, the atoms that make up the Cp ligands are selected from the group consisting of carbon, nitrogen, oxygen, silicon, sulfur, phosphorous, germanium, boron, aluminum, and combinations thereof, where carbon makes up at least 50% of the ring members. In a more particular exemplary embodiment, the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "$H_4$ Ind"), substituted versions thereof (as discussed and described in more detail below), and heterocyclic versions thereof.

The metal atom "M" of the metallocene catalyst compound can be selected from the group consisting of Groups 3 through 12 atoms and lanthanide Group atoms in one exemplary embodiment; and selected from the group consisting of Groups 3 through 10 atoms in a more particular exemplary embodiment, and selected from the group consisting of Sc, Ti, Zr, Hf, V, Nb, Ta, Mn, Re, Fe, Ru, Os, Co, Rh, Ir, and Ni in yet a more particular exemplary embodiment; and selected from the group consisting of Groups 4, 5, and 6 atoms in yet a more particular exemplary embodiment, and Ti, Zr, Hf atoms in yet a more particular exemplary embodiment, and Hf in yet a more particular exemplary embodiment. The oxidation state of the metal atom "M" can range from 0 to +7 in one exemplary embodiment; and in a more particular exemplary embodiment, can be +1, +2, +3, +4, or +5; and in yet a more particular exemplary embodiment can be +2, +3 or +4. The groups bound to the metal atom "M" are such that the compounds described below in the formulas and structures are electrically neutral, unless otherwise indicated. The Cp ligand forms at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst compounds can be represented by the formula (I):

$$Cp^A Cp^B MX_n \qquad (I)$$

in which M is as described above; each X is chemically bonded to M; each Cp group is chemically bonded to M; and n is 0 or an integer from 1 to 4, and either 1 or 2 in a particular exemplary embodiment.

The ligands represented by $Cp^A$ and $Cp^B$ in formula (I) can be the same or different cyclopentadienyl ligands or ligands isolobal to cyclopentadienyl, either or both of which can contain heteroatoms and either or both of which can be substituted by a group R. In at least one specific embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (I) can be unsubstituted or substituted with any one or combination of substituent groups R. Non-limiting examples of substituent groups R as used in structure (I) as well as ring substituents in structures Va-d, discussed and described below, include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. More particular non-limiting examples of alkyl substituents R associated with formulas (I) through (Va-d) include methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like.

As used herein, and in the claims, hydrocarbyl substituents, or groups, are made up of between 1 and 100 or more carbon atoms, the remainder being hydrogen. Non-limiting examples of hydrocarbyl substituents include linear or branched or cyclic: alkyl radicals; alkenyl radicals; alkynyl radicals; cycloalkyl radicals; aryl radicals; alkylene radicals, or a combination thereof. Non-limiting examples include methyl, ethyl, propyl, butyl, pentyl, hexyl, cyclopentyl, cyclohexyl; olefinically unsaturated substituents including vinyl-terminated ligands (for example but-3-enyl, prop-2-enyl, hex-5-enyl and the like), benzyl or phenyl groups and the like, including all their isomers, for example tertiary butyl, isopropyl, and the like.

As used herein, and in the claims, substituted hydrocarbyl substituents, or groups, are made up of between 1 and 100 or more carbon atoms, the remainder being hydrogen, fluorine, chlorine, bromine, iodine, oxygen, sulfur, nitrogen, phosphorous, boron, silicon, germanium or tin atoms or other atom systems tolerant of olefin polymerization systems. Substituted hydrocarbyl substituents are carbon based radicals. Non-limiting examples of substituted hydrocarbyl substituents trifluoromethyl radical, trimethylsilanemethyl (Me3SiCH 2-) radicals.

As used herein, and in the claims, heteroatom substituents, or groups, are fluorine, chlorine, bromine, iodine, oxygen, sulfur, nitrogen, phosphorous, boron, silicon, germanium or tin based radicals. They may be the heteroatom atom by itself. Further, heteroatom substituents include organometalloid radicals. Non-limiting examples of heteroatom substituents include chloro radicals, fluoro radicals, methoxy radicals, diphenyl amino radicals, thioalkyls, thioalkenyls, trimethylsilyl radicals, dimethyl aluminum radicals, alkoxydihydrocarbylsilyl radicals, siloxydiydrocabylsilyl radicals, tris(perflourophenyl)boron and the like.

Other possible radicals include substituted alkyls and aryls such as, for example, fluoromethyl, fluroethyl, difluroethyl, iodopropyl, bromohexyl, chlorobenzyl, hydrocarbyl substituted organometalloid radicals including trimethylsilyl, trimethylgermyl, methyldiethylsilyl, and the like, and halocarbyl-substituted organometalloid radicals, including tris(trifluoromethyl)silyl, methylbis(difluoromethyl)silyl, bromomethyldimethylgermyl and the like; and disubstituted boron radicals including dimethylboron, for example; and disubstituted Group 15 radicals including dimethylamine, dimethylphosphine, diphenylamine, methylphenylphosphine, as well as Group 16 radicals including methoxy, ethoxy, propoxy, phenoxy, methylsulfide and ethylsulfide. Other substituent groups R include, but are not limited to, olefins such as olefinically unsaturated substituents including vinyl-terminated ligands such as, for example, 3-butenyl, 2-propenyl, 5-hexenyl, and the like. In one exemplary embodiment, at least two R groups (two adjacent R groups in a particular exemplary embodiment) are joined to form a ring structure having from 3 to 30 atoms selected from the group consisting of carbon, nitrogen, oxygen, phosphorous, silicon, germanium, aluminum, boron, and combinations thereof. Also, a substituent group R such as 1-butanyl can form a bonding association to the element M.

Each X in the formula (I) above and for the formula/structures (II) through (Va-d) below is independently selected from the group consisting of: any leaving group, in one exemplary embodiment; halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof, in a more particular exemplary embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxyla yield a new polymerization catalyst tes, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular exemplary embodiment; hydride, chloride, fluoride, methyl, phenyl, phenoxy, benzoxy, tosyl, fluoromethyls and fluorophenyls, in yet a more particular exemplary embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls, and $C_1$ to $C_{12}$ heteroatom-containing alkylaryls, in yet a more particular exemplary embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls, in yet a more particular exemplary embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls), in yet a more particular exemplary embodiment; and fluoride, in yet a more particular exemplary embodiment.

Other non-limiting examples of X groups include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides, halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one exemplary embodiment, two or more X's form a part of a fused ring or ring system. In at least one specific embodiment, X can be a leaving group selected from the group consisting of chloride ions, bromide ions, $C_1$ to $C_{10}$ alkyls, and $C_2$ to $C_{12}$ alkenyls, carboxylates, acetylacetonates, and alkoxides.

The metallocene catalyst compound includes those of formula (I) where $Cp^A$ and $Cp^B$ are bridged to each other by at least one bridging group, (A), such that the structure is represented by formula (II):

$$Cp^A(A)Cp^BMX_n \qquad (II)$$

These bridged compounds represented by formula (II) are known as "bridged metallocenes." The elements $Cp^A$, $Cp^B$, M, X and n in structure (II) are as defined above for formula (I); where each Cp ligand is chemically bonded to M, and (A) is chemically bonded to each Cp. The bridging group (A) can include divalent hydrocarbon groups containing at least one Group 13 to 16 atom, such as, but not limited to, at least one of a carbon, oxygen, nitrogen, silicon, aluminum, boron, germanium, tin atom, and combinations thereof; where the heteroatom can also be $C_1$ to $C_{12}$ alkyl or aryl substituted to satisfy neutral valency. In at least one specific embodiment, the bridging group (A) can also include substituent groups R as defined above (for formula (I)) including halogen radicals and iron. In at least one specific embodiment, the bridging group (A) can be represented by $C_1$ to $C_6$ alkylenes, substituted $C_1$ to $C_6$ alkylenes, oxygen, sulfur, $R'_2C=$, $R'_2Si=$, $=Si(R')_2Si(R'_2)=$, $R'_2Ge=$, and $R'P=$, where "=" represents two chemical bonds, R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and where two or more R' can be joined to form a ring or ring system. In at least one specific embodiment, the bridged metallocene catalyst compound of formula (II) includes two or more bridging groups (A). In one or more embodiments, (A) can be a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls, where the heteroatom containing hydrocarbonyls include from one to three heteroatoms.

The bridging group (A) can include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl, and the corresponding moieties where the Si atom is replaced by a Ge or a C atom; as well as dimethylsilyl, diethylsilyl, dimethylgermyl and diethylgermyl. The bridging group (A) can also include —Si(hydrocarbyl)2-O-(hydrocarbyl)2Si— —Si(substitutedhydrocarbyl)2-O-(substitutedhydrocarbyl)2Si— groups and the like such as —SiMe2-O—SiMe2- and —SiPh2-O—SiPh2-.

The bridging group (A) can also be cyclic, having, for example, 4 to 10 ring members; in a more particular exemplary embodiment, bridging group (A) can have 5 to 7 ring members. The ring members can be selected from the elements mentioned above, and, in a particular embodiment, can be selected from one or more of B, C, Si, Ge, N, and O. Non-limiting examples of ring structures which can be present as, or as part of, the bridging moiety are cyclobutylidene, cyclopentylidene, cyclohexylidene, cycloheptylidene, cyclooctylidene and the corresponding rings where one or two carbon atoms are replaced by at least one of Si, Ge, N and O. In one or more embodiments, one or two carbon atoms can be replaced by at least one of Si and Ge. The bonding arrangement between the ring and the Cp groups can be cis-, trans-, or a combination thereof.

The cyclic bridging groups (A) can be saturated or unsaturated and/or can carry one or more substituents and/or can be fused to one or more other ring structures. If present, the one or more substituents can be, in at least one specific embodiment, selected from the group consisting of hydrocarbyl (e.g., alkyl, such as methyl) and halogen (e.g., F, Cl). The one or more Cp groups to which the above cyclic bridging moieties can optionally be fused can be saturated or unsaturated, and are selected from the group consisting of those having 4 to 10, more particularly 5, 6, or 7 ring members (selected from the group consisting of C, N, O, and S in a particular exemplary embodiment) such as, for example, cyclopentyl, cyclohexyl and phenyl. Moreover, these ring structures can themselves be fused such as, for example, in the case of a naphthyl group. Moreover, these (optionally fused) ring structures can carry one or more substituents. Illustrative, non-limiting examples of these substituents are hydrocarbyl (particularly alkyl) groups and halogen atoms. The ligands $Cp^A$ and $Cp^B$ of formula (I) and (II) can be different from each other. The ligands $Cp^A$ and $Cp^B$ of formula (I) and (II) can be the same. The metallocene catalyst compound can include bridged mono-ligand metallocene compounds (e.g., mono cyclopentadienyl catalyst components).

It is contemplated that the metallocene catalyst components discussed and described above include their structural or optical or enantiomeric isomers (racemic mixture), and, in one exemplary embodiment, can be a pure enantiomer. As used herein, a single, bridged, asymmetrically substituted metallocene catalyst compound having a racemic and/or meso isomer does not, itself, constitute at least two different bridged, metallocene catalyst components.

As noted above, the amount of the transition metal component of the one or more metallocene catalyst compounds in the catalyst system can range from a low of about 0.0.01 wt. %, about 0.2 wt %, about 3 wt. %, about 0.5 wt. %, or about 0.7 wt. % to a high of about 1 wt. %, about 2 wt. %, about 2.5 wt. %, about 3 wt. %, about 3.5 wt. %, or about 4 wt. %, based on the total weight of the catalyst system.

The "metallocene catalyst compound" can include any combination of any "embodiment" discussed and described herein. For example, the metallocene catalyst compound can include, but is not limited to, bis(n-propylcyclopentadienyl) hafnium $(CH_3)_2$, bis(n-propylcyclopentadienyl) hafnium $F_2$, bis(n-propylcyclopentadienyl) hafnium $Cl_2$, or bis(n-butyl, methyl cyclopentadienyl) zirconium $Cl_2$, or any combination thereof.

Other metallocene catalyst compounds that may be used are supported constrained geometry catalysts (sCGC) that include (a) an ionic complex, (b) a transition metal compound, (c) an organometal compound, and (d) a support material. In some embodiments, the sCGC catalyst may include a borate ion. The borate anion is represented by the formula $[BQ_{4-z'}(G_q(T-H)_r)_{z'}]^{d-}$, wherein: B is boron in a valence state of 3; Q is selected from the group consisting of hydride, dihydrocarbylamido, halide, hydrocarbyloxide, hydrocarbyl, and substituted-hydrocarbyl radicals; z' is an integer in a range from 1 to 4; G is a polyvalent hydrocarbon radical having r+1 valencies bonded to M' and r groups (T-H); q is an integer, 0 or 1; the group (T-H) is a radical wherein T includes O, S, NR, or PR, the O, S, N or P atom of which is bonded to hydrogen atom H, wherein R is a hydrocarbyl radical, a trihydrocarbylsilyl radical, a trihydrocarbyl germyl radical or hydrogen; r is an integer from 1 to 3; and d is 1. Alternatively the borate ion may be representative by the formula $[BQ_{4-z'}(G_q(T-M^\circ R^C_{x-1}X^a_y)_r)_{z'}]^{d-}$, wherein: B is boron in a valence state of 3; Q is selected from the group consisting of hydride, dihydrocarbylamido, halide, hydrocarbyloxide, hydrocarbyl, and substituted-hydrocarbyl radicals; z' is an integer in a range from 1 to 4; G is a polyvalent hydrocarbon radical having r+1 valencies bonded to B and r groups $(T-M^\circ R^C_{x-1}X^a_y)$; q is an integer, 0 or 1; the group $(T-M^\circ R^C_{x-1}X^a_y)$ is a radical wherein T includes O, S, NR, or PR, the O, S, N or P atom of which is bonded to $M^\circ$, wherein R is a hydrocarbyl radical, a trihydrocarbylsilyl radical, a trihydrocarbyl germyl radical or hydrogen; $M^\circ$ is a metal or metalloid selected from Groups 1-14 of the Periodic Table of the Elements, $R^C$ independently each occurrence is hydrogen or a group having from 1 to 80 nonhydrogen atoms which is hydrocarbyl, hydrocarbylsilyl, or hydrocarbylsilylhydrocarbyl; $X^a$ is a noninterfering group having from 1 to 100 nonhydrogen atoms which is halo-substituted hydrocarbyl, hydrocarbylamino-substituted hydrocarbyl, hydrocarbyloxy-substituted hydrocarbyl, hydrocarbylamino, di(hydrocarbyl)amino, hydrocarbyloxy or halide; x is a nonzero integer which may range from 1 to an integer equal to the valence of $M^\circ$; y is zero or a nonzero integer which may range from 1 to an integer equal to 1 less than the valence of $M^\circ$; and x+y equals the valence of $M^\circ$; r is an integer from 1 to 3; and d is 1. In some embodiments, the borate ion may be of the above described formulas where z' is 1 or 2, q is 1, and r is 1.

The catalyst system can include other single site catalysts such as Group 15-containing catalysts. The catalyst system can include one or more second catalysts in addition to the single site catalyst compound such as chromium-based catalysts, Ziegler-Natta catalysts, one or more additional single-site catalysts such as metallocenes or Group 15-containing catalysts, bimetallic catalysts, and mixed catalysts. The catalyst system can also include $AlCl_3$, cobalt, iron, palladium, or any combination thereof.

Examples of structures of MCN compounds that may be used in embodiments include the hafnium compound shown as formula (III), the zirconium compounds shown as formulas (IV-A-C), and bridged zirconium compounds, shown as formulas (V-A-B).

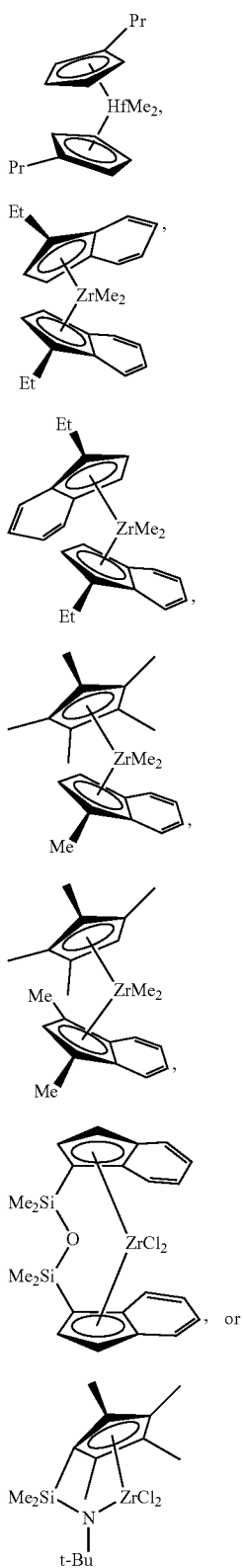

Although these compounds are shown with methyl- and chloro-groups attached to the central metal, it can be understood that these groups may be different without changing the catalyst involved. For example, each of these substituents may independently be a methyl group (Me), a chloro group (Cl), a fluoro group (F), or any number of other groups, including organic groups, or heteroatom groups. Further, these substituents will change during the reaction, as a pre-catalyst is converted to the active catalyst for the reaction. Further, any number of other substituents may be used on the ring structures, including any of the substituents described above with respect to formulas (I) and (II).

Group 15 Atom and Metal-Containing Catalyst Compounds

The catalyst system can include one or more Group 15 metal-containing catalyst compounds, such as [(2,3,4,5,6 Me$_5$C$_6$N)CH$_2$CH$_2$]$_2$NHZrBn$_2$, where Bn is a benzyl group. The Group 15 metal-containing compound generally includes a Group 3 to 14 metal atom, a Group 3 to 7, or a Group 4 to 6 metal atom. In many embodiments, the Group 15 metal-containing compound includes a Group 4 metal atom bound to at least one leaving group and also bound to at least two Group 15 atoms, at least one of which is also bound to a Group 15 or 16 atom through another group.

In one or more embodiments, at least one of the Group 15 atoms is also bound to a Group 15 or 16 atom through another group which may be a C$_1$ to C$_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and can optionally be bound to hydrogen, a halogen, a heteroatom or a hydrocarbyl group, or a heteroatom containing group.

The Group 15-containing metal compounds can be described more particularly with formulas (VI) or (VII):

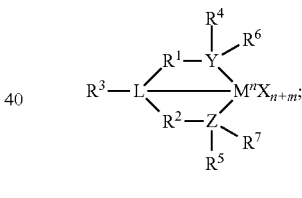

(VI)

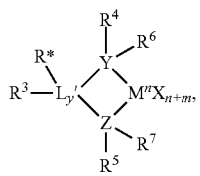

(VII)

in which M is a Group 3 to 12 transition metal or a Group 13 or 14 main group metal, a Group 4, 5, or 6 metal. In many embodiments, M is a Group 4 metal, such as zirconium, titanium or hafnium. Each X is independently a leaving group, such as an anionic leaving group. The leaving group may include a hydrogen, a hydrocarbyl group, a heteroatom, a halogen, or an alkyl; y is 0 or 1 (when y is 0 group L' is absent). The term 'n' is the oxidation state of M. In various embodiments, n is +3, +4, or +5. In many embodiments, n is +4. The term 'm' represents the formal charge of the YZL or YZL' ligand, and is 0, −1, −2 or −3 in various embodiments. In many embodiments, m is −2. L is a Group 15 or 16 element, such as nitrogen; L' is a Group 15 or 16 element or Group 14 containing group, such as carbon, silicon or germanium. Y is a Group 15 element, such as nitrogen or phosphorus. In many embodiments, Y is nitrogen. Z is a Group 15 element, such as nitrogen or phosphorus. In many embodiments, Z is nitrogen. $R^1$ and $R^2$ are, independently, a $C_1$ to $C_{20}$ hydrocarbon group, a heteroatom containing group having up to twenty carbon atoms, silicon, germanium, tin, lead, or phosphorus. In many embodiments, $R^1$ and $R^2$ are a $C_2$ to $C_{20}$ alkyl, aryl, or aralkyl group, such as a linear, branched, or cyclic $C_2$ to $C_{20}$ alkyl group, or a $C_2$ to $C_6$ hydrocarbon group. $R^1$ and $R^2$ may also be interconnected to each other. $R^3$ may be absent or may be a hydrocarbon group, a hydrogen, a halogen, a heteroatom containing group. In many embodiments, $R^3$ is absent or a hydrogen, or a linear, cyclic or branched alkyl group having 1 to 20 carbon atoms. $R^4$ and $R^5$ are independently an alkyl group, an aryl group, substituted aryl group, a cyclic alkyl group, a substituted cyclic alkyl group, a cyclic aralkyl group, a substituted cyclic aralkyl group or multiple ring system, often having up to 20 carbon atoms. In many embodiments, $R^4$ and $R^5$ have between 3 and 10 carbon atoms, or are a $C_1$ to $C_{20}$ hydrocarbon group, a $C_1$ to $C_{20}$ aryl group or a $C_1$ to $C_{20}$ aralkyl group, or a heteroatom containing group. $R^4$ and $R^5$ may be interconnected to each other. $R^6$ and $R^7$ are independently absent, hydrogen, an alkyl group, halogen, heteroatom, or a hydrocarbyl group, such as a linear, cyclic, or branched alkyl group having 1 to 20 carbon atoms. In many embodiments, $R^6$ and $R^7$ are absent. R* may be absent, or may be a hydrogen, a Group 14 atom containing group, a halogen, or a heteroatom containing group.

By "formal charge of the YZL or YZL' ligand," it is meant the charge of the entire ligand absent the metal and the leaving groups X. By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups. An alkyl group may be linear, branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In one or more embodiments, $R^4$ and $R^5$ are independently a group represented by the following formula (VIII).

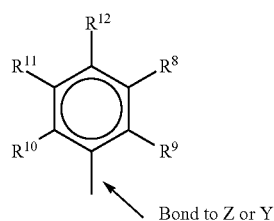

(VIII)

Bond to Z or Y

When $R^4$ and $R^5$ are as formula VII, $R^8$ to $R^{12}$ are each independently hydrogen, a $C_1$ to $C_{40}$ alkyl group, a halide, a heteroatom, a heteroatom containing group containing up to 40 carbon atoms. In many embodiments, $R^8$ to $R^{12}$ are a $C_1$ to $C_{20}$ linear or branched alkyl group, such as a methyl, ethyl, propyl, or butyl group. Any two of the R groups may form a cyclic group and/or a heterocyclic group. The cyclic groups may be aromatic. In one embodiment $R^9$, $R^{10}$ and $R^{12}$ are independently a methyl, ethyl, propyl, or butyl group (including all isomers). In another embodiment, $R^9$, $R^{10}$ and $R^{12}$ are methyl groups, and $R^8$ and $R^{11}$ are hydrogen.

In one or more embodiments, $R^4$ and $R^5$ are both a group represented by the following formula (IX).

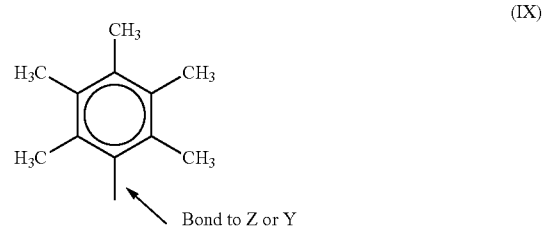

(IX)

Bond to Z or Y

When $R^4$ and $R^5$ follow formula IX, M is a Group 4 metal, such as zirconium, titanium, or hafnium. In many embodiments, M is zirconium. Each of L, Y, and Z may be a nitrogen. Each of $R^1$ and $R^2$ may be —$CH_2$—$CH_2$—. $R^3$ may be hydrogen, and $R^6$ and $R^7$ may be absent.

The Group 15 metal-containing catalyst compound can be represented by the following formula (X).

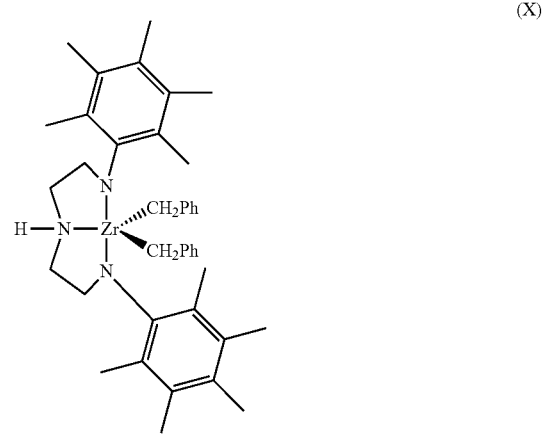

(X)

In formula X, Ph represents phenyl.

Catalyst Slurry

The catalyst system may include a catalyst or catalyst component in a slurry, which may have an initial catalyst compound, and an added solution catalyst component that is added to the slurry. The initial catalyst component slurry may have no catalysts. In this case, two or more solution catalysts may be added to the slurry to cause each to be supported.

Any number of combinations of catalyst components may be used in embodiments. For example, the catalyst component slurry can include an activator and a support, or a supported activator. Further, the slurry can include a catalyst compound in addition to the activator and the support. As noted, the catalyst compound in the slurry may be supported.

The slurry may include one or more activators and supports, and one more catalyst compounds. For example, the slurry may include two or more activators (such as alumoxane and a modified alumoxane) and a catalyst compound, or the slurry may include a supported activator and more than one catalyst compounds. In one embodiment, the slurry includes a support, an activator, and two catalyst compounds. In another embodiment the slurry includes a support, an activator and two different catalyst compounds, which may be added to the slurry separately or in combination. The slurry, containing silica and alumoxane, may be contacted with a catalyst compound, allowed to react, and thereafter the slurry is contacted with another catalyst compound, for example, in a trim system.

The molar ratio of metal in the activator to metal in the pre-catalyst compound in the slurry may be may be 1000:1 to 0.5:1, 300:1 to 1:1, or 150:1 to 1:1. The slurry can include a support material which may be any inert particulate carrier material known in the art, including, but not limited to, silica, fumed silica, alumina, clay, talc or other support materials such as disclosed above. In one embodiment, the slurry contains silica and an activator, such as methyl aluminoxane ("MAO"), modified methyl aluminoxane ("MMAO"), as discussed further below.

One or more diluents or carriers can be used to facilitate the combination of any two or more components of the catalyst system in the slurry or in the trim catalyst solution. For example, the single site catalyst compound and the activator can be combined together in the presence of toluene or another non-reactive hydrocarbon or hydrocarbon mixture to provide the catalyst mixture. In addition to toluene, other suitable diluents can include, but are not limited to, ethylbenzene, xylene, pentane, hexane, heptane, octane, other hydrocarbons, or any combination thereof. The support, either dry or mixed with toluene can then be added to the catalyst mixture or the catalyst/activator mixture can be added to the support.

Catalyst Supports

As used herein, the terms "support" and "carrier" are used interchangeably and refer to any support material, including a porous support material, such as talc, inorganic oxides, and inorganic chlorides. The one or more single site catalyst compounds of the slurry can be supported on the same or separate supports together with the activator, or the activator can be used in an unsupported form, or can be deposited on a support different from the single site catalyst compounds, or any combination thereof. This may be accomplished by any technique commonly used in the art. There are various other methods in the art for supporting a single site catalyst compound. For example, the single site catalyst compound can contain a polymer bound ligand. The single site catalyst compounds of the slurry can be spray dried. The support used with the single site catalyst compound can be functionalized.

The support can be or include one or more inorganic oxides, for example, of Group 2, 3, 4, 5, 13, or 14 elements. The inorganic oxide can include, but is not limited to silica, alumina, titania, zirconia, boria, zinc oxide, magnesia, or any combination thereof. Illustrative combinations of inorganic oxides can include, but are not limited to, alumina-silica, silica-titania, alumina-silica-titania, alumina-zirconia, alumina-titania, and the like. The support can be or include alumina, silica, or a combination thereof. In one embodiment described herein, the support is silica.

Suitable commercially available silica supports can include, but are not limited to, ES757, ES70, and ES70W available from PQ Corporation. Suitable commercially available silica-alumina supports can include, but are not limited to, SIRAL® 1, SIRAL® 5, SIRAL® 10, SIRAL® 20, SIRAL® 28M, SIRAL® 30, and SIRAL® 40, available from SASOL®. Generally, catalysts supports comprising silica gels with activators, such as methylaluminoxanes (MAOs), are used in the trim systems described, since these supports may function better for co-supporting solution carried catalysts. Suitable supports may also be selected from the Cab-o-sil® materials available from Cabot corporation and silica materials available from Grace Davison corporation.

Catalyst supports may also include polymers that are covalently bonded to a ligand on the catalyst. For example, two or more catalyst molecules may be bonded to a single polyolefin chain.

Catalyst Activators

As used herein, the term "activator" may refer to any compound or combination of compounds, supported, or unsupported, which can activate a single site catalyst compound or component, such as by creating a cationic species of the catalyst component. For example, this can include the abstraction of at least one leaving group (the "X" group in the single site catalyst compounds described herein) from the metal center of the single site catalyst compound/component. The activator may also be referred to as a "co-catalyst".

For example, the activator can include a Lewis acid or a non-coordinating ionic activator or ionizing activator, or any other compound including Lewis bases, aluminum alkyls, and/or conventional-type co-catalysts. In addition to methylaluminoxane ("MAO") and modified methylaluminoxane ("MMAO") mentioned above, illustrative activators can include, but are not limited to, aluminoxane or modified aluminoxane, and/or ionizing compounds, neutral or ionic, such as Dimethylanilinium tetrakis(pentafluorophenyl)borate, Triphenylcarbenium tetrakis(pentafluorophenyl)borate, Dimethylanilinium tetrakis(3,5-$(CF_3)_2$phenyl)borate, Triphenylcarbenium tetrakis(3,5-$(CF_3)_2$phenyl)borate, Dimethylanilinium tetrakis(perfluoronapthyl)borate, Triphenylcarbenium tetrakis(perfluoronapthyl)borate, Dimethylanilinium tetrakis(pentafluorophenyl)aluminate, Triphenylcarbenium tetrakis(pentafluorophenyl)aluminate, Dimethylanilinium tetrakis(perfluoronapthyl)aluminate, Triphenylcarbenium tetrakis(perfluoronapthyl)aluminate, a tris(perfluorophenyl) boron, a tris(perfluoronaphthyl)boron, tris(perfluorophenyl) aluminum, a tris(perfluoronaphthyl)aluminum or any combinations thereof.

It is recognized that these activators may or may not bind directly to the support surface or may be modified to allow them to be bound to a support surface while still maintaining their compatibility with the polymerization system. Such tethering agents may be derived from groups that are reactive with surface hydroxyl species. Non-limiting examples of reactive functional groups that can be used to create tethers include aluminum halides, aluminum hydrides, aluminum alkyls, aluminum aryls, sluminum alkoxides, electrophilic silicon reagents, alkoxy silanes, amino silanes, boranes.

Aluminoxanes can be described as oligomeric aluminum compounds having —Al(R)—O— subunits, where R is an alkyl group. Examples of aluminoxanes include, but are not limited to, methylaluminoxane ("MAO"), modified methylaluminoxane ("MMAO"), ethylaluminoxane, isobutylaluminoxane, or a combination thereof. Aluminoxanes can be produced by the hydrolysis of the respective trialkylaluminum compound. MMAO can be produced by the hydrolysis of trimethylaluminum and a higher trialkylaluminum, such as triisobutylaluminum. MMAOs are generally more soluble in aliphatic solvents and more sTable during storage. There are a variety of methods for preparing aluminoxane and modified aluminoxanes.

In one or more embodiments, a visually clear MAO can be used. For example, a cloudy or gelled aluminoxane can be filtered to produce a clear aluminoxane or clear aluminoxane can be decanted from a cloudy aluminoxane solution. In another embodiment, a cloudy and/or gelled aluminoxane can be used. Another aluminoxane can include a modified methyl aluminoxane ("MMAO") type 3A (commercially available from Akzo Chemicals, Inc. under the trade name Modified Methylaluminoxane type 3A). A suitable source of MAO can be a solution having from about 1 wt. % to about a 50 wt. % MAO, for example. Commercially available MAO solutions can include the 10 wt. % and 30 wt. % MAO solutions available from Albemarle Corporation, of Baton Rouge, La.

As noted above, one or more organo-aluminum compounds such as one or more alkylaluminum compounds can be used in conjunction with the aluminoxanes. For example, alkylaluminum species that may be used are diethylaluminum ethoxide, diethylaluminum chloride, and/or diisobutylaluminum hydride. Examples of trialkylaluminum compounds include, but are not limited to, trimethylaluminum, triethylaluminum ("TEAL"), triisobutylaluminum ("TiBAl"), tri-n-hexylaluminum, tri-n-octylaluminum, tripropylaluminum, tributylaluminum, and the like.

Catalyst Component Solutions

The catalyst component solution may include only a catalyst compound or may include an activator in addition to the catalyst compound. The catalyst solution used in the trim process can be prepared by dissolving the catalyst compound and optional activators in a liquid solvent. The liquid solvent may be an alkane, such as a $C_5$ to $C_{30}$ alkane, or a $C_5$ to $C_{10}$ alkane. Cyclic alkanes such as cyclohexane and aromatic compounds such as toluene may also be used. In addition, mineral oil may be used as a solvent. The solution employed should be liquid under the conditions of polymerization and relatively inert. In one embodiment, the liquid utilized in the catalyst compound solution is different from the diluent used in the catalyst component slurry. In another embodiment, the liquid utilized in the catalyst compound solution is the same as the diluent used in the catalyst component solution.

If the catalyst solution includes both activator and catalyst compound, the ratio of metal in the activator to metal, such as aluminum, or metalloid, such as boron, to the metal in the pre-catalyst compound in the solution may be may be 1000:1 to 0.5:1, 300:1 to 1:1, or 150:1 to 1:1. In certain cases, it may be advantageous to have an excess of catalyst compound such that the ratio is <1:1, for example, 1:1 to 0.5:1 or 1:1 to 0.1:1 or 1:1 to 0.01. In various embodiments, the activator and catalyst compound is present in the solution at up to about 90 wt. %, at up to about 50 wt. %, at up to about 20 wt. %, preferably at up to about 10 wt. %, at up to about 5 wt. %, at less than 1 wt. %, or between 100 ppm and 1 wt. %, based upon the weight of the solvent and the activator or catalyst compound.

The catalyst component solution can comprise any one of the soluble catalyst compounds described in the catalyst section herein. As the catalyst is dissolved in the solution, a higher solubility is desirable. Accordingly, the catalyst compound in the catalyst component solution may often include a metallocene, which may have higher solubility than other catalysts.

In the polymerization process, described below, any of the above described catalyst component containing solutions may be combined with any of the catalyst component containing slurry/slurries described above. In addition, more than one catalyst component solution may be utilized.

Continuity Additive/Static Control Agents

In gas-phase polyethylene production processes, as disclosed herein, it may be desirable to additionally use one or more static control agents to aid in regulating static levels in the reactor. As used herein, a static control agent is a chemical composition which, when introduced into a fluidized bed reactor, may influence or drive the static charge (negatively, positively, or to zero) in the fluidized bed. The specific static control agent used may depend upon the nature of the static charge, and the choice of static control agent may vary dependent upon the polymer being produced and the single site catalyst compounds being used.

Control agents such as aluminum stearate may be employed. The static control agent used may be selected for its ability to receive the static charge in the fluidized bed without adversely affecting productivity. Other suitable static control agents may also include aluminum distearate, ethoxlated amines, and anti-static compositions such as those provided by Innospec Inc. under the trade name OCTASTAT. For example, OCTASTAT 2000 is a mixture of a polysulfone copolymer, a polymeric polyamine, and oil-soluble sulfonic acid.

Any of the aforementioned control agents, as well as carboxylate metal salts and including those chemicals and compositions listed as antistatic agents may be employed either alone or in combination as a control agent. For example, the carboxylate metal salt may be combined with an amine containing control agent (e.g., a carboxylate metal salt with any family member belonging to the KEMAMINE® (available from Crompton Corporation) or ATMER® (available from ICI Americas Inc.) family of products).

Other useful continuity additives include ethyleneimine additives useful in embodiments disclosed herein may include polyethyleneimines having the following general formula:

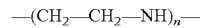

in which n may be from about 10 to about 10,000. The polyethyleneimines may be linear, branched, or hyperbranched (e.g., forming dendritic or arborescent polymer structures). They can be a homopolymer or copolymer of ethyleneimine or mixtures thereof (referred to as polyethyleneimine(s) hereafter). Although linear polymers represented by the chemical formula —[$CH_2$—$CH_2$—NH]— may be used as the polyethyleneimine, materials having primary, secondary, and tertiary branches can also be used. Commercial polyethyleneimine can be a compound having branches of the ethyleneimine polymer. Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF. Another useful continuity additive can include a mixture of aluminum distearate and an ethoxylated amine-type compound, e.g., IRGASTAT AS-990, available from Huntsman (formerly Ciba Specialty Chemicals). The mixture of aluminum distearate and ethoxylated amine type compound can be slurried in mineral oil e.g., Hydrobrite 380. For example, the mixture of aluminum distearate and an ethoxylated amine type compound can be slurried in mineral oil to have total slurry concentration of ranging from about 5 wt. % to about 50 wt. % or about 10 wt. % to about 40 wt. %, or about 15 wt. % to about 30 wt. %.

The continuity additive(s) or static control agent(s) may be added to the reactor in an amount ranging from 0.05 to 200 ppm, based on the weight of all feeds to the reactor, excluding recycle. In some embodiments, the continuity additive may be added in an amount ranging from 2 to 100 ppm, or in an amount ranging from 4 to 50 ppm.

Gas Phase Polymerization Reactor

FIG. 1 is a schematic of a gas-phase reactor system 100, showing the addition of at least two catalysts, at least one of which is added as a trim catalyst. The catalyst component slurry, preferably a mineral oil slurry including at least one support and at least one activator, at least one supported activator, and optional catalyst compounds may be placed in a vessel or catalyst pot (cat pot) 102. In one embodiment, the cat pot 102 is an agitated holding tank designed to keep the solids concentration homogenous. A catalyst component solution, prepared by mixing a solvent and at least one catalyst compound and/or activator, is placed in another vessel, which can be termed a trim pot 104. The catalyst component slurry can then be combined in-line with the catalyst component solution to form a final catalyst composition. A nucleating agent 106, such as silica, alumina, fumed silica or any other particulate matter may be added to the slurry and/or the solution in-line or in the vessels 102 or 104. Similarly, additional activators or catalyst compounds may be added in-line. For example, a second catalyst slurry that includes a different catalyst may be introduced from a second cat pot. The two catalyst slurries may be used as the catalyst system with or without the addition of a solution catalyst from the trim pot.

The catalyst component slurry and solution can be mixed in-line. For example, the solution and slurry may be mixed by utilizing a static mixer 108 or an agitating vessel (not shown). The mixing of the catalyst component slurry and the catalyst component solution should be long enough to allow the catalyst compound in the catalyst component solution to disperse in the catalyst component slurry such that the catalyst component, originally in the solution, migrates to the supported activator originally present in the slurry. The combination forms a uniform dispersion of catalyst compounds on the supported activator forming the catalyst composition. The length of time that the slurry and the solution are contacted is typically up to about 120 minutes, such as about 0.01 to about 60 minutes, about 5 to about 40 minutes, or about 10 to about 30 minutes.

When combining the catalysts, the activator and the optional support or additional cocatalysts, in the hydrocarbon solvents immediately prior to a polymerization reactor it is desirable that the combination yield a new polymerization catalyst in less than 1 h, less than 30 min, or less than 15 min. Shorter times are more effective, as the new catalyst is ready before being introduces into the reactor, providing the potential for faster flow rates.

In another embodiment, an aluminum alkyl, an ethoxylated aluminum alkyl, an aluminoxane, an anti-static agent or a borate activator, such as a $C_1$ to $C_{15}$ alkyl aluminum (for example tri-isobutyl aluminum, trimethyl aluminum or the like), a $C_1$ to $C_{15}$ ethoxylated alkyl aluminum or methyl aluminoxane, ethyl aluminoxane, isobutylaluminoxane, modified aluminoxane or the like are added to the mixture of the slurry and the solution in line. The alkyls, antistatic agents, borate activators and/or aluminoxanes may be added from an alkyl vessel 110 directly to the combination of the solution and the slurry, or may be added via an additional alkane (such as isopentane, hexane, heptane, and or octane) carrier stream, for example, from a hydrocarbon vessel 112. The additional alkyls, antistatic agents, borate activators and/or aluminoxanes may be present at up to about 500 ppm, at about 1 to about 300 ppm, at 10 to about 300 ppm, or at about 10 to about 100 ppm. Carrier streams that may be used include isopentane and or hexane, among others. The carrier may be added to the mixture of the slurry and the solution, typically at a rate of about 0.5 to about 60 lbs/hr (27 kg/hr) or greater, depending on reactor size. Likewise a carrier gas 114, such as nitrogen, argon, ethane, propane and the like, may be added in-line to the mixture of the slurry and the solution. Typically the carrier gas may be added at the rate of about 1 to about 100 lb/hr (0.4 to 45 kg/hr), or about 1 to about 50 lb/hr (5 to 23 kg/hr), or about 1 to about 25 lb/hr (0.4 to 11 kg/hr).

In another embodiment, a liquid carrier stream is introduced into the combination of the solution and slurry that is moving in a downward direction. The mixture of the solution, the slurry and the liquid carrier stream may pass through a mixer or length of tube for mixing before being contacted with a gaseous carrier stream.

Similarly, a comonomer 116, such as hexene, another alpha-olefin or diolefin, may be added in-line to the mixture of the slurry and the solution. The slurry/solution mixture is then passed through an injection tube 118 to a reactor 120. To assist in proper formation of particles in the reactor 120, a nucleating agent 122, such as fumed silica, can be added directly into the reactor 120. In some embodiments, the injection tube may aerosolize the slurry/solution mixture. Any number of suitable tubing sizes and configurations may be used to aerosolize and/or inject the slurry/solution mixture. In one embodiment, a gas stream 124, such as cycle gas, or re-cycle gas 126, monomer, nitrogen, or other materials is introduced into a support tube 128 that surrounds the injection tube 118.

When a metallocene catalyst or other similar catalyst is used in the gas phase reactor, oxygen or fluorobenzene can be added to the reactor 120 directly or to the gas stream 124 to control the polymerization rate. Thus, when a metallocene catalyst (which is sensitive to oxygen or fluorobenzene) is used in combination with another catalyst (that is not sensitive to oxygen) in a gas phase reactor, oxygen can be used to modify the metallocene polymerization rate relative to the polymerization rate of the other catalyst. An example of such a catalyst combination is bis(n-propyl cyclopentadienyl)zirconium dichloride and $[(2,4,6-Me_3C_6H_2)NCH_2CH_2]_2NHZrBn_2$, where Me is methyl or bis(indenyl)zirconium dichloride and $[(2,4,6-Me_3C_6H_2)NCH_2CH_2]_2NHHfBn_2$, where Me is methyl. For example, if the oxygen concentration in the nitrogen feed is altered from 0.1 ppm to 0.5 ppm, significantly less polymer from the bisindenyl $ZrCl_2$ will be produced and the relative amount of polymer produced from the $[(2,4,6-Me_3C_6H_2)NCH_2CH_2]_2NHHfBn_2$ is increased. Water or carbon dioxide may be added to gas phase polymerization reactors, for example, for similar purposes. In one embodiment, the contact temperature of the slurry and the solution is in the range of from 0° C. to about 80° C., from about 0° C. to about 60° C., from about 10° C., to about 50° C. and from about 20° C. to about 40° C.

The example above is not limiting, as additional solutions and slurries may be included. For example, a slurry can be combined with two or more solutions having the same or different catalyst compounds and or activators. Likewise, the solution may be combined with two or more slurries each having the same or different supports, and the same or different catalyst compounds and or activators. Similarly, two or more slurries combined with two or more solutions, preferably in-line, where the slurries each comprise the same or different supports and may comprise the same or different catalyst compounds and or activators and the solutions comprise the same or different catalyst compounds and or activators. For example, the slurry may contain a supported activator and two different catalyst compounds, and two solutions, each containing one of the catalysts in the slurry, are each independently combined, in-line, with the slurry.

Use of Catalyst Composition to Control Product Properties

The properties of the product polymer may be controlled by adjusting the timing, temperature, concentrations, and sequence of the mixing of the solution, the slurry and any optional added materials (nucleating agents, catalyst compounds, activators, etc) described above. The MWD, composition distribution, melt index, relative amount of polymer produced by each catalyst, and other properties of the polymer produced may also be changed by manipulating process parameters. Any number of process parameters may be adjusted, including manipulating hydrogen concentration in the polymerization system, changing the amount of the first catalyst in the polymerization system, changing the amount of the second catalyst in the polymerization system. Other process parameters that can be adjusted include changing the relative ratio of the catalyst in the polymerization process (and optionally adjusting their individual feed rates to maintain a steady or constant resin production rate). The concentrations of reactants in the reactor 120 can be adjusted by changing the amount of liquid or gas that is withdrawn or purged from the process, changing the amount and/or composition of a recovered liquid and/or recovered gas returned to the polymerization process, wherein the recovered liquid or recovered gas can be recovered from polymer discharged from the polymerization process. Further concentration parameters that can be adjusted include changing the polymerization temperature, changing the ethylene partial pressure in the polymerization process, changing the ethylene to comonomer ratio in the polymerization process, changing the activator to transition metal ratio in the activation sequence. Time dependant parameters may be adjusted, such as changing the relative feed rates of the slurry or solution, changing the mixing time, the temperature and or degree of mixing of the slurry and the solution in-line, adding different types of activator compounds to the polymerization process, and adding oxygen or fluorobenzene or other catalyst poison to the polymerization process. Any combinations of these adjustments may be used to control the properties of the final polymer product.

In one embodiment, the composition distribution of the polymer product is measured at regular intervals and one of the above process parameters, such as temperature, catalyst compound feed rate, the ratio of the two or more catalysts to each other, the ratio of comonomer to monomer, the monomer partial pressure, and or hydrogen concentration, is altered to bring the composition to the desired level, if necessary. The composition distribution may be performed by temperature rising elution fractionation (TREF), or similar techniques TREF measures composition as a function of elution temperature.

In one embodiment, a polymer product property is measured in-line and in response the ratio of the catalysts being combined is altered. In one embodiment, the molar ratio of the catalyst compound in the catalyst component slurry to the catalyst compound in the catalyst component solution, after the slurry and solution have been mixed to form the final catalyst composition, is 500:1 to 1:500, or 100:1 to 1:100, or 50:1 to 1:50, or 10:1 to 1:10, or 5:1 to 1:5. In another embodiment, the molar ratio of a Group 15 catalyst compound in the slurry to a ligand metallocene catalyst compound in the solution, after the slurry and solution have been mixed to form the catalyst composition, is 500:1, 100:1, 50:1, 10:1, 5:1, 1:5, 1:10, 1:100, or 1:500. The product property measured can include the polymer product's flow index, melt index, density, MWD, comonomer content, composition distribution, and combinations thereof. In another embodiment, when the ratio of the catalyst compounds is altered, the introduction rate of the catalyst composition to the reactor, or other process parameters, is altered to maintain a desired production rate.

While not wishing to be bound by or limited to any theory, it is believed that the processes described herein immobilize the solution catalyst compound in and on a support, preferably a supported activator. The in-line immobilization techniques described herein preferably result in a supported catalyst system that when introduced to the reactor provides for suitable polymer properties, with appropriate particle morphology, bulk density, or higher catalyst activities and without the need for additional equipment in order to introduce catalyst compound solution into a reactor, particularly a gas phase or slurry phase reactor.

Polymerization Process

The catalyst system can be used to polymerize one or more olefins to provide one or more polymer products therefrom. Any suitable polymerization process can be used, including, but not limited to, high pressure, solution, slurry, and/or gas phase polymerization processes. In embodiments that use other techniques besides gas phase polymerization, modifications to a catalyst addition system that are similar to those discussed with respect to FIG. 1 can be used. For example, a trim system may be used to feed catalyst to a loop slurry reactor for polyethylene copolymer production.

The terms "polyethylene" and "polyethylene copolymer" refer to a polymer having at least 50 wt. % ethylene-derived units. In various embodiments, the polyethylene can have at least 70 wt. % ethylene-derived units, at least 80 wt. % ethylene-derived units, at least 90 wt. % ethylene-derived units, at least 95 wt. % ethylene-derived units, or 100 wt. % ethylene-derived units. The polyethylene can, thus, be a homopolymer or a copolymer, including a terpolymer, having one or more other monomeric units. As described herein, a polyethylene can include, for example, at least one or more other olefins or comonomers. Suitable comonomers can contain 3 to 16 carbon atoms, from 3 to 12 carbon atoms, from 4 to 10 carbon atoms, and from 4 to 8 carbon atoms. Examples of comonomers include, but are not limited to, propylene, 1-butene, 1-pentene, 1-hexene, 1-heptene, 1-octene, 4-methylpent-1-ene, 1-decene, 1-dodecene, 1-hexadecene, and the like. Additionally, small amounts of diene monomers, such as 1,7-octadiene may be added to the polymerization to adjust polymer properties.

Referring again to FIG. 1, the fluidized bed reactor 120 can include a reaction zone 130 and a velocity reduction zone 132. The reaction zone 130 can include a bed 134 that includes growing polymer particles, formed polymer particles and a minor amount of catalyst particles fluidized by the continuous flow of the gaseous monomer and diluent to remove heat of polymerization through the reaction zone. Optionally, some of the re-circulated gases 126 can be cooled and compressed to form liquids that increase the heat removal capacity of the circulating gas stream when readmitted to the reaction zone. A suitable rate of gas flow can be readily determined by experimentation. Make-up of gaseous monomer to the circulating gas stream can be at a rate equal to the rate at which particulate polymer product and monomer associated therewith is withdrawn from the reactor and the composition of the gas passing through the reactor can be adjusted to maintain an essentially steady state gaseous composition within the reaction zone. The gas leaving the reaction zone 130 can be passed to the velocity reduction zone 132 where entrained particles are removed, for example, by slowing and falling back to the reaction zone 130. If desired, finer entrained particles and dust can be removed in a separation system 136, such as a cyclone and/or fines filter. The gas 126 can be passed through a heat exchanger 138 where at least a portion of the heat of polymerization can be removed. The gas can then be compressed in a compressor 140 and returned to the reaction zone 130.

The reactor temperature of the fluid bed process can be greater than about 30° C., about 40° C., about 50° C., about 90° C., about 100° C., about 110° C., about 120° C., about 150° C., or higher. In general, the reactor temperature is operated at the highest feasible temperature taking into account the sintering temperature of the polymer product within the reactor. Preferred reactor temperatures are between 70 and 95° C. More preferred reactor temperatures are between 75 and 90° C. Thus, the upper temperature limit in one embodiment is the melting temperature of the polyethylene copolymer produced in the reactor. However, higher temperatures may result in narrower MWDs, which can be improved by the addition of the MCN, or other, co-catalysts, as described herein.

Hydrogen gas can be used in olefin polymerization to control the final properties of the polyolefin. Using certain catalyst systems, increasing concentrations (partial pressures) of hydrogen can increase the flow index (FI) of the polyethylene copolymer generated. The flow index can thus be influenced by the hydrogen concentration. The amount of hydrogen in the polymerization can be expressed as a mole ratio relative to the total polymerizable monomer, for example, ethylene, or a blend of ethylene and hexene or propylene.

The amount of hydrogen used in the polymerization process can be an amount necessary to achieve the desired flow index of the final polyolefin resin. For example, the mole ratio of hydrogen to total monomer ($H_2$:monomer) can be greater than about 0.0001, greater than about 0.0005, or greater than about 0.001. Further, the mole ratio of hydrogen to total monomer ($H_2$:monomer) can be less than about 10, less than about 5, less than about 3, and less than about 0.10. A desirable range for the mole ratio of hydrogen to monomer can include any combination of any upper mole ratio limit with any lower mole ratio limit described herein. Expressed another way, the amount of hydrogen in the reactor at any time can range to up to about 5,000 ppm, up to about 4,000 ppm in another embodiment, up to about 3,000 ppm, or between about 50 ppm and 5,000 ppm, or between about 50 ppm and 2,000 ppm in another embodiment. The amount of hydrogen in the reactor can range from a low of about 1 ppm, about 50 ppm, or about 100 ppm to a high of about 400 ppm, about 800 ppm, about 1,000 ppm, about 1,500 ppm, or about 2,000 ppm. Further, the ratio of hydrogen to total monomer ($H_2$:monomer) can be about 0.00001:1 to about 2:1, about 0.005:1 to about 1.5:1, or about 0.0001:1 to about 1:1. The one or more reactor pressures in a gas phase process (either single stage or two or more stages) can vary from 690 kPa (100 psig) to 3,448 kPa (500 psig), in the range from 1,379 kPa (200 psig) to 2,759 kPa (400 psig), or in the range from 1,724 kPa (250 psig) to 2,414 kPa (350 psig).

The gas phase reactor can be capable of producing from about 10 kg of polymer per hour (25 lbs/hr) to about 90,900 kg/hr (200,000 lbs/hr), or greater, and greater than about 455 kg/hr (1,000 lbs/hr), greater than about 4,540 kg/hr (10,000 lbs/hr), greater than about 11,300 kg/hr (25,000 lbs/hr), greater than about 15,900 kg/hr (35,000 lbs/hr), and greater than about 22,700 kg/hr (50,000 lbs/hr), and from about 29,000 kg/hr (65,000 lbs/hr) to about 45,500 kg/hr (100,000 lbs/hr).

As noted, a slurry polymerization process can also be used in embodiments. A slurry polymerization process generally uses pressures in the range of from about 101 kPa (1 atmosphere) to about 5,070 kPa (50 atmospheres) or greater, and temperatures in the range of from about 0° C. to about 120° C., and more particularly from about 30° C. to about 100° C. In a slurry polymerization, a suspension of solid, particulate polymer can be formed in a liquid polymerization diluent medium to which ethylene, comonomers, and hydrogen along with catalyst can be added. The suspension including diluent can be intermittently or continuously removed from the reactor where the volatile components are separated from the polymer and recycled, optionally after a distillation, to the reactor. The liquid diluent employed in the polymerization medium can be an alkane having from 3 to 7 carbon atoms, such as, for example, a branched alkane. The medium employed should be liquid under the conditions of polymerization and relatively inert. When a propane medium is used the process should be operated above the reaction diluent critical temperature and pressure. In one embodiment, a hexane, isopentane, or isobutane medium can be employed. The slurry can be circulated in a continuous loop system.

The product polyethylene can have a melt index ratio (MIR or $I_{21}/I_2$) ranging from about 5 to about 300, or from about 10 to less than about 150, or, in many embodiments, from about 15 to about 50. Flow index (FI, HLMI, or $I_{21}$ can be measured in accordance with ASTM D1238 (190° C., 21.6 kg). The melt index (MI, $I_2$) can be measured in accordance with ASTM D1238 (at 190° C., 2.16 kg weight).

Density can be determined in accordance with ASTM D-792. Density is expressed as grams per cubic centimeter ($g/cm^3$) unless otherwise noted. The polyethylene can have a density ranging from a low of about 0.89 $g/cm^3$, about 0.90 $g/cm^3$, or about 0.91 $g/cm^3$ to a high of about 0.95 $g/cm^3$, about 0.96 $g/cm^3$, or about 0.97 $g/cm^3$. The polyethylene can have a bulk density, measured in accordance with ASTM D1895 method B, of from about 0.25 $g/cm^3$ to about 0.5 $g/cm^3$. For example, the bulk density of the polyethylene can range from a low of about 0.30 $g/cm^3$, about 0.32 $g/cm^3$, or about 0.33 $g/cm^3$ to a high of about 0.40 $g/cm^3$, about 0.44 $g/cm^3$, or about 0.48 $g/cm^3$.

The polyethylene can be suitable for such articles as films, fibers, nonwoven and/or woven fabrics, extruded articles, and/or molded articles. Examples of films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Examples of fibers include melt spinning, solution spinning and melt blown fiber operations for use in woven or non-woven form to make filters, diaper fabrics, hygiene products, medical garments, geotextiles, etc. Examples of extruded articles include tubing, medical tubing, wire and cable coatings, pipe, geomembranes, and pond liners. Examples of molded articles include single and multi-layered constructions in the form of bottles, tanks, large hollow articles, rigid food containers and toys, etc.

EXAMPLES

To provide a better understanding of the foregoing discussion, the following non-limiting examples are provided. All parts, proportions, and percentages are by weight unless otherwise indicated.

As described herein, comonomer, such as a $C_4$-$C_8$ alpha-olefin is added to a reaction, along with ethylene monomer, to create short chain branching (SCB) in polyethylene copolymers. Without intending to be being limited by theory, the SCB may cause a long PE chain to break free from a crystallite and be partly incorporated into other crystallites. Accordingly, polymers that have SCB on longer chains may exhibit higher toughness.

In contrast, long chain branching (LCB) are points at which two polymer chains may divide off from single polymer chains. LCB may enhance toughness, but cause the polymer to more vulnerable to orientation, causing lower tear strength in the direction of extrusion.

Hydrogen may be added to the polymer reactions to control molecular weight. The hydrogen acts as chain termination agent, essentially replacing a monomer or comonomer molecule in the reaction. This stops the formation of a current polymer chain, and allows a new polymer chain to begin.

Catalyst System Comonomer Incorporation Versus MWD Control, Results from Six Inch Gas Phase Reactor Polymerization Experiments in 6 Inch Diameter Gas-Phase Reactor The catalysts A-J shown in Table 1 were prepared as described herein. All the catalysts prepared were screened in a fluidized bed reactor equipped with devices for temperature control, catalyst feeding or injection equipment, gas chromatograph (GC) analyzer for monitoring and controlling monomer and comonomer gas feeds and equipment for polymer sampling and collecting. The reactor consisted of a 6 inch (15.24 cm) diameter bed section increasing to 10 inches (25.4 cm) at the reactor top. Gas comes in through a perforated distributor plate allowing fluidization of the bed contents and polymer sample is discharged at the reactor top. The comonomer in the example polymerizations herein is 1-hexene. The polymerization parameters are outlined in the Table 1 below and plotted in FIGS. 2 and 3.

The reacting bed of growing polymer particles was maintained in a fluidized state by continually flowing the makeup feed and recycle gas through the reaction zone at a superficial gas velocity 1-2 ft/sec (0.3 to 0.6 m/sec). The reactor was operated at a temperature of 175 F (79 C) and total pressure of 300 psig (2274 kPa gauge) including 35 mol % ethylene.

phase reactor (LGPR) described herein. The left axis 202 represents the gas-phase ratios of hydrogen to ethylene monomer ($H_2/C_2$) used to achieve the target properties, in units of parts-per-million (mol) of $H_2$ per mol % $C_2$ (ppm/mol %). The right axis 204 represents the comonomer to ethylene ratio ($C_6/C_2$) used to achieve the target properties, in units of mol per mol.

Comparing $C_6/C_2$ levels used to achieve the property targets indicate the relative abilities of the catalysts to incorporate comonomer. For example, comparing the $C_6/C_2$ level 206 for $(1\text{-EtInd})_2ZrCl_2$ (B) to the $C_6/C_2$ level 208 for $(PrCp)_2HfF_2$ (I) gives a ratio of about 36/9 or about four. This indicates that for a given $C_6/C_2$ gas ratio, a polymer prepared with $(PrCp)_2HfF_2$ will have approximately four times the short chain branching (SCB) of a polymer prepared using $(1\text{-EtInd})_2ZrCl_2$. This data is useful for controlling composition distributions of polymers made as in-situ blends using catalyst mixtures, for example, as co-supported catalysts on a single support. The data is also useful for determining which catalysts should be combined to have a composition distribution containing both comonomer rich (low density) and comonomer poor (high density) components.

The effects of the steady state gas ratios for $H_2/C_2$ (ppm/mol) 202 are shown by the bars. The levels of these bars roughly indicate the relative molecular weight capabilities of the catalysts. For example, $(CH_2)_3Si(CpMe_4)CpZrCl_2$ (J) requires a $H_2/C_2$ ratio 210 of about 23.4 ppm/mol to achieve a target melt index of about one, and $(CpMe_5)(1\text{-MeInd})ZrCl_2$ (A) requires a $H_2/C_2$ ratio 212 of about 0.4 ppm/mol to achieve the same target melt index. These results indicate that $(CH_2)_3Si(CpMe_4)CpZrCl_2$ (J) yields a higher Mw polymer than $(CpMe_5)(1\text{-MeInd})ZrCl_2$ (A) at the same $H_2/C_2$ ratio. In this example, the data is approximate since the change in Mw is not measured as a function of $H_2/C_2$.

Figure 2:
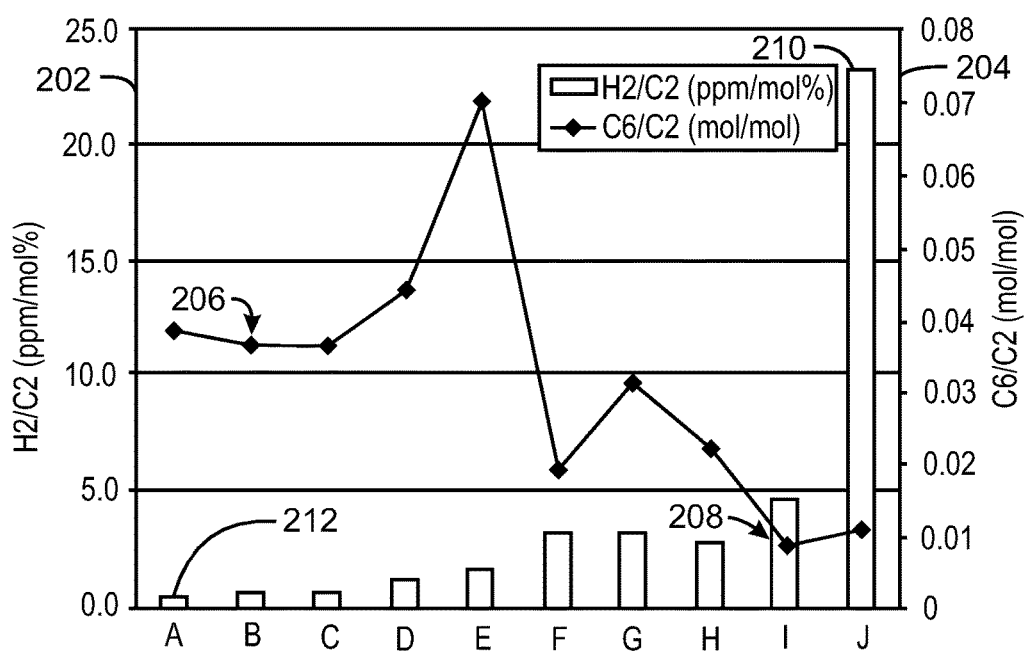
FIG. 2 is a plot of a series of polymers that were prepared to test the relative abilities of a series of metallocene catalysts to prepare a resin having about a 1 melt index (MI) and a density (D) of about 0.92.
Figure 3:
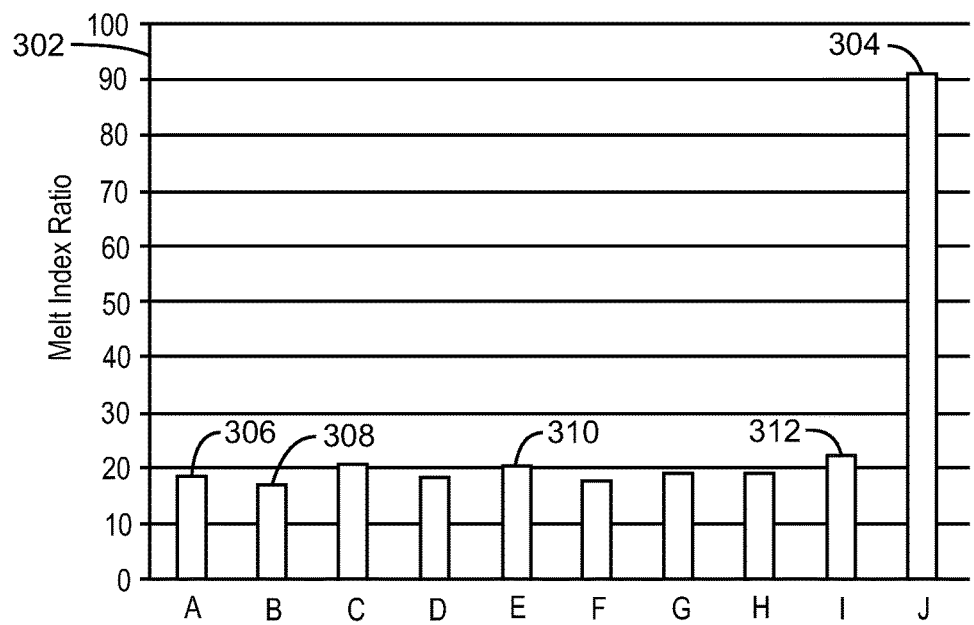
FIG. 3 is a plot of the series of polymers of FIG. 2, showing the melt index ratio (MIR) of the series of polymers made by different metallocene (MCN) catalysts.

FIG. 3 is a plot 300 of the series of polymers of FIG. 2, showing the melt index ratio (MIR) of the series of polymers made by different metallocene (MCN) catalysts. As used herein, the terms melt index ratio (MIR), melt flow ratio (MFR), and "$I_{21}/I_2$," interchangeably refer to the ratio of the flow index ("FI" or "$I_{21}$") to the melt index ("MI" or "$I_2$"). The MI ($I_2$) can be measured in accordance with ASTM D1238 (at 190° C., 2.16 kg weight). The FI ($I_{21}$) can be

TABLE 1

Polymerization Experiments in 6 Inch Diameter Gas-Phase Reactor

| | Metallocene | C6/C2 Feed ratio (g/g) | [H2]/C2 (ppm/mol %) | C6/C2 (mol/mol) | Density (g/mL) | MI = I2 (g/10 min) | MIR (I21/I2) |
|---|---|---|---|---|---|---|---|
| A | $(CpMe_5)(1\text{-MeInd})ZrCl_2$ | 0.096 | 0.4 | 0.038 | 0.928 | 1.84 | 18.5 |
| B | $(1\text{-EtInd})_2ZrCl_2$ | 0.115 | 0.7 | 0.036 | 0.923 | 2.58 | 17.2 |
| C | $(Me_4Cp)_1\text{-MeIndZrCl}_2$ | 0.104 | 0.7 | 0.036 | 0.922 | 1.05 | 20.5 |
| D | $(1\text{-MeInd})_2ZrCl_2$ | 0.132 | 1.2 | 0.044 | 0.92 | 1.62 | 18.3 |
| E | $(Me_4Cp)(1,3\text{-Me}_2Ind)ZrCl_2$ | 0.151 | 1.7 | 0.07 | 0.921 | 1.19 | 20.1 |
| F | $(1\text{-Bu, 3-MeCp})ZrCl_2$ | 0.086 | 3.3 | 0.019 | 0.917 | 1.1 | 17.4 |
| G | $(Me_4PrCp)MeCpZrCl_2$ | 0.094 | 3.4 | 0.031 | 0.918 | 1.1 | 18.5 |
| H | $(Me_4Cp)PrCpZrCl_2$ | 0.083 | 3.0 | 0.022 | 0.919 | 0.95 | 18.6 |
| I | $(PrCp)_2HfF_2$ | 0.078 | 4.8 | 0.009 | 0.917 | 0.79 | 21.8 |
| J | $(CH2)_3Si(CpMe_4)CpZrCl_2$ | 0.083 | 23.4 | 0.011 | 0.92 | 0.66 | 90.3 |

FIG. 2 is a plot 200 of a series of polymers that were prepared to test the relative abilities of a series of metallocene catalysts to prepare a resin having about a 1 melt index (MI) and a density (D) of about 0.92. The polymerizations were performed in the six inch diameter continuous gas measured in accordance with ASTM D1238 (at 190° C., 21.6 kg weight). Like numbered items are as described with respect to FIG. 2. In this plot 300, the left axis 302 represents the MIR. The MIR (which may also be termed melt flow ratio or MFR) is the ratio of the I21 and I2 melt indices and may indicate the presence of long chain branching. For linear resins, without LCB, the ratio is around 25 or less. Higher MIR values may indicate the presence of LCB which can be detrimental to film properties, as noted above. The highest MIR ratio 304 was for $(CH_2)_3Si(CpMe_4)CpZrCl_2$ (J), indicating that polymer produced by this catalyst has the most LCB. In contrast, blending resins for with the two different catalysts forms a final product that will have a higher MIR.

Using the results shown in FIGS. 2 and 3, five catalysts were selected to determine the dependence of the weight average molecular weight (Mw) on the $H_2$ ratio. These catalysts included three catalysts that generate lower Mw polyethylene, $(CpMe_5)(1-MeInd)ZrCl_2$ (A) 306, $(1-EtInd)_2ZrCl_2$ (B) 308, and $(Me_4Cp)(1,3-Me_2Ind)ZrCl_2$ (E) 310. The catalysts also included a catalyst that generates a middle Mw polyethylene, $(PrCp)_2HfF_2$ (I) 312. Table 2 contains data on the dependence of Mw on $H_2/C_2$ level.

TABLE 2

Mw vs. $H_2/C_2$ level for selected MCNs

| Run No | Catalyst | $H_2/C_2$ (ppm/mol) | Mw | Mw/Mn | 1/Mw |
|---|---|---|---|---|---|
| 1 | $(CpMe_5)1$-MeIndZrCl$_2$ | 0.2 | 186,862 | 3.27 | 5.3515E–06 |
| 2 | $(CpMe_5)1$-MeIndZrCl$_2$ | 4.3 | 60,228 | 4.65 | 1.6604E–05 |
| 3 | $(CpMe_5)1$-MeIndZrCl$_2$ | 6.3 | 48,140 | 5.58 | 2.0773E–05 |
| 4 | $(1-EtInd)_2ZrCl_2$ | 0.5 | 125,656 | 3.18 | 7.9582E–06 |
| 5 | $(1-EtInd)_2ZrCl_2$ | 4.2 | 47,275 | 4.34 | 2.1153E–05 |
| 6 | $(Me_4Cp)(1,3-Me_2Ind)ZrCl_2$ | 0.3 | 167,546 | 4.31 | 5.9685E–06 |
| 7 | $(Me_4Cp)(1,3-Me_2Ind)ZrCl_2$ | 4.3 | 72,602 | 3.85 | 1.3774E–05 |
| 8 | $(PrCp)_2HfF_2$ | 2.0 | 193,086 | 2.82 | 5.1790E–06 |
| 9 | $(PrCp)_2HfF_2$ | 4.8 | 132,536 | 2.81 | 7.5451E–06 |
| 10 | $(PrCp)_2HfF_2$ | 10.2 | 63,030 | 2.98 | 1.5865E–05 |

These results were used to generate a series of plots that can be used to determine the sensitivity of the Mw to $H_2/C_2$ ratios. Table 3 indicates the slope and intercepts of the reciprocal plots. The lower Mw catalysts had larger slopes, indicating a greater influence of $H_2/C_2$ ratios on Mw. The second catalyst, $(1-EtInd)_2ZrMe_2$, had the greatest dependence of Mw on $H_2/C_2$ ratio. The slopes may be used to select catalysts having widely divergent responses to hydrogen.

The data presented in FIGS. 2 and 3 and Tables 2 and 3 indicate that a combination of $(1-EtInd)_2ZrCl_2$ (B) and $(PrCp)_2HfF_2$ (I) will give a polymer with a broad MWD and SCBD without LCB. As shown in the plot 300 in FIG. 3, the resins made with these two catalysts have MIR near 20 and, thus, are essentially free of LCB. The information in Tables 2 and 3 indicate that $(1-EtInd)_2ZrCl_2$ has approximately one third the Mw of $(PrCp)_2HfF_2$ at around 4.2 ppm/mol $H_2/C_2$. The information in the plot 200 shown in FIG. 2, indicates that $(1-EtInd)_2ZrCl_2$ has approximately one fourth the SCB of $(PrCp)_2HfF_2$ under comparable conditions.

TABLE 3

Slope and intercept for plots of $H_2/C_2$ vs. 1/Mw for selected MCNs

| | Catalyst | slope | intercept |
|---|---|---|---|
| 1 | $(CpMe_5)1$-MeIndZrCl$_2$ | 2.576E–06 | 4.932E–06 |
| 2 | $(1-EtInd)_2ZrCl_2$ | 3.533E–06 | 6.245E–06 |
| 3 | $(Me_4Cp)(1,3-Me_2Ind)ZrCl_2$ | 1.945E–06 | 5.436E–06 |
| 4 | $(PrCp)_2HfF_2$ | 1.342E–06 | 1.929E–06 |

The equations from Table 3 can be used to predict the amounts of $(1-EtInd)_2ZrCl_2$ needed in a combination with the catalyst $(PrCp)_2HfF_2$ to make an overall resin with Mw of 100 Kg/mol at four different $H_2$ levels. These values may be used to set initial control points, for example, if $(PrCp)_2HfF_2$ is used as a supported catalyst component, and $(1-EtInd)_2ZrCl_2$ is a solution catalyst component, to be added as a trim catalyst. In this embodiment, the amount of the $(1-EtInd)_2ZrCl_2$ catalyst that is added may be controlled to achieve Mw and other performance targets. Results for various combinations are shown in Table 4.

TABLE 4

Mw of $(1-EtInd)_2ZrCl_2$ (lmw) and $(PrCp)_2HfF_2$ (hmw) as a function of $H_2/C_2$ and fraction of low Mw polymer (F lmw) necessary to make an overall Mw 100 Kg/mol

| $H_2/C_2$ | lmw | hmw/lmw | hmw | F lmw |
|---|---|---|---|---|
| 4 | 49072 | 2.8 | 137020 | 0.42 |
| 4.5 | 45157 | 2.8 | 125480 | 0.32 |
| 5 | 41821 | 2.8 | 115733 | 0.21 |
| 5.5 | 38944 | 2.8 | 107391 | 0.11 |

Pilot Plant Runs using Trim Feed

The use of a catalyst trim feed to control the molecular weight and molecular weight distribution was tested in a pilot plant, with the results detailed in Table 5. In Table 5, the catalyst type corresponds to the numbered catalyst structures shown in the detailed description. Five of the catalyst runs (A-E) were control runs performed without the use of a trim catalyst.

TABLE 5

Results from 13.25 Inch pilot plant reactor using trim addition.

| Run No | Catalyst Type | Catalyst Form - Dry/Slurry | Catalyst Support | Al/Hf Catalyst Mole Ratio | Trim Catalyst Type | H2/C2 Conc Ratio (ppm/m %) |
|---|---|---|---|---|---|---|
| A | III | Dry | | 98.6 | None | 6.03 |
| B | III | Dry | | 98.6 | None | 5.81 |
| C | III | Slurry | Spray Dried | 234 | None | 4.65 |
| 1 | III | Slurry | Spray Dried | 234 | None | 3.87 |
| 2 | III | Slurry | Spray Dried | 234 | IV-A, IV-B | 3.79 |
| 3 | III | Slurry | Spray Dried | 234 | IV-A, IV-B | 3.78 |

TABLE 5-continued

Results from 13.25 Inch pilot plant reactor using trim addition.

| | | | | | | |
|---|---|---|---|---|---|---|
| 4 | III | Slurry | Spray Dried | 234 | IV-C | 3.81 |
| 5 | III | Slurry | Spray Dried | 234 | IV-C | 3.80 |
| 6 | III | Slurry | Spray Dried | 234 | IV-D | 3.83 |
| 7 | III | Slurry | Spray Dried | 234 | IV-D | 3.79 |
| 8 | III | Slurry | Spray Dried | 234 | V-A | 3.80 |
| 9 | III | Slurry | Spray Dried | 234 | V-A | 3.79 |
| D | III | Slurry | Spray Dried | 234 | None | 24.98 |
| E | III | Slurry | Spray Dried | 234 | None | 20.04 |
| 10 | III | Slurry | Spray Dried | 234 | V-B | 20.01 |
| 11 | III | Slurry | Spray Dried | 234 | V-B | 20.12 |
| 12 | III | Slurry | Spray Dried | 234 | IV-A, IV-B | 3.60 |
| 13 | III | Slurry | Spray Dried | 234 | IV-A, IV-B | 3.81 |

| Run No | C6/C2 Conc Ratio (m/m) | Melt Index (dg/min) | High Load Melt Index (dg/min) | MIR (HLMI/MI) | Density (g/cc) | Cat Prod. |
|---|---|---|---|---|---|---|
| A | 0.016352 | 1.21 | 41.8 | 34 | 0.9180 | 13,239 |
| B | 0.014848 | 1.45 | 32.8 | 23 | 0.9168 | 13,071 |
| C | 0.01527 | 0.73 | 18.2 | 25.0 | 0.9201 | 7,801 |
| 1 | 0.01539 | 0.49 | 11.7 | 23.9 | 0.9194 | 7,373 |
| 2 | 0.01835 | 1.68 | 83.2 | 49.4 | 0.9340 | 9,956 |
| 3 | 0.01729 | 1.01 | 37.0 | 36.6 | 0.9281 | 8,300 |
| 4 | 0.01742 | 1.23 | 35.9 | 29.1 | 0.9274 | 8,233 |
| 5 | 0.01823 | 1.72 | 57.0 | 33.1 | 0.9315 | 8,767 |
| 6 | 0.01614 | 0.914 | 21.3 | 23.3 | 0.9221 | 8,267 |
| 7 | 0.01709 | 1.090 | 27.8 | 25.5 | 0.9238 | 7,680 |
| 8 | 0.01595 | 0.602 | 14.6 | 24.3 | 0.9201 | 8,178 |
| 9 | 0.01724 | 0.702 | 19.0 | 27.1 | 0.9234 | 7,233 |
| D | 0.00364 | 640 | 6866 | 10.7 | 0.9546 | 6,222 |
| E | 0.00388 | 399 | 6443 | 16.1 | 0.9543 | 7,726 |
| 10 | 0.00409 | 86.3 | 2924 | 33.9 | 0.9501 | 3,988 |
| 11 | 0.01386 | 28.2 | 1325 | 47.0 | 0.9406 | 3,903 |
| 12 | 0.01692 | 0.401 | 13.4 | 33.5 | 0.9232 | 11,076 |
| 13 | 0.01953 | 0.287 | 10.8 | 37.8 | 0.9206 | 11,200 |

Controlling molecular weight distribution and composition distribution using co-supported catalysts in combination with $(CpPr)_2HfF_2$.

Tests were run using a primary catalyst that included $(CpPr)_2HfMe_2$ (HfP, structure III). HfP is capable of polymerizing ethylene and mixtures of ethylene and comonomers in the presence of an activator and a support, a cocatalyst, or both. The activator and support may be the same or different. Multiple activators, supports and or cocatalysts may be used simultaneously. Cocatalysts may be added to modify any of the ingredients. The descriptor catalyst, HfP, activator, supports and or cocatalysts refers to the actual compounds and also solutions of these compounds in hydrocarbon solvents.

For use as cocatalysts, especially in trim systems, the catalysts should be soluble in alkane solvents such as hexane, paraffinic solvents, and mineral oil. The solubility may be greater than 0.0001 wt. %, greater than 0.01 wt. %, greater than 1 wt. %, or greater than 2%. Toluene may also be used as a solvent as the catalyst may be more soluble in an aromatic solvent As described herein, a combination of HfP, an activator (MAO), and a support (silica) was reacted with trim catalysts in hydrocarbon solvents to yield a polymerization catalyst with a different polymerization behavior than expected from the combination of the individual components. More specifically, the molecular weight distribution for a polymer generated by the co-supported co-catalysts is broader than can be achieved by mixtures of polymers formed from the individual component catalysts. This change in polymerization behavior is exemplified by changes in the MWD, the CD, or MWD and CD of polymers formed by the mixture of HfP and the selected cocatalysts. Thus, combining catalysts, HfP, activator and optionally a support, additional cocatalysts, or both, in hydrocarbon solvents in an in-line mixer immediately prior to a polymerization reactor yields a new polymerization catalyst.

Any sequence of the combination of catalysts, HfP, activator and optionally a support, additional cocatalysts, or both, in hydrocarbon solvents may be used. For example, the catalysts may be added to a mixture that includes HfP, activator and optionally a support, additional cocatalysts, or both. Further, catalysts and cocatalysts may be added to a mixture of {HfP, activator and optionally a support}. In addition, catalysts and HfP may be added to a mixture that includes {activator and optionally a support and cocatalysts}.

It is desirable to combine the catalysts, HfP, the activator and optionally a support, additional cocatalysts or both, in hydrocarbon solvents then obtain a dry catalyst from the mixture. This dry mixture may be fed directly, or as a slurry, into a polymerization reactor.

The change in the MWD and CD upon using the catalysts and HfP can be controlled by changing the ratio of the catalysts to HfP. When no catalysts are employed, the MWD and CD is that of HfP. When single catalysts are employed, the MWD and CD is that generated by the catalysts themselves. Changing the ratio of catalysts changes the MWD and CD from that of the parents. The ratio can be changed to target specific MWD and CD targets.

Catalysts can be chosen to control the change in MWD or CD of the polymer formed. Employing catalysts that yield lower or higher molecular weight polymers than HfP will broaden the molecular weight distribution. The response of the Mw of polymers made from the single components versus H2/C2 can be used as a guide for the selection. For example, a catalyst having less response to hydrogen than HfP will yield a higher Mw than a polymer produced by HfP by itself, as shown in FIG. 2. Further, a catalyst having a higher response to hydrogen than HfP will, in a combination with HfP, yield a lower Mw than HfP by itself.

In addition to selecting catalysts to broaden the MWD, catalysts may be selected to change the composition distribution. For example, employing catalysts that incorporate less or more comonomer than HfP will broaden the composition distribution. A rough guide to this effect, as discussed further below, is the relative gas C6/C2 ratios required to prepare an approximately 0.92 D resin from different catalysts. Those catalysts that give larger differences in C6/C2 gas ratios from HfP will broaden the CD more. Molecular weight distributions can also be changed by employing a catalyst that yields a different MWD but similar average molecular weight to that from HfP.

The combination of catalysts with HfP can yield a MWD that is larger than expected from the theoretical combination of the individual catalysts. Desirable materials based on an HfP base catalyst are made when the Mw and comonomer incorporation abilities of the catalysts are both higher than HfP. Similarly, desirable materials are also formed when the Mw and comonomer incorporation abilities of the catalysts are both lower than HfP. Further, desirable materials are made when the Mw and of the catalysts are similar to and the comonomer incorporation abilities lower than HfP.

Making a Co-Supported Polymerization Catalyst

Figure 4:
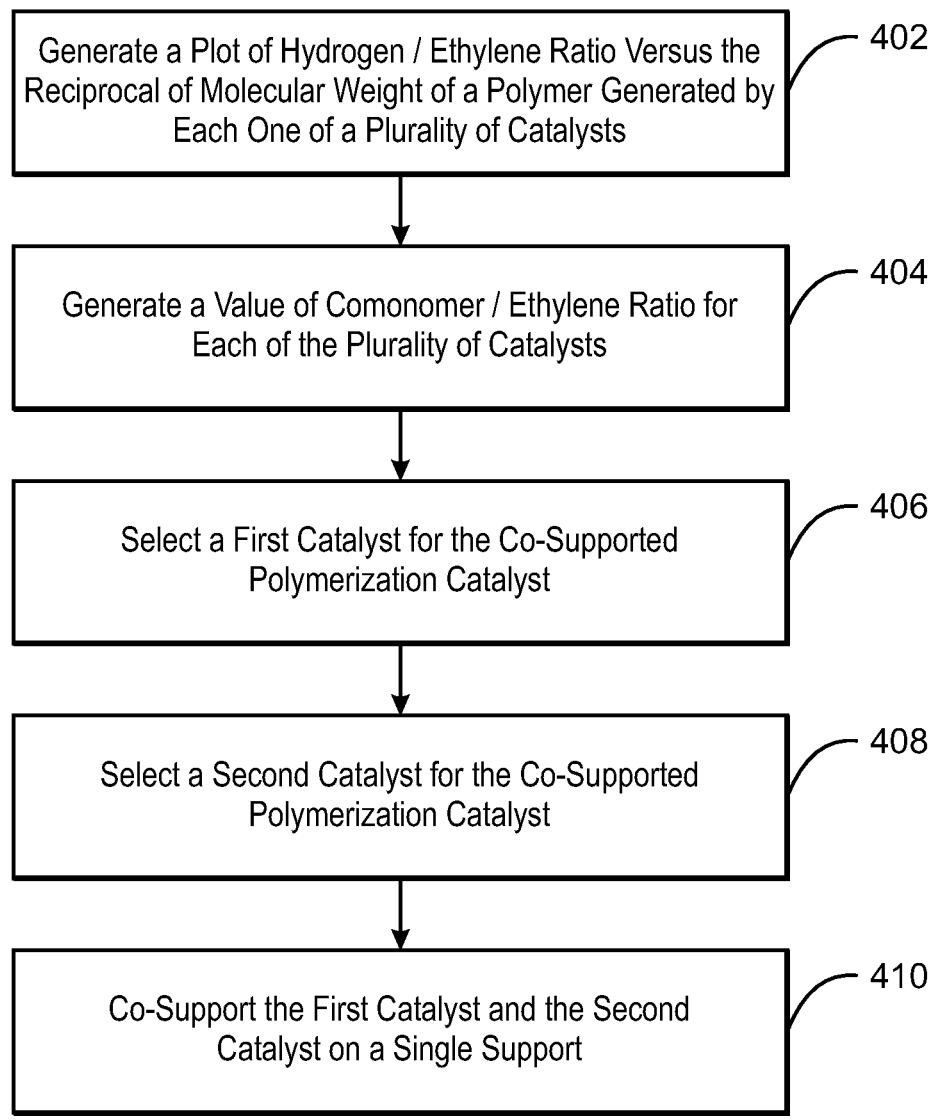
FIG. 4 is a flow chart of a method for making a co-supported polymerization catalyst.

FIG. 4 is a flow chart of a method 400 for making a co-supported polymerization catalyst. The method 400 begins at block 402 with the generation of a plot of hydrogen/ethylene ratio versus the reciprocal of molecular weight of a polymer generated by each one of a number of catalysts. As discussed herein, the slope of each plot indicates the response of the corresponding catalyst to a hydrogen level.

At block 404, a value is determined for the comonomer/ethylene ratio for each of the catalysts that can be used to achieve a single target density, such as 0.92. The value of the ratio used to achieve the target density indicates the ability of the catalyst to incorporate comonomer. At block 406, a first catalyst is selected for the co-supported polymerization catalyst. For example, the first catalyst can be a commonly used commercial catalyst, or may be selected to have a low or a high ability to incorporate comonomer and a high or low response to hydrogen.

At block 408, a second catalyst is selected for the co-supported polymerization catalyst. The second catalyst can be selected to have a slope of the plot for the hydrogen/ethylene ratio versus the reciprocal of molecular weight that is at least about 1.5 times as large as the slope of the plot for the first catalyst. Further, the second catalyst can be selected to have a value for the comonomer/ethylene ratio that is less than about 0.5 as large as comonomer/ethylene ratio of the first catalyst. At block 410, the first catalyst and the second catalyst can be co-supported on a single support to create the co-supported polymerization catalyst, for example, using the trim techniques described herein, among others.

Selecting a Catalyst Blend for a Particular Product Type

The techniques described herein can be used to select a blend of at least two catalysts to generate a polymer that maintains a consistent blend polydispersity index (bPDI) as the melt index is adjusted to match a particular fabrication process, such as blown film, rotational molding, and injection molding, among others. For example, a polymer having a melt index of about 0.5 to about 1.0 may work well in blown film, while a polymer for rotational molding may work well at a melt index of about 2 to about 7. Similarly, a polymer with a melt index of about 20 to about 100 may work well for injection molding. Further, the techniques may allow for selecting catalysts and conditions that allow the adjustment of bPDI while maintaining a consistent melt flow.

The methods allow for the prediction of the bPDI of a polymer formed by a mix-catalyst from the hydrogen responses of the component catalysts, and identify catalysts for products based on analyses of hypothetical catalyst-pairs. Further, a complete bPDI map may be constructed to facilitate product design across a range of applications for a given catalyst-pair.

A number of assumptions and conditions can be considered for the selection technique. For example, in a theoretically ideal catalyst blend, the individual catalyst components may behave independently in the mixture. Further, for each component, the PDI and productivity may remain the same over an entire $H_2/C_2$ range (termed hydrogen response herein). Finally, in the techniques described, other factors that may influence the catalyst behavior, such as the comonomer response, among others, may be assumed to not significantly influence the hydrogen response.

The hydrogen response for a particular catalyst may determined by measuring the weight average molecular weight (Mw) of a polymer generated by the catalyst at a number of $H_2/C_2$ ratios, for example, by gel permeation chromatography, light scattering, or other related techniques. The results can then be used to calculate a linear fit to the formula in Eqn 1.

$$1/Mw = \text{Intercept} + \text{Slope} * (H_2/C_2) \qquad \text{Eqn. 1}$$

For predictions of blends, the $H_2/C_2$ ratio is expressed in the same units, e.g., ppm/mole %, as used in the polymerization processes. Eqn. 1 can then be use to predict a Mw for the catalyst at a selected $H_2/C_2$ ratio, generally, so long as the data collected for the linear fit included the desired $H_2/C_2$ ratio. The same process can be repeated for the second catalyst used in the blend. Although this discussion will focus on two catalysts, as an example of the procedure, it can be understood that the techniques may be extended to any number of catalysts in the blend.

While the hydrogen response is modeled, the polydispersity index for each polymer used in the blend may be measured at the same points used for Eqn. 1. If a single catalyst being evaluated for use in a catalyst blend generates a polymer with a multimodal molecular weight distribution the distribution may have to be deconvoluted to multiple populations and used as individual components to make up the final blend. Eqn. 2 is a theoretical blending rule for Mw of a blend from its components.

$$bmw = Fhmw * hmw + Flmw * lmw \qquad \text{Eqn. 2}$$

In Eqn. 2, bmw is the blend molecular weight, e.g., the effective unimodal molecular weight of a polymer generated by the catalyst, or catalyst blend. Fhmw is the weight fraction of the high molecular weight component and hmw is the molecular weight of the high molecular weight component. Similarly, Flmw is the weight fraction of the low molecular weight component and lmw is the molecular weight of the low molecular weight component. While the calculation of the effective molecular weight is performed for a bimodal catalyst, similar calculations can be performed for a multimodal distribution or a broad molecular weight distribution for a catalyst. Further, Eqn. 2 can be used to determine an effective blend molecular weight (bmw) for a polymer generated by the final blend of two or more catalysts.

Once the hydrogen response of the basic catalyst components is determined, a bPDI curve versus Mw may be calculated using the relationship in Eqn. 3.

$$bPDI=[Flmw+Fhmw*(hmw/lmw)]*[Flmw*lPDI+Fhmw*hPDI*(lmw/hmw)] \qquad \text{Eqn. 3}$$

As in Eqn. 2, in Eqn. 3, Flmw is a weight fraction of a low molecular weight polymer component and Fhmw is a weight fraction of a high molecular weight polymer component. In this case, however, each of the components may be the effective molecular weight of the polymer, e.g., generated by an equivalent unimodal catalyst.

Flmw and Fhmw are calculated from the amount of polymer generated by the first catalyst at each hydrogen to ethylene ratio and the amount of polymer generated by the second catalyst at each hydrogen to ethylene ratio. In an embodiment, the productivity of the catalysts is not taken into account, and the amounts of the catalysts are used as proxies for the amount of polymer to determine the ratio.

The term lmw is the weight average molecular weight of the low molecular weight polymer component, e.g., generated by one of the catalysts, and hmw is the weight average molecular weight of the high molecular weight polymer component, e.g., generated by another catalyst. The lmw and hmw may be calculated from the relationship of the molecular weight to the ratio of the hydrogen to ethylene, e.g., the hydrogen response for each catalyst that is modeled in Eqn. 1. While the polydispersities do not have to be taken into account in Eqn. 2, they will affect the final polymer properties, and are part of Eqn. 3. The term lPDI is the polydispersity of the low molecular weight polymer component, and hPDI is the polydispersity of the high molecular weight polymer component. The lPDI and hPDI may be measured for each polymer and, in an embodiment, are assumed to be a constant value.

The use of the techniques above can be demonstrated using polymers generated by two hypothetical catalysts described herein, Hypo-H and Hypo-L. The Hypo-H catalyst produces a higher molecular weight polymer component while the Hypo-L produces a lower molecular weight polymer component. The hydrogen responses of the two catalysts were mapped to Eqn. 1 using the techniques described herein, giving the results shown in Table 6. As discussed in the later sections, the ratio of intercept and the ratio of slop between the two catalyst components also play a critical role for the selection of catalyst pair. These two ratios are defined in Eqns. 4 and 5.

$$b\text{-Ratio}=\text{intercept of Hypo-L/intercept of Hypo-H} \qquad \text{Eqn.4}$$

$$m\text{-Ratio}=\text{slope of Hypo-L/slope of Hypo-H} \qquad \text{Eqn.5}$$

TABLE 6

Linear Parameters for Eqn. 1 for Hypo-H and Hypo-L

| Catalyst | b (intercept) | m (slope) | ePDI |
|---|---|---|---|
| Hypo-H | 1.00E−06 | 1.00E−06 | 3.0 |
| Hypo-L | 5.00E−06 | 5.00E−06 | 3.0 |
| b-Ratio or m-Ratio (Hypo-L/Hypo-H) | 5.0 | 5.0 | |

In a first example, a catalyst ratio of 50/50 is selected, and the assumption is made that the catalyst ratio predicts the weight fraction of each polymer formed by a catalyst in the blend. The hydrogen to ethylene ratio can then be adjusted to reach particular melt index targets for different applications, while keeping the bPDI at the same value, as shown in Table 7. The applications are blown film (BF), rotational molding (RM), and injection molding (IM). While these applications are used as examples, catalyst blends may be selected for any number of other applications using the present techniques, such as blow molding or sheet forming, among others.

TABLE 7

Same Catalyst Ratio, Adjusting Hydrogen to Reach Different MI Targets

| Application | H2/C2 (ppm/mol %) | Fhmw | Flmw | hmw (/1000) | lmw (/1000) | bmw (/1000) | hmw/lmw | bPDI |
|---|---|---|---|---|---|---|---|---|
| BF 0.5 MI | 3.90 | 0.50 | 0.50 | 204.0 | 40.8 | 122.4 | 5.00 | 5.40 |
| BF 1.0 MI | 5.00 | 0.50 | 0.50 | 166.7 | 33.3 | 100.0 | 5.00 | 5.40 |
| RM 2 MI | 6.06 | 0.50 | 0.50 | 141.7 | 28.3 | 85.0 | 5.00 | 5.40 |
| RM 7 MI | 8.84 | 0.50 | 0.50 | 101.7 | 20.3 | 61.0 | 5.00 | 5.40 |
| IM 20 MI | 12.04 | 0.50 | 0.50 | 76.7 | 15.3 | 46.0 | 5.00 | 5.40 |
| IM 50 MI | 15.67 | 0.50 | 0.50 | 60.0 | 12.0 | 36.0 | 5.00 | 5.40 |
| IM 100 MI | 19.00 | 0.50 | 0.50 | 50.0 | 10.0 | 30.0 | 5.00 | 5.40 |

As a further example, Table 8 shows results that may be obtained by mapping the bPDI curves at a single melt index, for example, for a single application such as blown film (BF). In this case, the catalyst ratio is adjusted, while the hydrogen to ethylene ratio is set to keep the melt index at 1.

TABLE 8

Adjusting Catalyst Ratio, Adjusting Hydrogen to Hold MI Constant

| Application | H2/C2 (ppm/mol %) | Fhmw | Flmw | hmw (/1000) | lmw (/1000) | bmw (/1000) | hmw/lmw | bPDI |
|---|---|---|---|---|---|---|---|---|
| BF 1.0 MI | 1.00 | 0.00 | 1.00 |  | 100.0 | 100 | 5.00 | 3.00 |
| BF 1.0 MI | 3.00 | 0.25 | 0.75 | 250.0 | 50.0 | 100 | 5.00 | 4.80 |
| BF 1.0 MI | 5.00 | 0.50 | 0.50 | 166.7 | 33.3 | 100 | 5.00 | 5.40 |

TABLE 8-continued

Adjusting Catalyst Ratio, Adjusting Hydrogen to Hold MI Constant

| Application | H2/C2 (ppm/mol %) | Fhmw | Flmw | hmw (/1000) | lmw (/1000) | bmw (/1000) | hmw/lmw | bPDI |
|---|---|---|---|---|---|---|---|---|
| BF 1.0 MI | 7.00 | 0.75 | 0.25 | 125.0 | 25.0 | 100 | 5.00 | 4.80 |
| BF 1.0 MI | 9.00 | 1.00 | 0.00 | 100.0 | | 100 | 5.00 | 3.00 |

The techniques may be used to map catalyst behavior for both actual catalyst systems and for hypothetical catalyst systems, for example, to determine the characteristics of catalyst systems needed to for an ideal polymer. FIGS. 5, 6, and 7 are plots of three hypothetical examples, A, B, and C. As shown in Table 9, the high molecular weigh catalysts in all three examples (i.e., A1, B1 & C1) are identical, having an intercept of 1.0E-06 and a slope of 1.0E-06 as determined by the linear fit of Eqn. 1. The low molecular weight catalysts (i.e., A2, B2 & C2), on the other hand, are designed in such a way that; the ratio of the intercept and the ratio of slope within each pair varies from 10:1, 1:10 & 10:10 for examples A, B & C, respectively. In all three cases, a value of 3.0 was assigned for both lPDI and hPDI in order to calculate bPDI according to Eqn. 3

TABLE 9

Ratio of Parameters for Hydrogen Response (Eqn. 1)

| Hypothetical | b-Ratio for Intercept | m-Ratio for slope |
|---|---|---|
| A | A2/A1 = 10<br>A2 = 1.0E-05<br>A1 = 1.0E-06 | A2/A1 = 1<br>A2 = 1.0E-06<br>A1 = 1.0E-06 |
| B | B2/B1 = 1<br>B2 = 1.0E-06<br>B1 = 1.0E-06 | B2/B1 = 10<br>B2 = 1.0E-05<br>B1 = 1.0E-06 |
| C | C2/C1 = 10<br>C2 = 1.0E-05<br>C1 = 1.0E-06 | C2/C1 = 10<br>C2 = 1.0E-05<br>C1 = 1.0E-06 |

Figure 5A:
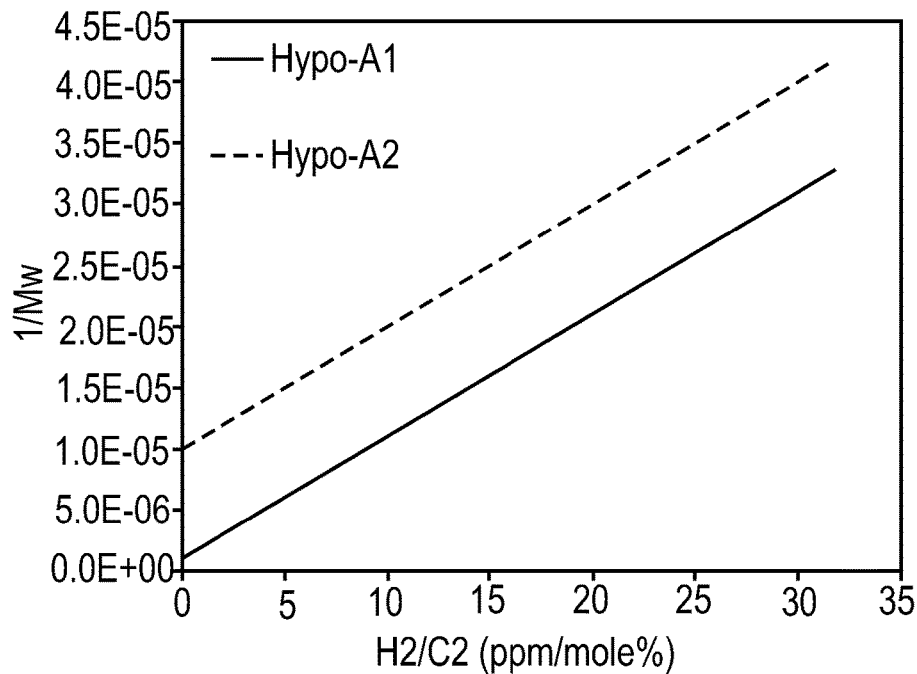
FIGS. 5A, 5B, and 5C are log plots of the inverse of the molecular weight to the $H_2/C_2$ ratio for each of the hypothetical combinations.
Figure 5B:
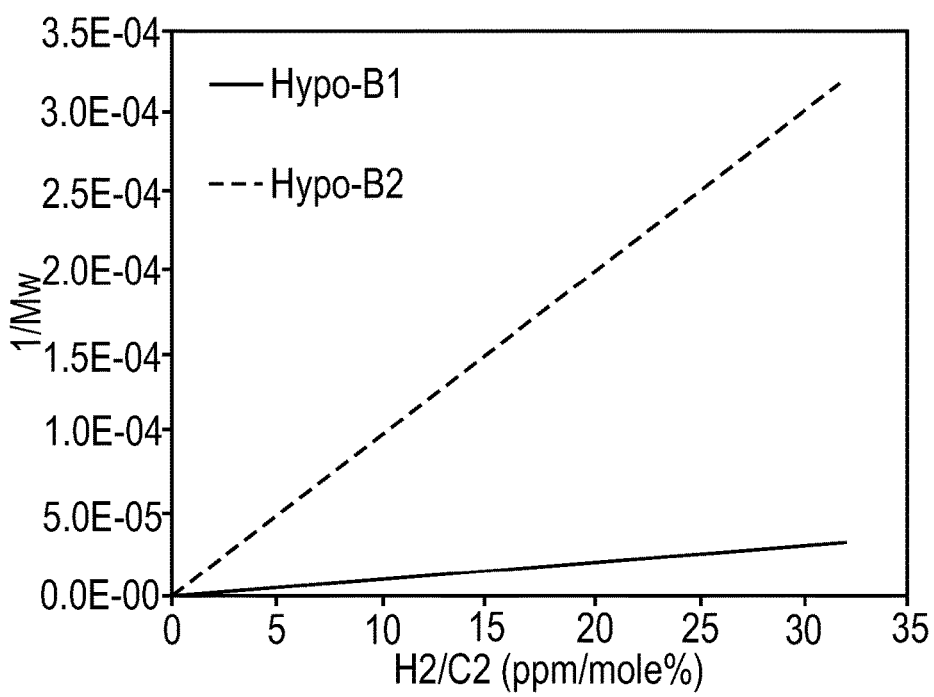
Figure 5C:
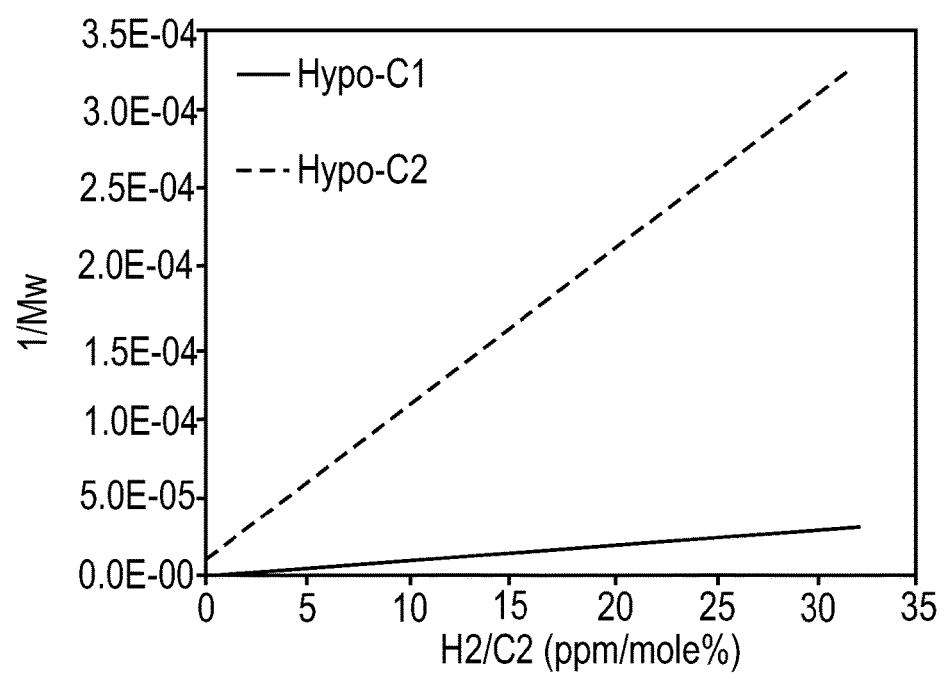

FIGS. 5A, 5B, and 5C are log plots of the inverse of the molecular weight to the $H_2/C_2$ ratio for each of the hypothetical combinations. In each plot, the dashed line represents a lower molecular weight polymer generated by a catalyst (2) and the solid, line represents a higher molecular weight polymer generated by another catalyst (1). The results of these changes are shown in FIGS. 6A, 6B, and 6C.

Figure 6A:
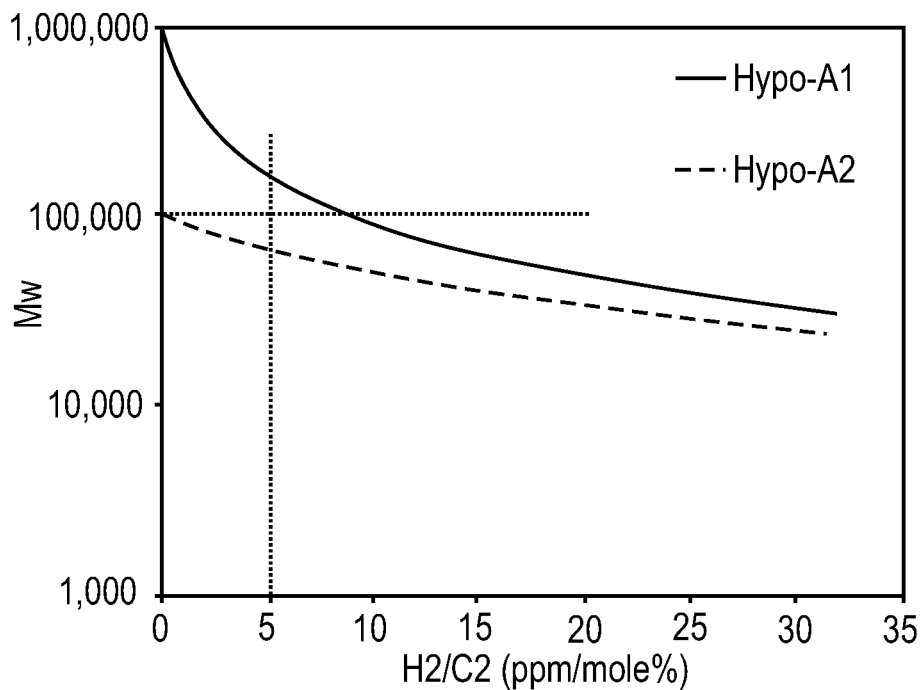
FIGS. 6A, 6B, and 6C are plots of the hydrogen response for each of the catalysts.
Figure 6B:
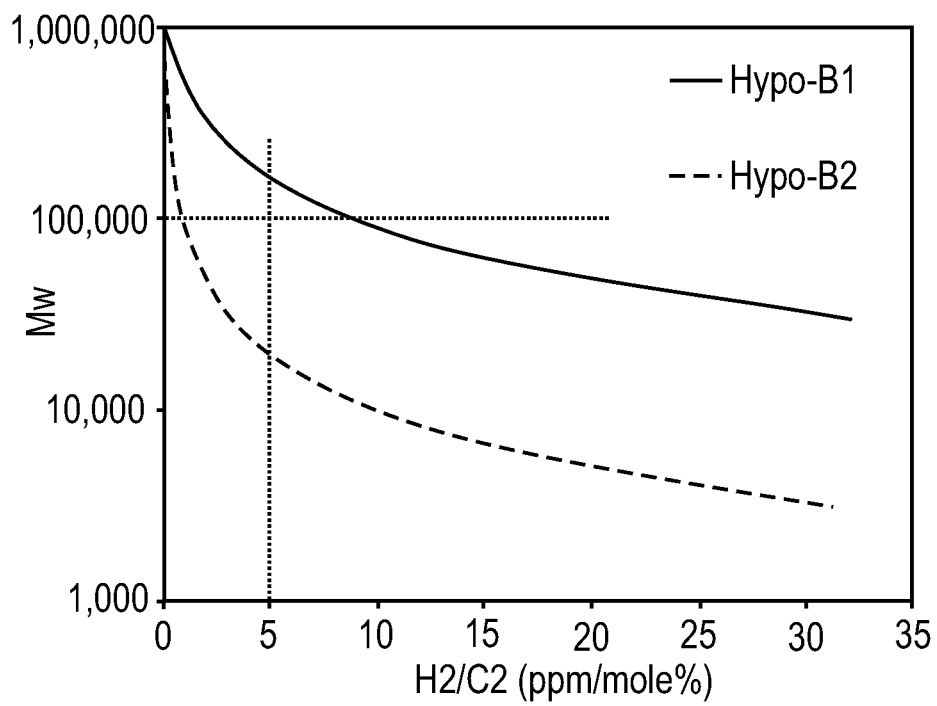
Figure 6C:
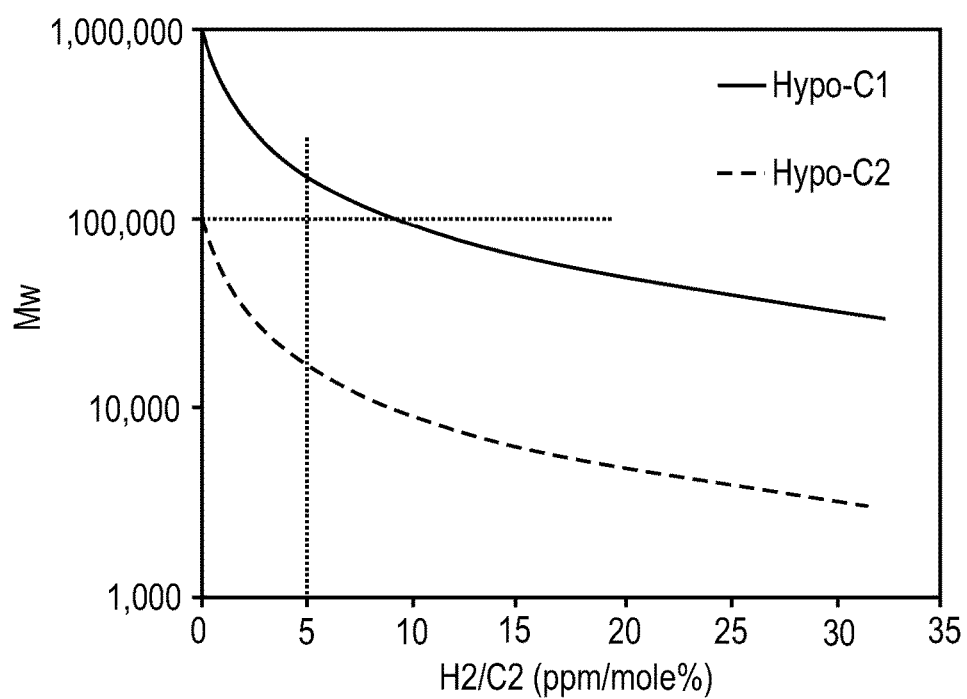

FIGS. 6A, 6B, and 6C are plots of the hydrogen response for each of the catalysts. The space between the solid line, representing the higher molecular weight species, and the dashed line, representing the lower molecular weight species, is the region through which the molecular weight can be controlled by adjusting the ratio of the catalysts and H2/C2 ratio in reactor operation. Note that the solid and the dash lines are not parallel in FIGS. 6A & 6B. This means that their control space would have to be clamped down significantly either in the high H2/C2 region for example A or in the low H2/C2 region for example B. The consequence of such limitation is to lose some of their product design capabilities. For example, the combination would be unable to reach a higher bPDI targets for high MI applications in FIG. 7A and to reach a higher bPDI targets for low MI applications in FIG. 7B.

Figure 7A:
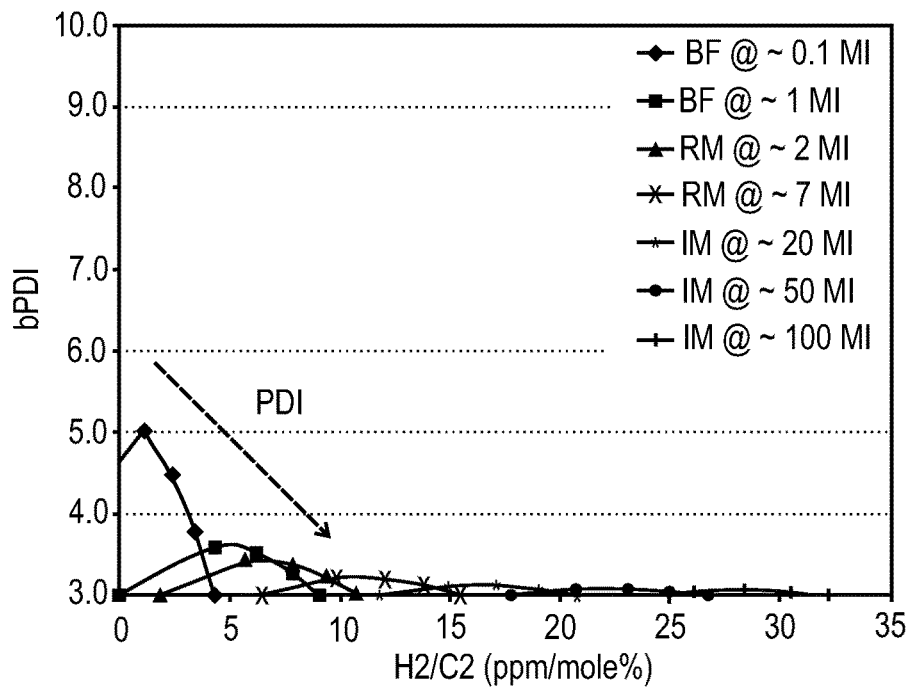
FIGS. 7A, 7B, and 7C are bPDI maps generated for polymers produced by the catalyst blend.
Figure 7B:
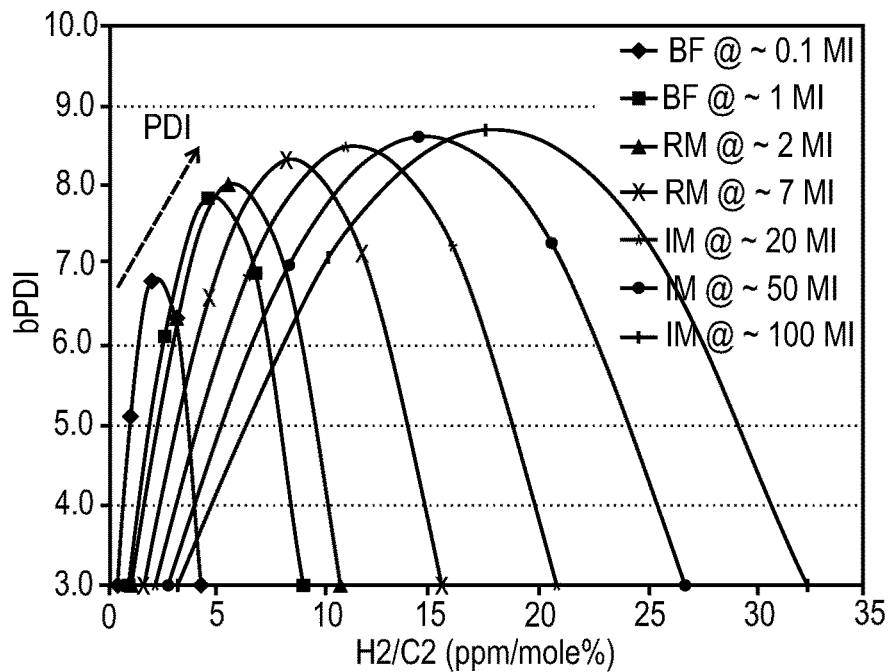
Figure 7C:
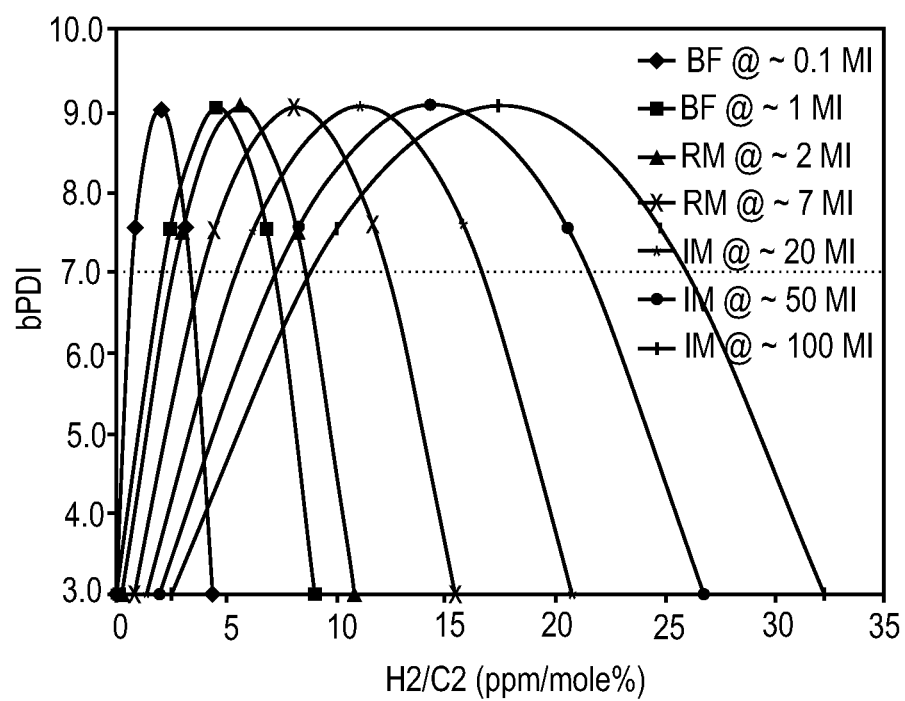

Example C, on the other hand, has a pair of parallel H-response lines as shown in FIG. 6C. Its control space is therefore bigger than the other two examples shown in FIGS. 6A & 6B, Its bPDI capability as shown in FIG. 7C remains the same for all applications (i.e., same product design capability). The key to ensure a good product design capability from a catalyst pair is to have the value of b-Ratio in Table 9 as close to the value of m-Ratio as possible. As a general guidance, one would like to have a catalyst pair with b-Ratio/m-Ratio≤2 or, more preferably, with b-Ratio/m-Ratio≤1. In another way to describe; Example-C is the most desirable case for greatest design capability with b-Ratio=m-Ratio, Example-B is the less desirable but still have decent design capability with b-Ratio<m-Ratio and Example-A is the least preferred case with little design capability where b-Ratio>m-Ratio.

Up to this point, the discussions have been directed to the "relative" shape and capability of H-response curve and bPDI map among the three basic types of catalyst pair. However, the "absolute" values of Mw=f(H2/C2) and the "absolute" value of bPDI can be further adjusted by the values of intercept and slope in Eqn. 1. Following are meant for trendwise discussion with the understanding that absolute values can be adjusted through intercept and slope in Eqn. 1. In FIG. 7A, it is apparent that the bPDI is falling off as the $H_2/C_2$ ratio is increased, resulting in a polymer with a polydispersity little different from the base polymers. This combination of catalysts would not provide much control for the product, and, generally, indicates a combination to be avoided. The situation represented in FIG. 7B is more favorable. However the similar intercept indicates that the bPDI will be lower for applications that require higher molecular weights (such as blown film application) and higher for applications require lower molecular weights (e.g., injection molding). This is an opposite trend to the general practice in the industry (e.g., a lower PDI is preferred for injection molding and a higher PDI is preferred for blown film). FIG. 7C indicates a favorable catalyst combination. In this combination, there is substantial control of both the higher and lower molecular weight polymers, indicated by the high uniform values for bPDI across the range of the $H_2/C_2$ ratio.

Figure 8:
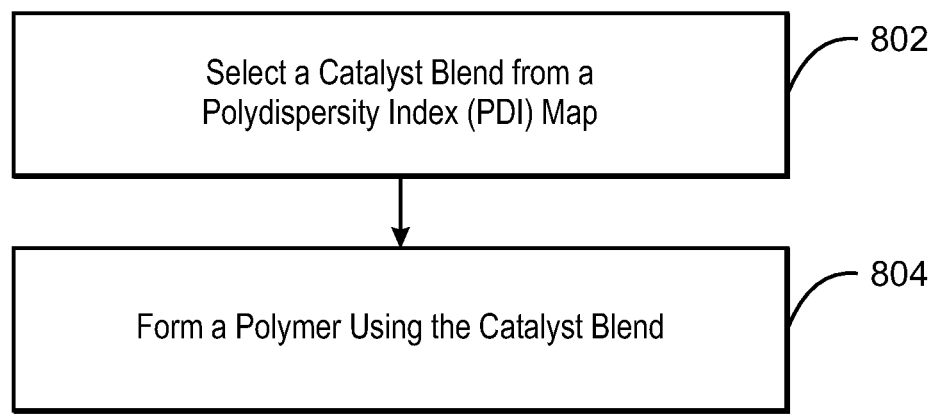
FIG. 8 is a process flow diagram of a method for using a bPDI map to assist in forming a polymer.

FIG. 8 is a process flow diagram of a method 800 for using a bPDI map to assist in forming a polymer. The method begins at block 802 with the selection of a catalyst blend from a bPDI map. As noted with respect to FIGS. 6 and 7, a good catalyst selection would have a substantially parallel hydrogen response between the catalysts, e.g., in FIG. 6C, and a high consistent value of hmw/lmw as shown in Table 7 & 8 for greatest bPDI design capability. Once the catalyst pair is selected, at block 804 a polymer can be formed with the catalyst blend. This may include any number of other actions described herein, such as using a trim system and the hydrogen addition to control the properties of the resulting polymer.

Figure 9:
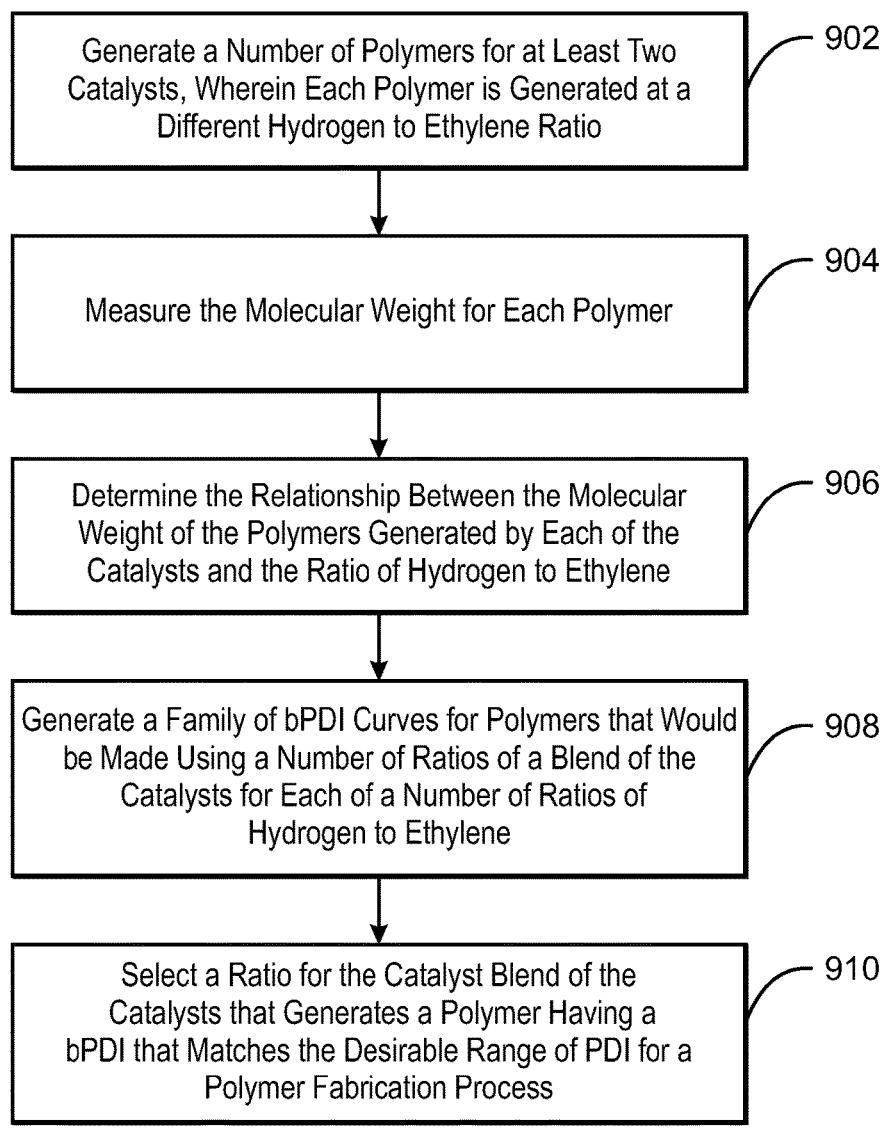
FIG. 9 is a process flow diagram of a method 900 for selecting a catalyst blend, e.g., at block 802 of FIG. 8.

FIG. 9 is a process flow diagram of a method 900 for selecting a catalyst blend, e.g., at block 802 of FIG. 8. The method begins at block 902 with the generation of a number of polymers for at least two catalysts. Each polymer is generated at different hydrogen to ethylene ratios. At least one of the catalysts generates a higher molecular weight polymer and another catalyst generates a lower molecular weight polymer. At block 904, the molecular weight is measured for each polymer. At block 906, the relationship between the molecular weight of the polymers generated by each of the catalysts and the ratio of hydrogen to ethylene is determined. This may be, for example, performed by the methods described with respect to Eqn. 1, and by the generation of the plots shown in FIGS. 5 and 6. At block 906, a family of bPDI curves is generated for polymers that would be made using a number of ratios of a blend of the catalysts for each of a number of ratios of hydrogen to ethylene. This may be performed using the methods described with respect to Eqn. 3, and with respect to the plots shown in FIG. 7. At block 910, a ratio for a blend of at least two catalysts that generates a polymer having a bPDI that matches a polymer fabrication process may be selected. The operation of the blend may be confirmed by generating a polymer at each of a number of $H_2/C_2$ ratios and comparing values of bPDI and MI to the predicted values.

General Procedures for Forming Catalyst Components

Catalysts

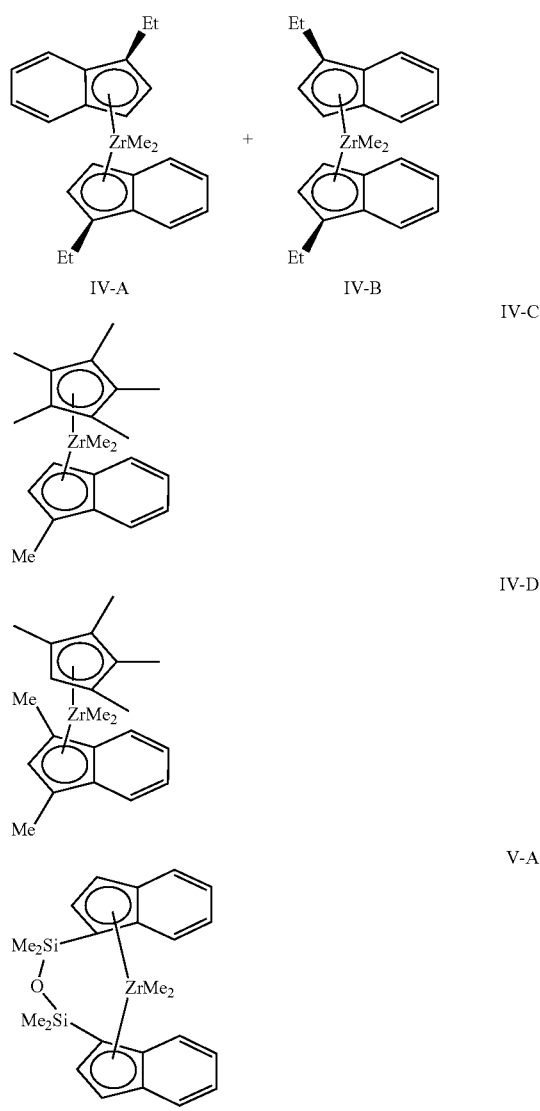

-continued

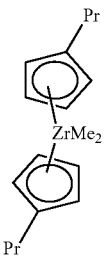

III

Experimental

All manipulations were performed in an $N_2$ purged glovebox or using standard Schlenk techniques. All anhydrous solvents were purchased from Sigma-Aldrich and were degassed and dried over calcined $Al_2O_3$ beads or molecular sieves prior to use. Toluene for the catalyst preparations was pre-dried with $Al_2O_3$ beads then dried over SMAO 757 before use. Deuterated solvents were purchased from Cambridge Isotope Laboratories and were degassed and dried over alumina beads or molecular sieves prior to use. Reagents used were purchased from Sigma-Aldrich, with the exception of $ZrCl_4$ 99+% which was purchased from Strem Chemicals, and bis(n-propyl-cyclopentadienyl)hafnium dimethyl ($HfPMe_2$) was purchased from Boulder Scientific Lot# BSC3220-8-0002. $^1H$ NMR measurements were recorded on a 250 Mz Bruker and a 500 Mz Bruker spectrometers.

Synthesis of Rac-meso-bis(1-Ethyl-indenyl)zirconium dimethyl (1-EtInd)$_2$ZrMe$_2$ (IV-A/IV-B)

Indenyllithium

Freshly distilled indene (50.43 g, 434.1 mmol) was dissolved in 1 L of pentane. $Et_2O$ (25 mL) then 1.6M n-butyllithium in hexanes (268.5 mL, 429.6 mmol) were added to the clear stirring solution over a span of 5 min. A white solid precipitated and the supernatant took on a light yellow color. After stirring overnight the suspension was filtered then dried in vacuo to yield a white solid (46.51 g, 381.0 mmol, 88.7%). $^1H$ NMR (THF-$d_8$): δ 5.91 (d, 2H), 6.44 (m, 2H), 6.51 (t, 1H), 7.31 (m, 2H).

1-Ethylindene 46.51 g (380.95 mmol) of indenyllithium was dissolved in 250 mL of $Et_2O$, and a separate solution was made of 95.94 g (615.12 mmol) of ethyliodide in 400 mL of $Et_2O$. The ethyliodide solution was cooled to −30° C. in and the indenyllithium solution was cooled to 0-10° C. using a dry ice/acetone bath. The indenyllithium was added to the clear stirring solution of ethylidode via cannula transfer. The solution became a light yellow to yellow color upon addition of the indenyllithium solution. The reaction was allowed to stir overnight and slowly warm to room temperature. After stirring overnight the flask was brought into the box and the $Et_2O$ was reduced in vacuo. Once LiI began to precipitate, 300 mL of pentane was added and the white suspension was filtered resulting in a light orange solution. The pentane was evaporated where more LiI precipitated and a light orange oily liquid was obtained. The crude product was distilled under diminished pressure using a rotary vacuum pump to a slight yellow clear liquid. $^1$H NMR showed ~90% 1-Ethyl-indene and ~10% 3-Ethylindene. Possible isomerization could have occurred due to a small amount of acid present during the distillation as none was present in the crude $^1$H NMR spectrum. 44.27 g (306.96 mmol) of product was isolated for an 80.6% yield. $^1$H NMR (CD$_2$Cl$_2$): δ 0.96 (3H, t), 1.59 (1H, q), 1.99 (1H, q), 3.41 (1H, m), 6.58 (1H, d), 6.59 (1H, d), 7.24 (2H, m), 7.41 (2H, dd).

1-Ethyl indenyllithium 44.27 g (306.98 mmol) of 1-Ethylindene containing ~10% 3-Ethylindene was dissolved in 500 mL of pentane and ca. 3 mL of Et$_2$O. To the clear stirring solution was added 188.28 mL (301.25 mmol) of 1.6M n-butyllithium in hexanes over 10 minutes. Immediately a flaky white precipitate formed and caused the stirring stop. The mixture was manually stirred to ensure proper incorporation of reagents and the suspension was allowed to sit overnight. The suspension was filtered and the white solid dried in vacuo. 43.27 g (288.18 mmol) of product was obtained for a 95.7% yield. 1H NMR (THF-d8): δ 1.26 (3H, triplet), 2.86 (2H, quartet), 5.72 (doublet, 1H), 6.38 (dd 1H), 6.43 (2H, m), 7.26 (1H, t), 7.30 (1H, m).

Rac-meso-bis(1-Ethyl-indenyl)zirconium dimethyl (1-EtInd)$_2$ZrMe$_2$ (IV-A/B)

7.00 g (46.65 mmol) of 1-Ethyl-indenyllithium was dissolved in 74 mL of 1, 2-dimethoxyethane (DME) and a separate solution was made with 5.43 g (23.30 mmol) of ZrCl$_4$ in 75 mL of DME. To the clear ZrCl$_4$ solution was added the bright yellow solution of 1-ethyl-indenyllithium via pipette over a fifteen minute period. Upon initial addition the solution took on a yellow color, and after 5 minutes into the addition a precipitate formed and an orange-yellow color ensued. Ten minutes into the addition the supernatant turned orange with a yellow precipitate, and once all the 1-ethyl-indenylltihium solution was added the mixture turned back to yellow. The reaction was allowed to stir overnight. A crude $^1$H NMR spectrum of the slurry showed a rac/meso ratio of ~1.1:1; however this can be misleading since the rac isomer is more soluble in DME than the meso isomer. Regardless of the isomer ratio, 15.61 mL (46.83 mmol) of 3.0M CH$_3$MgBr in Et$_2$O was added in 1 mL portions over ten minutes. After the tenth addition the yellow mixture turned an orangish color. Upon the final addition of the Grignard reagent, the mixture had turned brown and the reaction was allowed to stir overnight. A $^1$H NMR spectrum of the crude mixture revealed a 1.1:1 meso/rac ratio. The DME was evaporated and the brown solid was extracted with 3×20 mL of toluene plus an additional 10 mL. The light brown solid obtained after solvent removal was washed with 10 mL of pentane and dried in vacuo. 8.26 g (20.26 mmol) of the off-white solid was obtained for an 87% yield.

Dichloride spectral data: $^1$H NMR (CD$_2$Cl$_2$): δ 1.16 (6.34H, t, rac), 1.24 (6H, t, meso), 2.73-2.97 (8H, overlapping q), 5.69 (1.82H, dd, meso), 5.94 (1.92H, dd, rac), 6.06 (1.99H, d, rac), 6.35 (1.84H, d, meso), 7.22-7.65 (16H, m).

Dimethyl Spectral Data: $^1$H NMR (C$_6$D$_6$): δ −1.40 (3.33H, s, meso), −0.895 (6H, s, rac), −0.323 (3.34H, s, meso), 1.07 (13H, overlapping t), 2.47 (4H, overlapping q), 2.72 (4H, q), 5.45-5.52 (8H, m), 6.91 (8H, m), 7.06-7.13 (4H, m), 7.30 (4H, m).

Synthesis of Rac-meso-bis(1-Ethyl-indenyl)zirconium dimethyl (1-EtInd)$_2$ZrMe$_2$ (IV-A/B)

To a solution of ZrCl$_4$ (20.8 g; 89.3 mmol) in 1, 2-dimethoxyethane (DME) (ca. 100 mL) was added a solution of 1-ethyl-indenyllithium (26.8 g; 178 mmol) dissolved in 1, 2-dimethoxyethane (DME) (ca. 200 mL) in portions of about 5 mL over 15 minutes. Additional DME was added as necessary to keep the reaction from becoming too thick to stir. The total volume at the end of the addition was about 425 mL. Immediately prior to the addition of the 1-Ethyl-indenyllithium solution and about halfway through the addition, pentane (ca. 10 mL) was added to the reaction mixture and removed under vacuum in order to lower the temperature. After stirring about 4 h at room temperature an aliquot of the slurry was removed and dried down. The 1H NMR of the solid thus obtained was taken in CD$_2$Cl$_2$ and showed a rac/meso ratio of 0.7:1.

Approximately 100 mL of the solvent was evaporated from the reaction and methyllithium solution (1.6 M in ether; 111 mL; 178 mmol) was added in portions (ca. 20 mL) over about an hour. After stirring overnight the rac/meso ratio was 0.7:1.0. Additional MeLi solution (1.6 M in ether; 7.0 mL; 11.2 mmol) was added and the reaction stirred at room temperature for 3 days. The rac/meso ratio was 0.9:1 as determined by $^1$H NMR. The solvent was removed under vacuum and the residue was extracted with warm hexanes (ca. 300 mL; 60° C.), filtered and concentrated to about 100 mL total volume then cooled to −20° C. overnight. The solid was isolated by filtration, washed with cold pentane (2×50 mL) and dried under vacuum to give 29.2 g solid with a rac/meso ration of 0.94:1. The isolated solid was extracted with warm hexane (ca. 150 mL) filtered away from a small amount of pink solid. The volume was reduced to about 125 mL and the solution was treated with trimethylsilylchloride (2.0 mL). The solution was filtered, concentrated to about 100 mL, heated to re-dissolve the precipitated product and allowed to cool slowly. After sitting overnight, the flask was cooled to −20 C which caused some pink solid to precipitate. The flask was warmed to 55° C. and additional hexanes (ca. 75 mL) was added along with trimethylsilylchloride (5.0 mL). This was kept at 55° C. for two hours, the reaction was filtered to give a yellow solution. The solution was filtered, concentrated to about 100 mL, heated to re-dissolve the precipitated product and allowed to cool slowly. The precipitated solid was isolated by filtration, washed with cold pentane (2×30 mL), dried under vacuum at 55° C. The yield was 21.1 g with a rac/meso ration of 1.19/1.

Synthesis of meso-(1-EtInd)$_2$ZrCl$_2$

1-Ethylindenyllithium (1.0 g; 6.7 mmol) was dissolved in dimethoxyethane (DME) (7.7 mL) and cooled to −20° C. Solid ZrCl$_4$ (0.781 g; 3.35 mmol) was added in portions over 5 minutes and the reaction was continued overnight. After the volatiles were removed, the yellow solids thus obtained were extracted with CH$_2$Cl$_2$ until no yellow color remained. The CH$_2$Cl$_2$ was removed under vacuum leaving a yellow solid. Yield=1.14 g with a meso/rac ratio of 19:1.

Conversion of meso-(1-EtInd)$_2$ZrCl$_2$ to meso-(1-EtInd)$_2$ZrMe$_2$ meso-(1-EtInd)$_2$ZrCl$_2$ (1:19 rac/meso; 307 mg; 0.68 mmol) was slurried in Et$_2$O (ca. 10 mL) and MeMgBr (3.0 M in Et$_2$O; 0.47 mL; 1.41 mmol) was added. The reaction was dried down and extracted with warm hexanes (ca. 18 mL at 60° C.), filtered and dried down to a light yellow solid (240 mg). The $^1$H NMR in C$_6$D$_6$ showed the rac/meso ratio of 1:19 was retained.

Conversion of 1:1 rac/meso-(1-EtInd)$_2$ZrCl$_2$ to 1:1 rac/meso-(1-EtInd)$_2$ZrMe$_2$ (1-EtInd)$_2$ZrCl$_2$ (1:1 rac/meso; 12.2 g; 27.2 mmol) was slurried in Et$_2$O (ca. 80 mL) and MeMgBr (2.6 M in Et$_2$O;

23.2 mL; 60.3 mmol) was added. The reaction was stirred overnight, the reaction was dried down and extracted with warm hexanes (ca. 300 mL), filtered and about 1 mL of the solution was dried down and the $^1$H NMR in $C_6D_6$ showed a very clean 1:1 meso/rac ratio of (1-EtInd)$_2$ZrMe$_2$ Conversion of meso rich (1-EtInd)$_2$ZrCl$_2$ to close to 1:1 rac/meso (1-EtInd)$_2$ZrMe$_2$ meso-(1-EtInd)$_2$ZrCl$_2$ (1:5 rac/meso; 244 mg; 0.54 mmol) was slurried in Et$_2$O (ca. 5 mL) and MeLi (1.6 M in Et$_2$O; 0.69 mL; 1.10 mmol) was added. The reaction was stirred overnight, filtered and an aliquot of the filtered reaction mixture was dried down. The $^1$H NMR in $C_6D_6$ showed a 1:1.24 rac/meso ratio.

Synthesis of (1-Methylindenyl)(pentamethylcyclopentadienyl)zirconium(IV) dimethyl (IV-C)

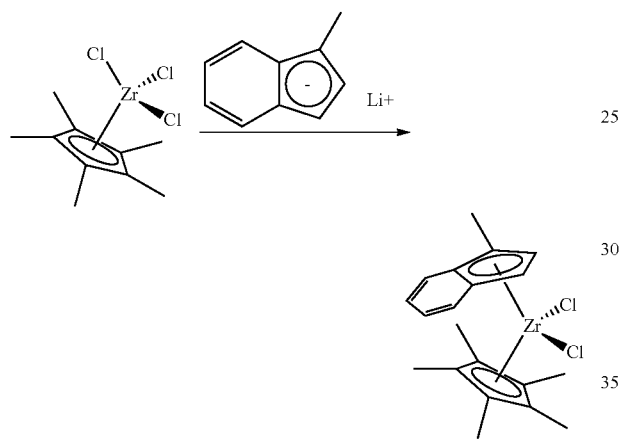

(1-Methylindenyl)(pentamethylcyclopentadienyl) zirconium(IV)dichloride

In the drybox, weighed 1-Methyl-1H-indene oil (1.85 g, 14.2 mmol) into a 250 ml roundbottom flask and dissolved in 25 ml dry diethyl ether. Added n-Butyllithium (1.6 M in hexanes, 12.0 ml, 19.2 mmol) dropwise from a 20 ml needle/syringe to form a yellow solution. Stirred at room temperature for 60 minutes.

To the yellow-orange solution of (1-Methyl)indenyllithium was added Cp*ZrCl$_3$ (4.51 g, 13.5 mmol, used as received from Aldrich-475181) quickly in one portion as a yellow crystalline solid. Stirred the yellow-orange slurry overnight at room temperature.

Mixture allowed to settle for 30 min. Dark brown solution was decanted from pale yellow solids, rinsed solids on glass frit with 100 ml dry ether. Extracted solids on frit with 100 ml dichloromethane, affording a yellow suspension. Filtered through Celite plug on frit and evaporated volatiles to yield a yellow solid. Recrystallized from ether/pentane to afford 2.70 g (47%). Additional material obtained from mother liquor: 1.19 g (20%)

$^1$H NMR ($C_6D_6$, 500 MHz, 35° C.): δ 1.70 (15H, s, Cp*), 2.30 (3H, s, indenyl CH$_3$), 5.56 (2H, ABq, indenyl CH, CH), 7.05 (1H, dd, indenyl CH), 7.10 (1H, dd, indenyl CH), 7.24 (1H, dt, indenyl CH), 7.56 (1H, dq, indenyl CH).

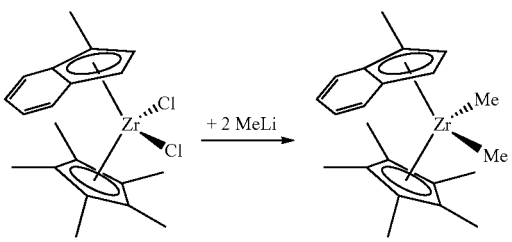

(1-Methylindenyl)(pentamethylcyclopentadienyl) zirconium(IV)dimethyl (IV-C)

(1-Methylindenyl)(pentamethylcyclopentadienyl)zirconiumdichloride (4.92 g, 11.5 mmol) was slurried in 50 mL diethyl ether and cooled to −50° C. To this, a solution of MeLi (14.8 mL of a 1.71M solution in diethyl ether, 25.4 mmol) was added slowly by syringe. The mixture was left to stir and slowly warm to room temperature to give a pink slurry. After 16 h, the solvent was removed under vacuum and the residue extracted with toluene. The insolubles were removed by filtering through a frit lined with Celite and the solvent was removed to give an orange oily solid. The solid was washed with pentane and dried under vacuum (3.89 g, 88% yield). $^1$H NMR δ ($C_6D_6$): 7.53 (d, 1H, 8-IndH), 7.13-6.99 (m, 3H, 5,6,7-IndH), 5.21 (d, 1H, 2-IndH), 5.11 (d, 1H, 3-IndH), 2.20 (s, 3H, 1-MeInd), 1.69 (s, 15H, CpMe$_5$), −0.51 (s, 3H, ZrMe), −1.45 (s, 3H, ZrMe).

Synthesis of (1,3-dimethylindenyl)(tetramethylcyclopentadienyl)Zirconium dimethyl[(1,3-Me$_2$Ind)(CpMe$_4$)]ZrMe$_2$ (IV-D)

2,3,4,5-tetramethyl-1-trimethylsilyl-cyclopenta-2,4-diene

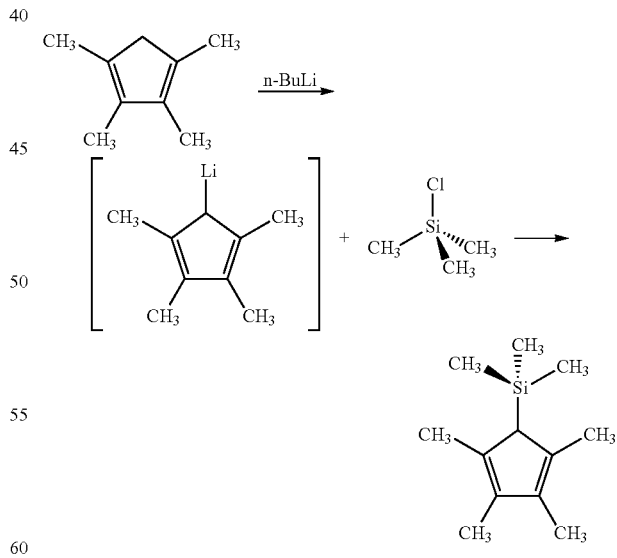

To a 2 liter Erlenmeyer flask, dissolved yellow oil of tetramethylcyclopentadiene (50 g, 409 mmol—obtained from Boulder Scientific) in 1 liter of anhydrous THF. Stirred at room temperature as n-butyllithium (175 ml, 437 mmol) added through a 60 ml plastic syringe with a 20 gauge needle regulating dropwise flow. Formation of a pale yellow precipitate was observed. Reaction is a yellow slurry upon complete addition of lithium reagent. Stirred 1 hr at room temperature, then with vigorous stirring chlorotrimethylsilane (60 ml, 470 mmol) was added and reaction allowed to stir overnight at room temperature. After stirring at room temperature for 15 hr, mixture is a yellow solution. Removed THF solvent with under a stream of $N_2$ to afford an oily residue, which was then extracted with 1 liter of dry pentane and filtered through a celite pad on coarse frit. Removed volatiles under vacuum to afford product as a yellow oil: 62.9 g, 79%. $^1$H NMR ($C_6D_6$, 250 MHz): δ −0.04 (s, Si($CH_3$)$_3$), δ 1.81, (s, $CH_3$), δ 1.90 (s, $CH_3$), δ 2.67 (s, CH)

Synthesis of (tetramethylcyclopentadienyl)zirconium trichloride

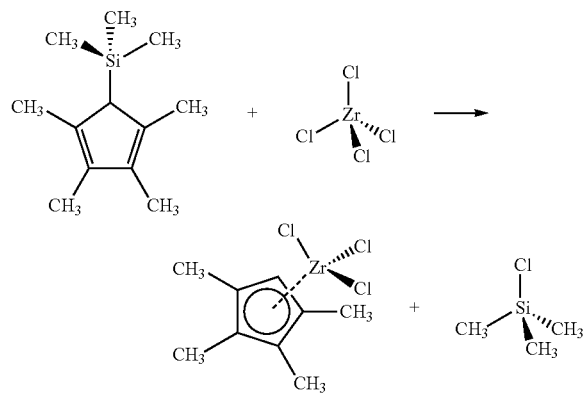

In a drybox, charged solid $ZrCl_4$ (30.0 g, 129 mmol) to a 450 ml Chemglass pressure vessel with magnetic spinbar, suspended in 100 ml dry toluene. Dispensed 2,3,4,5-tetramethyl-1-trimethylsilyl-cyclopenta-2,4-diene as a yellow oil (27.5 g, 142 mmol) and rinsed down with additional 100 ml dry toluene. Sealed pressure vessel with threaded cap with Viton o-ring, and heated on a fitted aluminum heating mantle to 110° C. for 90 min. Solution darkens with time, and insolubles were present during reaction. Vessel was allowed to stir overnight and cool to room temperature. Vessel was opened and solvent volume reduced under stream of $N_2$, affording a thick red sludge. Extracted with 2×50 ml dry pentane then with 100 ml dry ether. Red solution removed and recovered product as pale red solid: 35.4 g, 85%. $^1$H NMR ($C_6D_6$, 250 MHz): δ 1.89 (br s, $CH_3$), δ 2.05 (br s, $CH_3$), δ 5.78 (br s, CH)

Synthesis of 1,3-dimethylindene

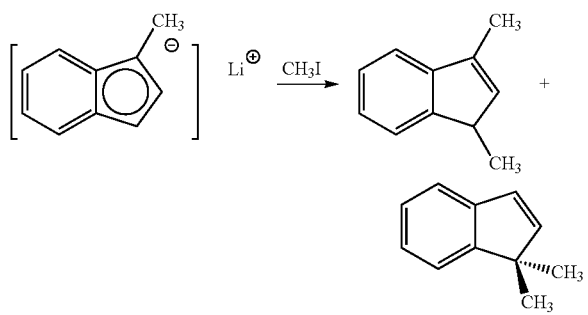

1-Methyl-indenyllithium: Freshly distilled 3-Methylindene (33.75 g 259.24 mmol) was dissolved in pentane (1 L). $Et_2O$ (10 ml), then 1.6M n-butyllithium in hexanes (107 mL, 171.2 mmol) and 2.5M n-butyllithium in hexanes (34.2 mL, 85.5 mmol) were added to the clear stirring solution. Immediately a flaky white solid precipitated. After stirring overnight, the suspension was filtered and the white solid dried in vacuo (33.88 g, 248.90 mmol, 97%). 1H NMR (THF-d8): δ 2.41 (s, 3H), 5.68 (d, 1H), 6.31 (d, 1H), 6.41 (m, 2H), 7.22 (m, 2H).

In a drybox, iodomethane (2.0 ml, 32.1 mmol) was dissolved in 80 ml dry diethyl ether in a 250 ml round bottom flask with magnetic spinbar. Flask was placed in a isohexane cold bath (−25° C.) in a wide mouth dewar. In a separate 100 ml Erlenmeyer flask, a room temperature solution of 1-methylindenyl lithium (3.50 g, 25.7 mmol) was prepared in 50 ml dry diethyl ether, affording a yellow solution. Slow, dropwise addition of indenyl lithium solution to the cold, stirred solution of iodomethane was performed over 15 min. Continued stirring at low temperature for 30 min, then removed the cold bath and allowed the reaction to warm to room temperature overnight. Solution is turbid white after stirring 15 hr at room temperature. Reduced solution volume under nitrogen flow, then volatiles evaporated under high vacuum. Extracted solids with 2×80 ml isohexane and filtered through pad of celite on coarse frit. Filtrates evaporated under high vacuum to afford brown oil. Dissolved in 5 ml dichloromethane and loaded via pipet onto silica gel column (Biotage SNAP 100 g), eluting with dichloromethane:isohexane (gradient, 2-20%). Fractions combined and evaporated to afford a clear oil. Collected 2.54 g, 68%.

$^1$H NMR ($C_6D_6$, 500 MHz): δ 1.11 (d, J=7.5 Hz, —CHCH$_3$), δ 1.96 (s, CH=CCH$_3$), δ 3.22 (m, CHCH$_3$), δ 5.91 (m, CH=CCH$_3$), δ 7.15-7.27 (aromatic CH). Mixture contains minor isomer 3,3-dimethylindene in 1:10 ratio with desired product. δ 1.17 (s, CH$_3$), δ 6.14 (d, J=5.5 Hz, CHH), δ 6.51 (d, J=5.5 Hz, CHH).

Synthesis of 1,3-dimethylindenyl lithium

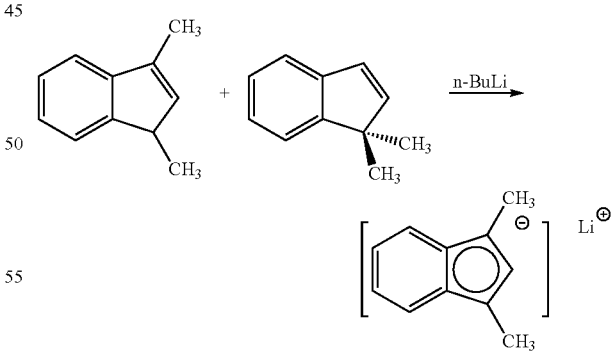

Dissolved 2.54 g (17.6 mmol) of clear oil, 10:1 mixture of 1,3-dimethylindene and 3,3-dimethylindene, in 35 ml dry pentane. Stirred at room temperature as 6.2 ml of a 2.5 M hexane solution of n-butyllithium (15.5 mmol) was added slowly, dropwise. White precipitate formed immediately. Stirred at room temperature for 45 min, then filtered supernatant via cannula. Suspended the residue in 30 ml dry pentane and cooled in drybox freezer (−27° C.) for 60 min.

Filtered supernatant and dried in vacuo to white powder, 2.34 g (88%) and used as-is for subsequent reaction step without characterization.

Synthesis of [(1,3-dimethylindenyl)(tetramethylcyclopentadienyl)]Zirconium dichloride

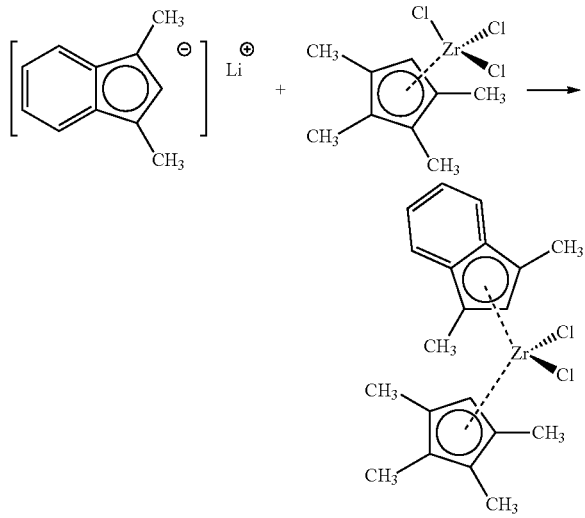

Weighed 3.50 g (10.98 mmol) tan powder of (tetramethylcyclopentadienyl)zirconium trichloride into a 100 ml flat bottom glass bottle with magnetic spinbar. Suspended in 80 ml dry diethyl ether. Stirred as 1,3-dimethylindenyl lithium (1.65 g, 10.99 mmol) added as powder over several minutes. Rinsed down with additional 20 ml ether. Capped bottle and stirred overnight at room temperature. Mixture a yellow slurry after stirring 15 hr at room temperature. Evaporated volatiles under high vacuum, then extracted residue with 2×80 ml dichloromethane. Filtered through celite pad on coarse frit. Concentrated in vacuo and filtered again through fresh celite on coarse frit. Dried in vacuo to free flowing yellow powder, 3.6 g (77%). $^1$H NMR (CD$_2$Cl$_2$, 500 MHz): δ 1.89 (s, CH$_3$ of Cp$^{Me4}$), δ 1.90 (s, CH$_3$ of Cp$^{Me4}$), δ 2.40 (s, CH$_3$ of C$_9$ fragment), δ 5.67 (s, CH of Cp$^{Me4}$), δ 6.33 (s, CH of C$_9$ fragment), δ 7.24 (AA'BB', aromatic CH of C$_9$ fragment), δ 7.52 (AA'BB', aromatic CH of C$_9$ fragment). Contains ca. 15% diethyl ether.

Synthesis of [(1,3-dimethylindenyl)(tetramethylcyclopentadienyl)]Zirconium dimethyl (IV-D)

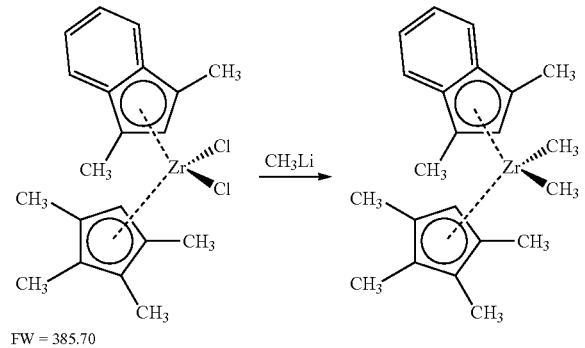

FW = 385.70

In the drybox, suspended bright yellow powder of (1,3-Me$_2$Ind)(Cp$^{Me4}$)ZrCl$_2$ (3.6 g, 8.4 mmol) in 75 ml dry diethyl ether in a 100 ml amber glass flat-bottom bottle with magnetic spinbar. Cooled bottle to −10 C in isohexane bath, stirred as solution of methyllithium (1.6 M in ether) delivered via syringe in portions (4×3 ml, 19.2 mmol). Capped bottle with septum and stirred overnight, allowing cold bath to slowly warm to room temperature. Evaporated slurry to dryness under high vacuum. Extracted with 3×50 ml dichloromethane and filtered through celite on coarse frit. Concentrated under stream of nitrogen, then added pentane. Stirred 15 min then evaporated volatiles. Washed solids with cold pentane, dried in vacuo. Collected as tan powder, 1.67 g; second crop recovered from filtrate, 0.52 g. Combined yields 2.19 g, 67%. $^1$H NMR (CD$_2$Cl$_2$, 500 MHz): δ −1.22 (s, ZrCH$_3$), 1.78 (s, CH$_3$ of Cp$^{Me4}$ fragment), 1.87 (s, CH$_3$ of Cp$^{Me4}$ fragment), 2.25 (s, CH$_3$ of C$_9$ fragment), 4.92 (s, CH of Cp$^{Me4}$ fragment), 5.60 (s, CH of C$_9$ fragment), 7.14 (AA'BB', aromatic CH of C$_9$ fragment), 7.44 (AA'BB', aromatic CH of C$_9$ fragment). $^{13}$C{$^1$H} NMR (CD$_2$Cl$_2$, 125 MHz): δ 11.64 (CH$_3$ of Cp$^{Me4}$ fragment), 12.91 (CH$_3$ of of C$_9$ fragment), 13.25 (CH$_3$ of Cp$^{Me4}$ fragment), 37.23 (ZrCH$_3$), 106.34 (CH of Cp$^{Me4}$ fragment), 115.55 (CH of C$_9$ fragment); quaternary $^{13}$C resonances 107.36, 117.51, 122.69, 125.06.

Synthesis of Meso-O(1-SiMe2Indenyl)2Zirconium dimethyl (V-A)

To a slurry of meso-O—(SiMe$_2$Indenyl)$_2$ZrCl$_2$ (purchased from Süd-Chemie Catalytica; 40.0 g; 83.2 mmol) in about 300 mL of ether was added 54.0 mL of MeMgBr (3.0 M/ether; 162 mmol) at room temperature. After stirring the slurry for 1.5 hours, the volatiles were removed; heptane (about 300 mL) was added to the resultant solid and heated to 80° C. for 30 minutes. The slurry was filtered and the supernatant was cooled to −30° C. resulting in the formation of a crystalline solid that was isolated by filtration, washed with pentane and dried under vacuum. The yield was 26.0 g. $^1$HNMR δ (C$_6$D$_6$): 7.57 (m, 2H), 7.42 (m, 2H), 7.02 (m, 2H), 6.94 (m, 2H), 6.31 (d, 2H), 5.82 (d, 2H), 0.44 (s, 6H), 0.34 (s, 6H), 0.00 (s, 3H), −2.07 (s, 3H).

Catalyst Preparations

Dehydration of Silica at 610° C.

Ineos ES757 silica (3969 g) was charged into a dehydrator (6 ft length, 6.25 in diameter) equipped with a 3-zone heater then fluidized with dry N2 gas at a flow rate of 0.12 ft$^3$/s. Afterwards, the temperature was raised to 200° C. in a 2 h period. After holding at 200° C. for 2 h, the temperature was raised to 610° C. in a 6 h period. After holding at 610° C. for 4 h, the temperature was allowed to cool to ambient temperature over a 12 h period. The silica was transferred under N$_2$ to an APC can then stored under N$_2$ pressure (20 psig).

Preparation of Methyl Aluminoxane Supported on Silica (SMAO)

In a typical procedure, Ineos ES757 silica (741 g), dehydrated at 610° C., was added to a stirred (overhead mechanical conical stirrer) mixture of toluene (2 L) and 30 wt % solution of methyl aluminoxane in toluene (874 g, 4.52 mol). The silica was chased with toluene (200 mL) then the mixture was heated to 90° C. for 3 h. Afterwards, volatiles were removed by application of vacuum and mild heat (40° C.) overnight then the solid was allowed to cool to room temperature.

Typical Small Scale Catalyst Preparation for Laboratory Salt Bed Reactor

In a N2 purged drybox, 3.00 grams of SMAO (4.5 mmol MAO/g SMAO) were transferred to a 125 ml Cel-Stir mixer. Pentane (50 mL) was added to create a slurry. The slurry was stirred at ambient temperature. The metallocene (0.11 mmol) was dissolved in a minimal amount of toluene (~2 mL). This solution was then added to the stirring slurry. The mixture was allowed to stir for one hour. After the allotted time, the mixture was filtered onto a glass frit and washed with fresh pentane (2×10 mL) then dried for at least one hour.

Description of Laboratory Salt Bed Reactor

Under a $N_2$ atmosphere, a 2 L autoclave was charged with dry salt (200 g) and SMAO (3 g). At a pressure of 2 psig $N_2$, dry, degassed 1-hexene (see Tables 10 and 11) was added to the reactor with a syringe. The reactor was sealed, heated to 80° C. while stirring the bed, then charged with $N_2$ to a pressure of 20 psig. Then, solid catalyst was injected into the reactor with ethylene at a pressure of 220 psig; ethylene flow was allowed over the course of the run. The temperature was raised to 85° C. Hexene was fed into the reactor as a ratio to ethylene flow (0.08 g/g). Hydrogen was fed into the reactor as a ratio to ethylene flow per the description in Table 10. The hydrogen and ethylene ratios were measured by on-line GC analysis. Polymerizations were halted after 1 h by venting the reactor, cooling to room temperature then exposing to air. The salt was removed by stirring the crude product in water. The polymer was obtained by filtration then drying in a vacuum oven.

Large Scale Catalyst Preparations for 24-Inch Diameter Gas-Phase Pilot Plant Testing A 5 L 3-neck Morton flask was charged with pentane (4 L) then stirred (140 rpm) with a mechanical stirrer while charged with SMAO (375 g). A solution containing (1-EtInd)$_2$ZrMe$_2$ (IV-A/B), HfPMe$_2$ (III), and toluene was added with an addition funnel over the course of an hour. The slurry took on a green color and was allowed to stir for an additional hour. The mixture was then filtered and dried in vacuo for a total of 8 hours. Results are shown in Table 12.

TABLE 10

Feed conditions for laboratory salt-bed reactor experiments

| SMAO-Metallocene | Initial Charge C6 (mL) | Initial Charge H2 (sccm) | Feed Ratio C6/C2 (g/g) | Feed Ratio H2/C2 (mg/g) | Amount of cat used (mg) |
|---|---|---|---|---|---|
| IV-A/B | 2 | 0 | 0.08 | 0 | 18.3 |
| IV-A/B | 2 | 17 | 0.08 | 0 | 41.5 |
| IV-A/B | 2 | 100 | 0.08 | 3 | 43.5 |
| IV-C | 2 | 0 | 0.08 | 0 | 18.3 |
| IV-C | 3 | 10.5 | 0.08 | 0 | 40.3 |
| IV-C | 4.9 | 10.5 | 0.08 | 0 | 38.9 |
| IV-C | 3 | 45 | 0.08 | 3 | 43.5 |
| IV-C | 3 | 400 | 0.08 | 3 | 43.5 |
| IV-D | 2 | 51 | 0.08 | 0 | 30.4 |
| IV-D | 2 | 51 | 0.08 | 0 | 30.7 |
| III | 2 | 261 | 0.08 | 1 | 50.8 |
| III | 2 | 300 | 0.08 | 1 | 30.4 |
| III | 2 | 0 | 0.08 | 0 | 41.7 |
| III | 2 | 100 | 0.08 | 3 | 40.1 |

TABLE 11

Polymerization results for laboratory salt-bed reactor experiments

| SMAO-Metallocene | Productivity (g/g) | Average H2/C2 (ppm/mol) | Mn/1000 | Mw/1000 | Mz/1000 | Mw/Mn | SCB Content Me/1000C (Corr) |
|---|---|---|---|---|---|---|---|
| IV-A/B | 1530 | 0.5 | 39 | 131 | 278 | 3.4 | 6.1 |
| IV-A/B | 1525 | 0.5 | 40 | 126 | 264 | 3.2 | 6.0 |
| IV-A/B | 993 | 4.2 | 11 | 47 | 116 | 4.3 | 5.3 |
| IV-C | 1350 | 0.2 | 57 | 204 | 471 | 3.5 | 3.4 |
| IV-C | 1953 | 0.2 | 57 | 187 | 371 | 3.3 | 4.9 |
| IV-C | 1900 | 0.5 | 34 | 145 | 312 | 4.2 | 6.2 |
| IV-C | 777 | 4.3 | 13 | 60 | 134 | 4.6 | 3.8 |
| IV-C | 805 | 6.3 | 9 | 48 | 118 | 5.6 | 3.4 |
| IV-D | 1751 | 0.3 | 39 | 168 | 427 | 4.3 | 6.1 |
| IV-D | 641 | 4.3 | 19 | 73 | 142 | 3.8 | 3.8 |
| III | 3510 | 2.0 | 69 | 193 | 432 | 2.8 | 12.5 |
| III | 4846 | 4.2 | 43 | 114 | 220 | 2.7 | 9.5 |
| III | 4825 | 4.8 | 47 | 133 | 269 | 2.8 | 12.1 |
| III | 4677 | 10.2 | 21 | 63 | 128 | 3.0 | 10.3 |

TABLE 12

Blend Combinations

| (1EtInd)2ZrMe2 (IV-A/B) | | (CpPr)2HfMe2 (III) | | (1EtInd)2ZrMe2 |
|---|---|---|---|---|
| mass (g) | mmol | mass (g) | mmol | mole fraction |
| 2.89 | 7.09 | 8.86 | 20.95 | 0.25 |
| 2.87 | 7.04 | 8.94 | 21.14 | 0.25 |
| 5.75 | 14.10 | 5.97 | 14.12 | 0.50 |
| 5.75 | 14.10 | 5.97 | 14.12 | 0.50 |

75% HfPMe$_2$/25% (1-EtInd)$_2$ZrMe$_2$ Catalyst Preparation Batch 2

A similar procedure as described above was employed for the second batch of 75/25 catalyst. A mixture of SMAO was used comprising of 204.15 g from UT-331-142, 176.17 g from UT-331-101, 209.49 g from UT-331-124, and 160.19 g form UT-331-143. For the second batch, 4 L of pentane was added first to the Morton flask followed by the SMAO so clumping would not occur. Two separate solutions were made with 2.87 g (7.09 mmol) of (1-EtInd)$_2$ZrMe$_2$ and 8.94 g (20.95 mmol) of HfPMe2 in 20 mL of toluene.

50% HfPMe$_2$/50% (1-EtInd)$_2$ZrMe$_2$ Catalyst Preparation Batch 1 & 2

The same procedure used to prepare the second batch of 75/25 catalyst was used for both sets of 50/50 catalyst. Batch 1 used SMAO from UT-331-143, 5.75 g (14.10 mmol) of (1-EtInd)$_2$ZrMe$_2$, and 5.97 g (14.11 mmol) of HfPMe$_2$. Batch 2 used SMAO from UT-331-144, 5.75 g (14.09 mmol) of (1-EtInd)$_2$ZrMe$_2$, and 5.97 g (14.11 mmol) of HfPMe$_2$.

Mixing of the Catalysts

The two 75/25 batches were combined in a 4 L Nalgene bottle and manually mixed by spinning and shaking the bottle. The two 50/50 batches were also mixed in the same manner.

Spray-Dried Catalyst Preparations

Spray Dried HfP Low (SD-(III)). The feed stock slurry was prepared by first adding 10 wt % MAO (24.7 lbs), toluene (35.8 lbs) and Cabosil TS-610 (3.4 lbs) to a 10 gallon feed tank. The mixture was stirred overnight at room temperature. HfP (III) (28.75 g, 0.06798 mol) was added then the resulting slurry was mixed for another hour at ~38-40° C. before spraying. The catalyst was spray dried at a slurry feed rate of 93 lb/h, 90% atomizer speed, and outlet temperature of 80° C. Yield was 2289 g (85%). Analytical data are reported in Table 13.

TABLE 13

Analytical data for supported HfP (III)

| Catalyst | wt % Al | wt % Hf | Al mmol/g actual | Hf micro mol/g | Al/Hf actual |
|---|---|---|---|---|---|
| SD-(III) | 16.0 | 0.73 | 5.9 | 41 | 145 |

Description of 24-Inch Diameter Gas-Phase ReactorReactor

The polymerization was conducted in a continuous gas phase fluidized bed reactor having a straight section of 24 inch (61 cm) diameter with a length of approximately 11.75 feet (3.6 m) and an expanded section of 10.2 feet (3.1 m) length and 4.2 feet (1.3 m) diameter at the largest width. The fluidized bed is made up of polymer granules, The gaseous feed streams of ethylene and hydrogen together with liquid 1-hexene were mixed together in a mixing tee arrangement and introduced below the reactor bed into the recycle gas line. The individual flow rates of ethylene, hydrogen and 1-hexene were controlled to maintain fixed composition targets. The ethylene concentration was controlled to maintain a constant ethylene partial pressure. They hydrogen was controlled to maintain a constant hydrogen to ethylene mole ratio. The concentrations of all gasses were measured by an on-line gas chromatograph to ensure relatively constant composition in the recycle gas stream.

The solid catalyst was injected directly into the fluidized bed using purified nitrogen as a carrier. Its rate of injection was adjusted to maintain a constant production rate of the polymer. The reacting bed of growing polymer particles was maintained in a fluidized state by continually flowing the makeup feed and recycle gas through the reaction zone at a superficial gas velocity 1-3 ft/sec (0.3 to 0.9 m/sec). The reactor was operated at a total pressure of 300 psig (2068 kPa gauge). To maintain a constant reactor temperature, the temperature of the recycle gas was continuously adjusted up or down to accommodate any changes in the rate of heat generation due to the polymerization.

A solution of anti-static agents in hexane (1:1 Aluminum stearate:N-nonyldiethanolamine at 20 wt %) was fed into the reactor using a mixture of iso-pentane and nitrogen at such a rate as too maintain ca. 30 ppm anti-static agents in the fluidized bed.

The fluidized bed was maintained at a constant height by withdrawing a portion of the bed at a rate equal to the rate of formation of particulate product. The product was removed semi-continuously via a series of valves into a fixed volume chamber, which was simultaneously vented back to the reactor to allow highly efficient removal of the product, while at the same time recycling a large portion of the unreacted gases back to the reactor, This product was purged to remove entrained hydrocarbons and treated with a small stream of humidified nitrogen to deactivate any trace quantities of residual catalyst and cocatalyst.

Run Summary

Examples of run conditions for the polymerizations are shown in Table 14.

TABLE 14

Run conditions for polymerizations in 24-Inch Diameter Gas-Phase Reactor

| | Polymerization Example | | | |
|---|---|---|---|---|
| MCNs | (III) | 3:1 (III):(IV-A/B) | 3:1 (III):(IV-A/B) | 3:1 (III):(IV-A/B) |
| Cat Density gm/cc | 0.34 | 0.40 | 0.40 | 0.40 |
| Total Polymer Produced | 4853 | 11386 | 4452 | 3058 |
| Bed Turnovers (whole part) | 6.98 | 16.42 | 6.41 | 4.40 |
| Residence Time | 4.21 | 4.26 | 4.48 | 4.55 |
| C2 Concentration (mole %) | 69.9 | 70.1 | 70.0 | 70.0 |
| C2 Partial Pressure (psia) | 220 | 220 | 220 | 220 |
| H2 Concentration (ppm) | 293 | 315 | 296 | 232 |
| H2/C2 Analyzer Ratio (ppm/mole %) | 4.19 | 4.50 | 4.23 | 3.31 |
| Hexene conc (mole %) | 1.20 | 1.90 | 1.47 | 1.56 |
| C6/C2 Analyzer Ratio | 0.0172 | 0.0271 | 0.0210 | 0.0223 |
| C2 Feed (lb/hr) | 187 | 199 | 189 | 182 |
| H2/C2 Flow Ratio (Mlb/lb) | 0.059 | 0.166 | 0.149 | 0.116 |
| C6/C2 Flow Ratio | 0.0988 | 0.1335 | 0.0991 | 0.1040 |
| IC5 (mole %) | 2.5 | 2.2 | 2.4 | 2.3 |
| N2 Conc (mole %) | 26.39 | 25.77 | 26.08 | 26.03 |
| Reactor Vent Rate (lb/hr) | 16.67 | 17.57 | 7.08 | 18.15 |
| Reactor Pressure (psia) | 314.5 | 314.5 | 314.2 | 314.6 |
| Bed Temperature (deg C.) | 78.8 | 78.8 | 78.7 | 78.7 |
| Exchanger dp (psi) | 0.409 | 0.380 | 0.400 | 0.416 |
| Plate dp ("H2O) | 91.97 | 92.24 | 90.62 | 91.48 |
| Gas Velocity (ft/sec) | 2.25 | 2.25 | 2.25 | 2.25 |
| Bed Weight (lbs) | 695.4 | 693.4 | 694.1 | 695.7 |
| Bed Level (ft) | 14.2 | 13.4 | 13.1 | 13.0 |
| Fluidized Bed Density (lb/ft3) | 17.80 | 18.95 | 19.08 | 19.07 |
| Exp sect diff press (inch H20) | 6.35 | 4.96 | 4.59 | 4.63 |
| Cat Feed Rate (seconds) | 21.00 | 15.00 | 16.00 | 16.00 |
| Cat feed rate (g/hr) | 9.07 | 12.43 | 11.55 | 11.55 |
| Cat Feeder Efficiency (%) | 1.10 | 0.93 | 0.92 | 0.92 |
| N2 Sweep with Continuity Additive lb/hr | 1.3 | 1.3 | 1.3 | 1.3 |
| IC5 Flush with Continuity Additive lb/hr | 4.1 | 4.0 | 4.1 | 4.0 |
| N2 flow to annulus with cat lb/hr | 3.0 | 3.2 | 3.2 | 3.2 |
| N2 flow with Cat lb/hr | 3.0 | 3.0 | 3.0 | 3.0 |
| Production Rate (lb/hr) Drops | 165.0 | 162.8 | 155.0 | 152.8 |
| Cat Activity matl balance (gm/gm) Drops | 8264 | 5944 | 6092 | 6005 |
| Melt Index (I2) | 0.93 | 1.06 | 1.23 | 0.72 |
| HLMI (I21) | 27.23 | 61.67 | 67.01 | 38.17 |
| MFR (I21/I2) | 29.28 | 58.18 | 54.48 | 53.09 |

TABLE 14-continued

Run conditions for polymerizations in 24-Inch Diameter Gas-Phase Reactor

| Density (gm/cc) | 0.9196 | 0.9210 | 0.9263 | 0.9253 |
|---|---|---|---|---|

| Polymerization Example Catalyst Example | | | |
|---|---|---|---|
| MCNs | 1:1 (III):(IV-A/B) | 1:1 (III):(IV-A/B) | 1:1 (III):(IV-A/B) |
| Cat Density gm/cc | 0.38 | 0.38 | 0.38 |
| Total Polymer Produced | 4338 | 3624 | 2359 |
| Bed Turnovers (whole part) | 6.26 | 5.22 | 3.43 |
| Residence Time | 5.19 | 4.86 | 5.58 |
| C2 Concentration (mole %) | 69.8 | 70.0 | 69.0 |
| C2 Partial Pressure (psia) | 220 | 220 | 200 |
| H2 Concentration (ppm) | 294 | 321 | 192 |
| H2/C2 Analyzer Ratio (ppm/mole %) | 4.21 | 4.59 | 2.78 |
| Hexene conc (mole %) | 1.74 | 2.14 | 2.41 |
| C6/C2 Analyzer Ratio | 0.0249 | 0.0305 | 0.0350 |
| C2 Feed (lb/hr) | 172 | 174 | 89 |
| H2/C2 Flow Ratio (Mlb/lb) | 0.185 | 0.197 | 0.106 |
| C6/C2 Flow Ratio | 0.0988 | 0.1330 | 0.1347 |
| IC5 (mole %) | 2.4 | 2.2 | 2.3 |
| N2 Conc (mole %) | 26.00 | 25.60 | 26.30 |
| Reactor Vent Rate (lb/hr) | 11.90 | 19.82 | 45.33 |
| Reactor Pressure (psia) | 314.4 | 314.6 | 289.9 |
| Bed Temperature (deg C.) | 78.9 | 78.8 | 78.2 |
| Exchanger dp (psi) | 0.373 | 0.385 | 0.433 |
| Plate dp ("H2O) | 92.07 | 92.45 | 96.76 |
| Gas Velocity (ft/sec) | 2.25 | 2.25 | 2.24 |
| Bed Weight (lbs) | 693.5 | 694.6 | 688.4 |
| Bed Level (ft) | 13.3 | 13.7 | 12.6 |
| Fluidized Bed Density (lb/ft3) | 18.96 | 18.51 | 19.88 |
| Exp sect diff press (inch H20) | 4.98 | 5.91 | 4.08 |
| Cat Feed Rate (seconds) | 17.00 | 17.00 | 16.00 |
| Cat feed rate (g/hr) | 10.63 | 10.63 | 11.30 |
| Cat Feeder Efficiency (%) | 0.94 | 0.94 | 0.94 |
| N2 Sweep with Continuity Additive lb/hr | 1.3 | 1.3 | 1.3 |
| IC5 Flush with Continuity Additive lb/hr | 4.0 | 4.0 | 3.6 |
| N2 flow to annulus with cat lb/hr | 3.2 | 3.2 | 3.2 |
| N2 flow with Cat lb/hr | 3.0 | 3.0 | 3.0 |
| Production Rate (lb/hr) Drops | 133.5 | 143.0 | 123.3 |
| Cat Activity matl balance (gm/gm) Drops | 5700 | 6106 | 4955 |
| Melt Index (I2) | 4.86 | 6.17 | 2.20 |
| HLMI (I21) | 239.08 | 319.27 | 99.04 |
| MFR (I21/I2) | 49.19 | 51.75 | 45.02 |
| Density (gm/cc) | 0.9319 | 0.9257 | 0.9254 |

Description of 13.25 Inch Diameter Gas-Phase Reactor

A gas phase fluidized bed reactor of 0.35 meters internal diameter and 2.3 meters in bed height was utilized for polymerizations, with the results shown in Table 15. The fluidized bed was made up of polymer granules and the gaseous feed streams of ethylene and hydrogen together with liquid 1-hexene comonomer were introduced below the reactor bed into the recycle gas line. The individual flow rates of ethylene, hydrogen and 1-hexene were controlled to maintain fixed composition targets. The ethylene concentration was controlled to maintain a constant ethylene partial pressure. The hydrogen was controlled to maintain constant hydrogen to ethylene mole ratio. The concentrations of all the gases were measured by an on-line gas chromatograph to ensure relatively constant composition in the recycle gas stream. The reacting bed of growing polymer particles was maintained in a fluidized state by the continuous flow of the make-up feed and recycle gas through the reaction zone. A superficial gas velocity of 0.6-0.9 meters/sec was used to achieve this. The fluidized bed was maintained at a constant height by withdrawing a portion of the bed at a rate equal to the rate of formation of particulate product. The polymer production rate was in the range of 15-25 kg/hour. The product was removed semi-continuously via a series of valves into a fixed volume chamber. This product was purged to remove entrained hydrocarbons and treated with a small stream of humidified nitrogen to deactivate any trace quantities of residual catalyst.

The solid catalyst was dispersed in degassed and dried mineral oil as a nominal 18 wt % slurry and contacted with the trim catalyst solution for a few seconds to minutes before being injected directly into the fluidized bed using purified nitrogen and isopentane as carriers in a manner that produces an effervescence of nitrogen in the liquid and spray to aid in dispersing the catalyst. The trim catalyst was provided initially as a solution, and substantially diluted with isopentane to a concentration of about 0.015 wt % before being mixed in-line with the slurry catalyst component in a continuous manner prior to injection to the reactor. The relative feeds of the slurry catalyst and the trim catalyst were controlled to achieve an aim target feed ratio of their active polymerization metals, and the feeds adjusted accordingly for overall polymer production rate and the relative amounts of polymer produced by each catalyst based somewhat on polymer flow index MFR and density, while also manipulating reaction temperature and the gas compositions in the reactor. The reacting bed of growing polymer particles was maintained in a fluidized state by continually flowing the makeup feed and recycle gas through the reaction zone at a superficial gas velocity in about the range of 2.0 to 2.2 ft/sec (0.61 to 0.67 m/sec). The reactor was operated at a total pressure of about 350 psig (2413 kPa gauge). To maintain a constant fluidized bed temperature in the reactor, the temperature of the recycle gas was continuously adjusted up or down by passing the recirculating gas through the tubes of a shell-and-tube heat exchanger with cooling water on the shell-side to accommodate any changes in the rate of heat generation due to the polymerization.

A slurry mixture of anti-static agents in degassed and dried mineral oil (1:1 Aluminum stearate:N-nonyldiethanolamine at 20 wt % concentration) was fed into the reactor using a mixture of iso-pentane and nitrogen at such a rate as to achieve a concentration of between 38 and 123 ppmw anti-static agents in the fluidized bed. (row 128) Isopentane and/or nitrogen was optionally employed to assist in conveying and dispersing the slurry mixture of anti-static into the reactor fluidized bed via a ⅛ inch to 3/16 inch OD injection tube thief extending a few inches into the bed from the reactor side wall.

The fluidized bed was maintained at a constant height by withdrawing a portion of the bed at a rate equal to the rate of formation of particulate product. The product was removed semi-continuously via a series of valves into a fixed volume discharge chamber. This product was purged to remove entrained hydrocarbons and treated with a small stream of humidified nitrogen immediately on discharge to a receiving fiberpak drum to deactivate any trace quantities of residual catalyst and cocatalyst.

All numerical values are "about" or "approximately" the indicated value, and take into account experimental error and variations that would be expected by a person having ordinary skill in the art. Further, various terms have been defined above. To the extent a term used in a claim is not defined above, it should be given the broadest definition persons in the pertinent art have given that term as reflected in at least one printed publication or issued patent. All patents, test procedures, and other documents cited in this application are fully incorporated by reference to the extent such disclosure is not inconsistent with this application and for all jurisdictions in which such incorporation is permitted.

TABLE 15

Polymerization Experiments in 13.25 Inch Diameter Gas-Phase Reactor

| Polymerization Example | 1 | 2 | 3A | 3B |
|---|---|---|---|---|
| Trim Metallocene | None | None | IV-A/B | IV-A/B |
| Base Catalyst | SD-(III) | SD-(III) | SD-(III) | SD-(III) |
| Part Bed Turnovers Averaging Data | 1.81 | 1.80 | 1.74 | 2.22 |
| Part BTO's | 17.22 | 5.40 | 6.95 | 5.18 |
| Prod Rate (lbs/hr) | 26.5 | 26.3 | 24.9 | 20.8 |
| Residence Time (hrs) | 3.31 | 3.33 | 3.45 | 4.06 |
| C2 Partial Pressure (psia) | 220.2 | 220.5 | 220.3 | 220.0 |
| C2 Partial Pressure (Bar) | 14.99 | 15.01 | 14.99 | 14.98 |
| H2/C2 Conc Ratio (ppm/m %) | 4.61 | 3.84 | 3.74 | 3.74 |
| C6/C2 Conc Ratio (m/m) | 0.01527 | 0.01539 | 0.01835 | 0.01729 |
| Ethylene (mole %) | 61.03 | 61.05 | 61.34 | 61.26 |
| Isopentane (mole %) | 12.06 | 12.16 | 12.35 | 12.35 |
| Nitrogen (mole %) | 26.75 | 26.56 | 26.47 | 26.58 |
| Isopentane Feed (lb/hr) | 12.01 | 12.01 | 12.01 | 12.01 |
| RX Pressure (psig) | 349.07 | 349.06 | 349.19 | 349.18 |
| Rxn Temperature (° C.) | 85.00 | 84.99 | 85.00 | 85.00 |
| Bed Weight (lbs) | 87.6 | 87.8 | 85.9 | 84.2 |
| Bed Level (ft) | 6.43 | 6.23 | 7.41 | 8.19 |
| Continuity Additive Conc (ppmw prod) | 54.4 | 73.4 | 75.3 | 90.3 |
| Trim Solution Flow (g/hr) | | | 120.0 | 79.7 |
| Trim Catalyst Flow (g/hr) | | | 0.0180 | 0.0119 |
| Slurry Cat Flowrate | 9.50 | 10.00 | 7.00 | 7.00 |
| Slurry Cat Inner Tube IC5 Flow (lb/hr) | 3.01 | 3.00 | 3.00 | 3.00 |
| Slurry Cat Inner Tube N2 Flow (lb/hr) | 5.00 | 5.00 | 5.00 | 5.00 |
| Slurry Cat Outer Tube IC5 Flow (lb/hr) | 12.01 | 12.01 | 12.01 | 12.01 |
| Slurry Cat Outer Tube N2 Flow (lb/hr) | 5.02 | 5.01 | 5.02 | 5.00 |
| Plenum Flow (lb/hr) | 62.01 | 62.56 | 58.42 | 56.40 |
| Melt Index (dg/min) | 0.73 | 0.49 | 1.68 | 1.01 |
| MI-5 (dg/min) | 2.12 | 1.38 | 5.75 | 3.10 |
| High Load Melt Index (dg/min) | 18.2 | 11.7 | 83.2 | 37.0 |
| MFR(HLMI/MI) | 25.0 | 23.9 | 49.4 | 36.6 |
| MFR I21/I5 | 8.6 | 8.4 | 14.5 | 11.9 |
| Density (g/cc) | 0.9201 | 0.9194 | 0.9340 | 0.9281 |
| Bulk Density (lb/ft 3) | 24.00 | 24.50 | 32.40 | 31.43 |
| Poured Bulk Density (g/cc) | 0.3846 | 0.3926 | 0.5192 | 0.5037 |
| Cat Prod (matl Bal) | 7,801 | 7,373 | 9,956 | 8,300 |
| Polymerization Example | 4B | 4A | 5B | 5A |
| Trim Metallocene | IV-C | IV-C | IV-D | IV-D |
| Base Catalyst | SD-(III) | SD-(III) | SD-(III) | SD-(III) |
| Part Bed Turnovers Averaging Data | 2.13 | 3.00 | 2.12 | 2.63 |
| Part BTO's | 5.68 | 6.00 | 5.65 | 5.26 |
| Prod Rate (lbs/hr) | 20.6 | 21.9 | 20.7 | 19.2 |
| Residence Time (hrs) | 4.22 | 4.00 | 4.25 | 4.56 |
| C2 Partial Pressure (psia) | 220.0 | 220.0 | 220.0 | 220.2 |
| C2 Partial Pressure (Bar) | 14.98 | 14.97 | 14.98 | 14.99 |
| H2/C2 Conc Ratio (ppm/m %) | 3.78 | 3.78 | 3.80 | 3.74 |
| C6/C2 Conc Ratio (m/m) | 0.01742 | 0.01823 | 0.01614 | 0.01709 |
| Ethylene (mole %) | 60.95 | 60.79 | 60.97 | 61.29 |

TABLE 15-continued

Polymerization Experiments in 13.25 Inch Diameter Gas-Phase Reactor

| | | | | |
|---|---|---|---|---|
| Isopentane (mole %) | 12.30 | 12.31 | 12.26 | 12.42 |
| Nitrogen (mole %) | 26.46 | 26.31 | 26.58 | 26.49 |
| Isopentane Feed (lb/hr) | 12.01 | 12.01 | 12.01 | 12.01 |
| RX Pressure (psig) | 349.19 | 349.15 | 349.16 | 349.16 |
| Rxn Temperature (° C.) | 85.00 | 85.00 | 85.00 | 85.00 |
| Bed Weight (lbs) | 86.9 | 87.6 | 87.8 | 87.6 |
| Bed Level (ft) | 7.55 | 6.96 | 6.56 | 6.74 |
| Continuity Additive Conc (ppmw prod) | 91.0 | 85.5 | 90.7 | 97.6 |
| Trim Solution Flow (g/hr) | 80.0 | 120.0 | 80.0 | 119.8 |
| Trim Catalyst Flow (g/hr) | 0.0120 | 0.0180 | 0.0120 | 0.0180 |
| Slurry Cat Flowrate | 7.00 | 7.00 | 7.00 | 7.00 |
| Slurry Cat Inner Tube IC5 Flow (lb/hr) | 3.00 | 3.00 | 3.00 | 3.00 |
| Slurry Cat Inner Tube N2 Flow (lb/hr) | 5.00 | 5.00 | 5.00 | 5.00 |
| Slurry Cat Outer Tube IC5 Flow (lb/hr) | 12.01 | 12.01 | 12.01 | 12.01 |
| Slurry Cat Outer Tube N2 Flow (lb/hr) | 5.04 | 5.02 | 5.02 | 5.03 |
| Plenum Flow (lb/hr) | 55.29 | 56.68 | 58.46 | 58.70 |
| Melt Index (dg/min) | 1.23 | 1.72 | 0.914 | 1.090 |
| MI-5 (dg/min) | 3.59 | 5.22 | 2.528 | 3.101 |
| High Load Melt Index (dg/min) | 35.9 | 57.0 | 21.3 | 27.8 |
| MFR (HLMI/MI) | 29.1 | 33.1 | 23.3 | 25.5 |
| MFR I21/I5 | 10.0 | 10.9 | 8.4 | 9.0 |
| Density (g/cc) | 0.9274 | 0.9315 | 0.9221 | 0.9238 |
| Bulk Density (lb/ft^3) | 30.03 | 30.93 | 30.33 | 31.42 |
| Poured Bulk Density (g/cc) | 0.4813 | 0.4956 | 0.4861 | 0.5036 |
| Cat Prod (matl Bal) | 8,233 | 8,767 | 8,267 | 7,680 |

| Polymerization Example | 6B | 6A | 3C-1 | 3C-2 |
|---|---|---|---|---|
| Trim Metallocene | V-A | V-A | IV-A/B | IV-A/B |
| Base Catalyst | SD-(III) | SD-(III) | SD-(III) | SD-(III) |
| Part Bed Turnovers Averaging Data | 1.40 | 1.88 | 1.02 | 1.38 |
| Part BTO's | 4.19 | 5.02 | 3.07 | 3.46 |
| Prod Rate (lbs/hr) | 20.4 | 18.1 | 29.7 | 20.0 |
| Residence Time (hrs) | 4.30 | 4.78 | 2.93 | 4.34 |
| C2 Partial Pressure (psia) | 219.7 | 220.0 | 221.2 | 220.0 |
| C2 Partial Pressure (Bar) | 14.96 | 14.98 | 15.06 | 14.98 |
| H2/C2 Conc Ratio (ppm/m %) | 3.76 | 3.75 | 3.55 | 3.77 |
| C6/C2 Conc Ratio (m/m) | 0.01595 | 0.01724 | 0.01692 | 0.01953 |
| Ethylene (mole %) | 61.02 | 61.03 | 61.47 | 60.84 |
| Isopentane (mole %) | 12.29 | 12.43 | 12.21 | 12.09 |
| Nitrogen (mole %) | 26.72 | 26.35 | 26.32 | 26.47 |
| Isopentane Feed (lb/hr) | 12.02 | 12.01 | 12.02 | 12.02 |
| RX Pressure (psig) | 349.15 | 349.12 | 349.18 | 349.17 |
| Rxn Temperature (° C.) | 85.00 | 85.00 | 84.99 | 85.00 |
| Bed Weight (lbs) | 87.9 | 86.5 | 87.1 | 86.8 |
| Bed Level (ft) | 6.71 | 7.01 | 6.81 | 7.15 |
| Continuity Additive Conc (ppmw prod) | 91.7 | 103.6 | 63.2 | 93.7 |
| Trim Solution Flow (g/h) | 100.0 | 150.0 | 80.0 | 80.0 |
| Trim Catalyst Flow (g/hr) | 0.0150 | 0.0225 | 0.0120 | 0.0120 |
| Slurry Cat Flowrate | 7.00 | 7.00 | 7.50 | 5.00 |
| Slurry Cat Inner Tube IC5 Flow (lb/hr) | 3.00 | 3.00 | 3.01 | 3.00 |
| Slurry Cat Inner Tube N2 Flow (lb/hr) | 5.00 | 5.00 | 5.00 | 5.00 |
| Slurry Cat Outer Tube IC5 Flow (lb/hr) | 12.02 | 12.01 | 12.02 | 12.02 |
| Slurry Cat Outer Tube N2 Flow (lb/hr) | 5.02 | 5.03 | 4.99 | 5.03 |
| Plenum Flow (lb/hr) | 59.81 | 59.74 | 66.36 | 65.32 |
| Melt Index (dg/min) | 0.602 | 0.702 | 0.401 | 0.287 |
| MI-5 (dg/min) | 1.640 | 1.994 | 1.183 | 0.851 |
| High Load Melt Index (dg/min) | 14.6 | 19.0 | 13.4 | 10.8 |
| MFR (HLMI/MI) | 24.3 | 27.1 | 33.5 | 37.8 |
| MFR I21/I5 | 8.9 | 9.5 | 11.4 | 12.7 |
| Density (g/cc) | 0.9201 | 0.9234 | 0.9232 | 0.9206 |
| Bulk Density (lb/ft^3) | 30.25 | 30.77 | 30.80 | 32.40 |
| Poured Bulk Density (g/cc) | 0.4848 | 0.4930 | 0.4936 | 0.5192 |
| Cat Prod (matl Bal) | 8,178 | 7,233 | 11,076 | 11,200 |

While the foregoing is directed to embodiments of the present invention, other and further embodiments of the invention can be devised without departing from the basic scope thereof, and the scope thereof is determined by the claims that follow.

What is claimed is:

1. A method of selecting catalysts for making a product specific polyolefin using a blend polydispersity index (bPDI) map, comprising:

generating a plurality of polymers for at least two catalysts, wherein each polymer is generated at a different hydrogen to ethylene mole ratio, wherein one of the at least two catalysts generates a higher molecular weight polymer and another of the at least two catalysts generates a lower molecular weight polymer;

calculating a weight fraction of the lower molecular weight polymer (Flmw) and a weight fraction of the higher molecular weight polymer (Fhmw) from the amount of polymer generated by the first catalyst at each hydrogen to ethylene mole ratio and the amount of polymer generated by the second catalyst at each hydrogen to ethylene mole ratio;

measuring the weight averaged molecular weight and PDI for each polymer;

determining the relationship between the weight average molecular weight of the polymers generated by each of the at least two catalysts and the mole ratio of hydrogen to ethylene, wherein the relationship between the weight average molecular weight and the mole ratio of hydrogen to ethylene for a catalyst is determined from a linear fit of the formula: $1/M_w = \text{Intercept} + \text{Slope}*(H_2/C_2)$;

calculating a weight average molecular weight for the higher molecular weight polymer (hmw) and a weight average molecular weight for the lower molecular weight polymer (lmw) from the relationship of the weight average molecular weight and the mole ratio of the hydrogen to ethylene; and generating a family of bPDI curves for polymers that would be made using a plurality of ratios of a blend of the at least two catalysts for each of a plurality of mole ratios of hydrogen to ethylene, comprising generating a bPDI curve using the relationship bPDI=[Flmw+Fhmw*(hmw/lmw)]*[Flmw*lPDI+ Fhmw*hPDI*(lmw/hmw)], wherein:

lPDI is the polydispersity of the lower molecular weight polymer component;

hPDI is the polydispersity of the higher molecular weight polymer component; and lPDI and hPDI are measured for each polymer;

selecting a ratio for a blend of the at least two catalysts that generates a polymer having a bPDI that matches a polymer fabrication process; and confirming the ratio of the at least two catalysts by generating a polymer at each of the plurality of mole ratios of hydrogen to ethylene.

2. The method of claim 1, comprising:

calculating a b-ratio as the ratio of the Intercept of a first catalyst to the Intercept for a second catalyst;

calculating an m-ratio as the ratio of the Slope of the first catalyst to the Slope for the second catalyst;

wherein:

b-ratio/m-ratio for the catalyst blend is less than about 2;

the b-ratio for the catalyst blend is greater than about 5;

the m-ratio for the catalyst blend is greater than about 5;

a polydispersity of the low molecular weight polymer (lPDI) is greater than about 3.0; and a polydispersity of the high molecular weight polymer (hPDI) is greater than about 3.0.

3. The method of claim 1, wherein the polymer fabrication process comprises blow molding, injection molding, film blowing, or rotomolding.

4. The method of claim 1, wherein the value of a comonomer/ethylene incorporation ratio for one of the at least two catalysts is less than about 0.8 as large as comonomer/ethylene incorporation ratio of another of the at least two catalysts.

5. The method of claim 1, wherein the value of the comonomer/ethylene incorporation ratio for one of the at least two catalysts is less than about 0.25 as large as a comonomer/ethylene incorporation ratio of another of the at least two catalysts.

6. A polymerization catalyst for forming a polyethylene copolymer, comprising:

a catalyst support;

a blend of at least two catalysts selected by:

generating a plurality of polymers for the at least two catalysts, wherein each polymer is generated at a different hydrogen to ethylene mole ratio, wherein one of the at least two catalysts generates a polymer with a higher weight average molecular weight (hmw) and another of the at least two catalysts generates a polymer with a lower weight average molecular weight (lmw), wherein the ratio of hmw to lmw is greater than about 5.0 at a weight average molecular weight of between about 30,000 and about 150,000;

measuring the molecular weight for each polymer;

determining the relationship between the molecular weight of the polymers generated by each of the at least two catalysts and the mole ratio of hydrogen to ethylene;

generating a family of bPDI curves for polymers that would be made using a plurality of ratios of a blend of the at least two catalysts for each of a plurality of mole ratios of hydrogen to ethylene; and selecting a ratio for the catalyst blend of the at least two catalysts that generates a polymer having a bPDI that matches a polymer fabrication process.

7. The system of claim 6, wherein a catalyst impregnated on the catalyst support is bis(n-propylcyclopentadienyl) hafnium $(CH_3)_2$, bis(n-propylcyclopentadienyl) hafnium $F_2$, bis(n-propylcyclopentadienyl) hafnium $Cl_2$, or any combinations thereof.

8. The system of claim 6, wherein a catalyst impregnated on the catalyst support is bis(n-butyl, methyl cyclopentadienyl) zirconium $(CH_3)_2$, bis(n-butyl, methyl cyclopentadienyl) zirconium $Cl_2$, bis(n-butyl, methyl cyclopentadienyl) zirconium $F_2$, or any combinations thereof.

9. The system of claim 6, wherein a catalyst impregnated on the catalyst support is bis(1-ethylindenyl) zirconium $(CH_3)_2$, bis(1-ethylindenyl) zirconium $F_2$, bis(1-ethylindenyl) zirconium $Cl_2$, or any combinations thereof.

10. The system of claim 6, wherein a catalyst impregnated on the catalyst support is represented by the formula:

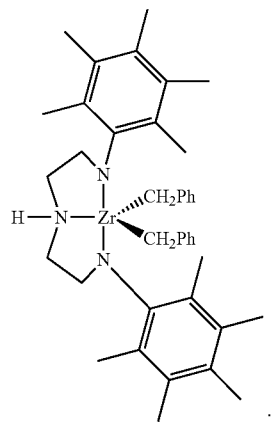

11. The system of claim 6, wherein a catalyst impregnated on the catalyst support is any one, or any combination, of the compounds represented by the following formulas:

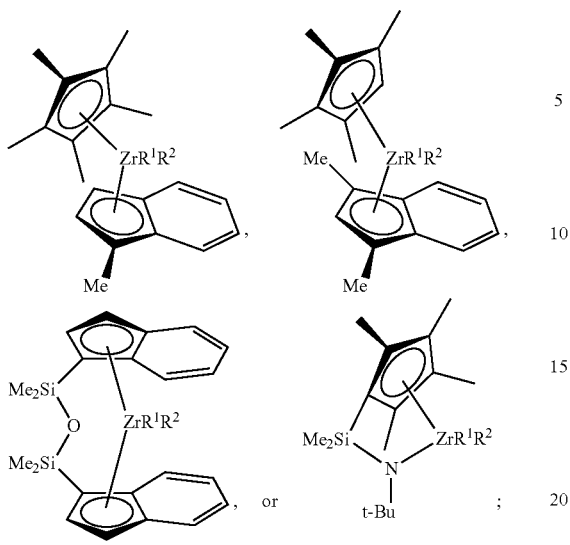
wherein $R^1$ and $R^2$ are each, independently, methyl, chloro, fluoro, or a hydrocarbyl group.
* * * * *